US011505569B2

(12) United States Patent
Albaek et al.

(10) Patent No.: US 11,505,569 B2
(45) Date of Patent: Nov. 22, 2022

(54) GALNAC PHOSPHORAMIDITES, NUCLEIC ACID CONJUGATES THEREOF AND THEIR USE

(71) Applicant: Hoffmann-La Roche, Inc., Little Falls, NJ (US)

(72) Inventors: Nanna Albaek, Birkerød (DK); Jacob Ravn, Skovlunde (DK); Christoph Rosenbohm, Birkerod (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 98 days.

(21) Appl. No.: 16/987,225

(22) Filed: Aug. 6, 2020

(65) Prior Publication Data

US 2021/0017214 A1 Jan. 21, 2021

Related U.S. Application Data

(62) Division of application No. 15/517,685, filed as application No. PCT/EP2015/073331 on Aug. 20, 2015, now abandoned.

(30) Foreign Application Priority Data

Oct. 10, 2014 (EP) .................................... 14188444
Aug. 20, 2015 (EP) .................................... 15181807

(51) Int. Cl.
C07H 15/08 (2006.01)
C07H 15/04 (2006.01)
C07H 21/00 (2006.01)

(52) U.S. Cl.
CPC ............. *C07H 15/08* (2013.01); *C07H 15/04* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 6,057,431 A | 5/2000 | Ishihara et al. | |
| 9,181,549 B2 * | 11/2015 | Prakash | ............... C12N 15/113 |
| 2006/0148740 A1 | 7/2006 | Platenburg | |
| 2009/0203135 A1 | 8/2009 | Forst et al. | |
| 2011/0110960 A1 | 5/2011 | Platenburg | |
| 2012/0122801 A1 | 5/2012 | Platenburg | |
| 2014/0371432 A1 | 12/2014 | Chae et al. | |
| 2021/0017214 A1 | 1/2021 | Albaek et al. | |

FOREIGN PATENT DOCUMENTS

| | | |
|---|---|---|
| AU | 2012353058 | 6/2013 |
| EP | 1222309 | 7/2002 |
| EP | 1285768 | 2/2003 |
| EP | 2796150 | 10/2014 |
| RU | 2599449 | 12/2012 |
| RU | 2015151199 | 6/2017 |
| RU | 2016146817 | 6/2018 |
| RU | 2016146818 | 6/2018 |
| RU | 2016146819 | 6/2018 |
| RU | 2016147047 | 6/2018 |
| RU | 2018136140 | 12/2018 |
| RU | 2015151200 | 1/2019 |
| RU | 2018112167 | 3/2019 |
| WO | WO 2002/094185 | 11/2002 |
| WO | WO 2004/046160 | 6/2004 |
| WO | WO 2005/023825 | 3/2005 |
| WO | WO 2005/023995 | 3/2005 |
| WO | WO 2007/031091 | 3/2007 |
| WO | WO 2007/134181 | 11/2007 |
| WO | WO 2007/146511 | 12/2007 |
| WO | WO 2008/113832 | 9/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/073809 | 6/2009 |
| WO | WO 2009/090182 | 7/2009 |
| WO | WO 2009/100320 | 8/2009 |
| WO | WO 2009/124238 | 10/2009 |
| WO | WO 2009/124295 | 10/2009 |
| WO | WO 2010/036698 | 4/2010 |
| WO | WO 2011/017521 | 2/2011 |
| WO | WO 2011/085102 | 7/2011 |
| WO | WO 2011/104169 | 9/2011 |
| WO | WO 2011/115818 | 9/2011 |
| WO | WO 2012/083046 | 6/2012 |
| WO | WO 2013/089522 | 6/2013 |
| WO | WO 2014/076196 | 5/2014 |

(Continued)

OTHER PUBLICATIONS

Alnylam Pharmaceuticals Presentation, "RNAi Therapeutics Using Conjugate Delivery Platform," Oct. 8, 2013, 28 pages.
Drickamer et al., "Recent insights into structures and functions of C-type lectins in the immune system," Current Opinion in Structural Biology., 2015, 34:26-34.
Kelm and Schauer, "Excerpt from International Review of Cytology," A Survey of Cell Biology, 1997, 175:146.
Christensen et al., "Intercalating nucleic acids containing insertions of 1-O-(1-pyrenylmethyl)glycerol: stabilisation of dsDNA and discrimination of DNA over RNA," Nucl. Acids. Res., Nov. 15, 2002, 30(22):4918-4925.
Coombs et al., "Two categories of mammalian galactose-binding receptors distinguished by glycan array profiling," Glycobiology, Aug. 2006, 16(8):1C-7C.
Dubber et al., "Solid-phase synthesis of multivalent glycoconjugates on a DNA synthesizer", Bioconjug Chem., Jan. 2003-Feb. 2003, 14(1):239-246.

(Continued)

Primary Examiner — Traviss C McIntosh, III
(74) Attorney, Agent, or Firm — Smith Gambrell & Russell LLP; Judy Jarecki-Black; Ram W. Sabnis

(57) ABSTRACT

This invention generally relates to the field of phosphoramidite derivatives. In particular, the invention relates to N-Acetylgalactosamine phosphoramidite molecules and to conjugates of nucleic acid molecules with N-Acetylgalactosamine containing molecules. Also provided are methods for preparation of these molecules and possible uses thereof, in particular in medicine.

2 Claims, 24 Drawing Sheets
Specification includes a Sequence Listing.

(56) References Cited

FOREIGN PATENT DOCUMENTS

| WO | WO 2014/118267 | 8/2014 |
|----|----------------|--------|
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/179629 | 11/2014 |
| WO | WO 2014/205451 | 12/2014 |
| WO | WO 2015/168532 | 11/2015 |
| WO | WO 2015/168589 | 11/2015 |
| WO | WO 2015/168618 | 11/2015 |
| WO | WO 2015/168632 | 11/2015 |
| WO | WO 2015/168635 | 11/2015 |

OTHER PUBLICATIONS

Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol. Biosyst., Aug. 2009, 5(8):838-843.

Freier & Altmann, "The ups and downs of nucleic acid duplex stability: structure-stability studies on chemically-modified DNA:RNA duplexes," Nucl. Acid Res., 1997, 25(22):4429-4443.

International Search Report and Written Opinion in International Application No. PCT/EP2015/073331, dated Nov. 24, 2015, 10 pages.

International Preliminary Report on Patentability in International Application No. PCT/EP2015/073331, dated Apr. 11, 2017, 7 pages.

Jeon, "Excerpt from International Review of Cytology: A Survey of Cell Biology," Academic Press, Apr. 11, 1997, 175:145-146.

Kelm et al., "Sialic Acids in Molecular and Cellular Interactions," International Review of Cytology, 1997, 175:137-240.

Medina et al., "N-acetylgalactosamine-functionalized dendrimers as hepatic cancer cell-targeted carriers," Biomaterials, Jun. 2011, 32(17):4118-4129.

Prakash et al., "Solid-phase synthesis of 5'-triantennary N-acetylgalactosamine conjugated antisense oligonucleotides using phosphoramidite chemistry," Bioorg Med Chem Lett., 2015, 25(19):4127-4130.

Tomabechi et al., "Chemo-enzymatic synthesis of glycosylated insulin using a GlcNAc tag" Bioorg Med Chem., Feb. 2010, 18(3):1259-1264.

Uhlmann et al., "Recent Advances in the Medicinal Chemistry of Antisense Oligonucleotides," Curr. Opinion in Drug Development, 2000, 3(2):293-213.

Vester et al., "Chemically modified oligonucleotides with efficient Rnase H response," Bioorg. Med. Chem. Lett., 2008, 18:2296-2300.

* cited by examiner

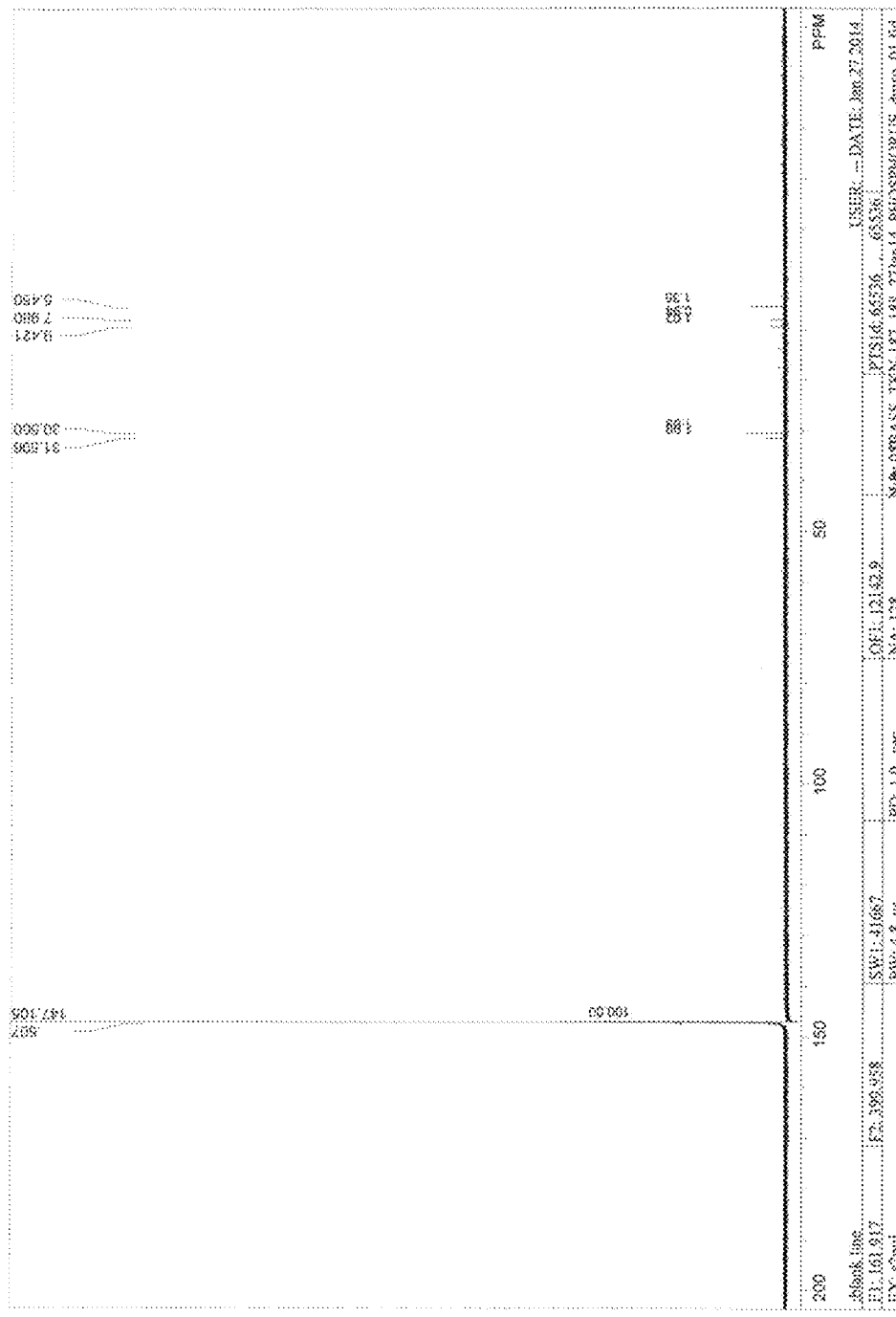
Figure 3a) $^{31}$P-NMR

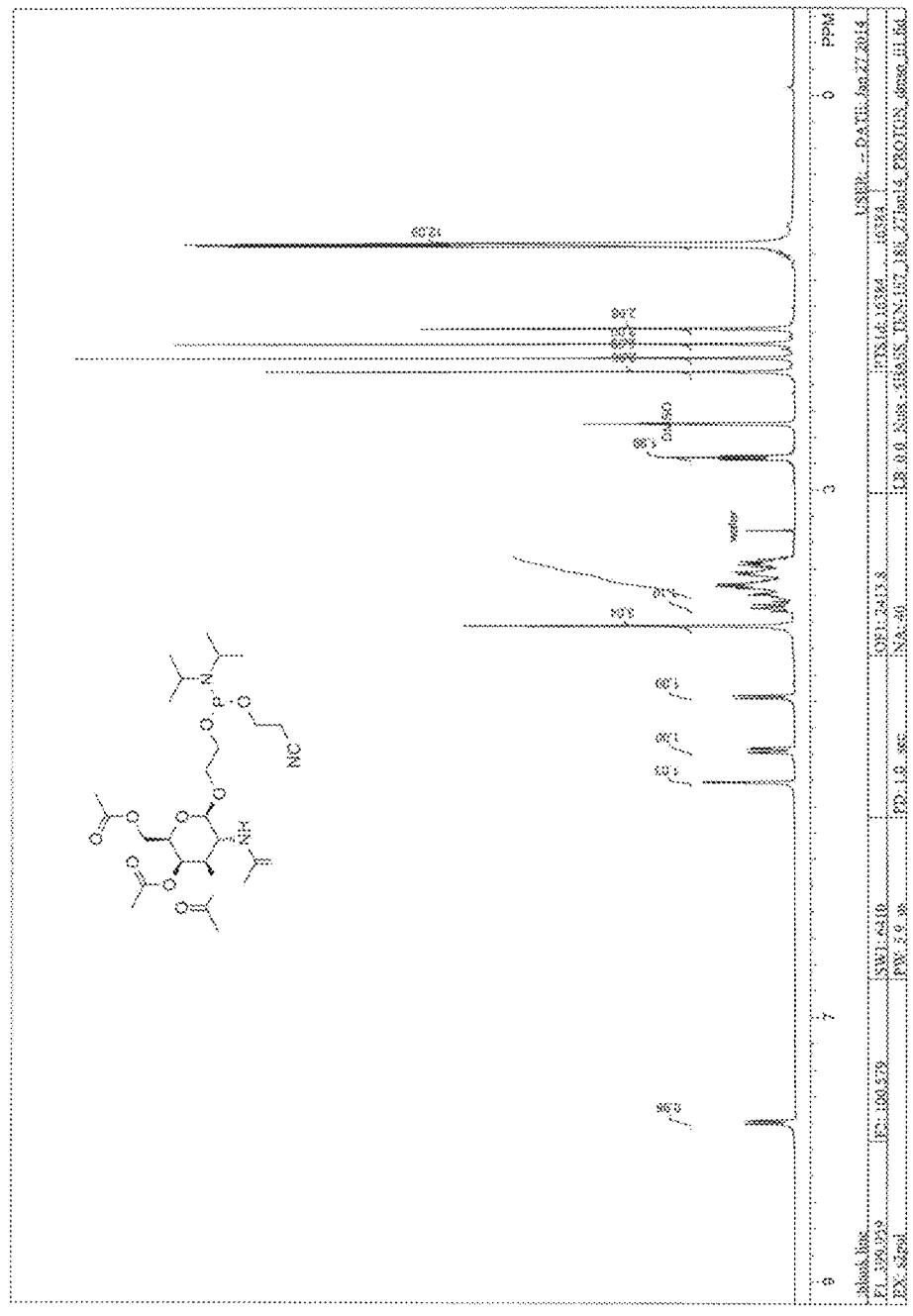
Figure 3b) ¹H-NMR

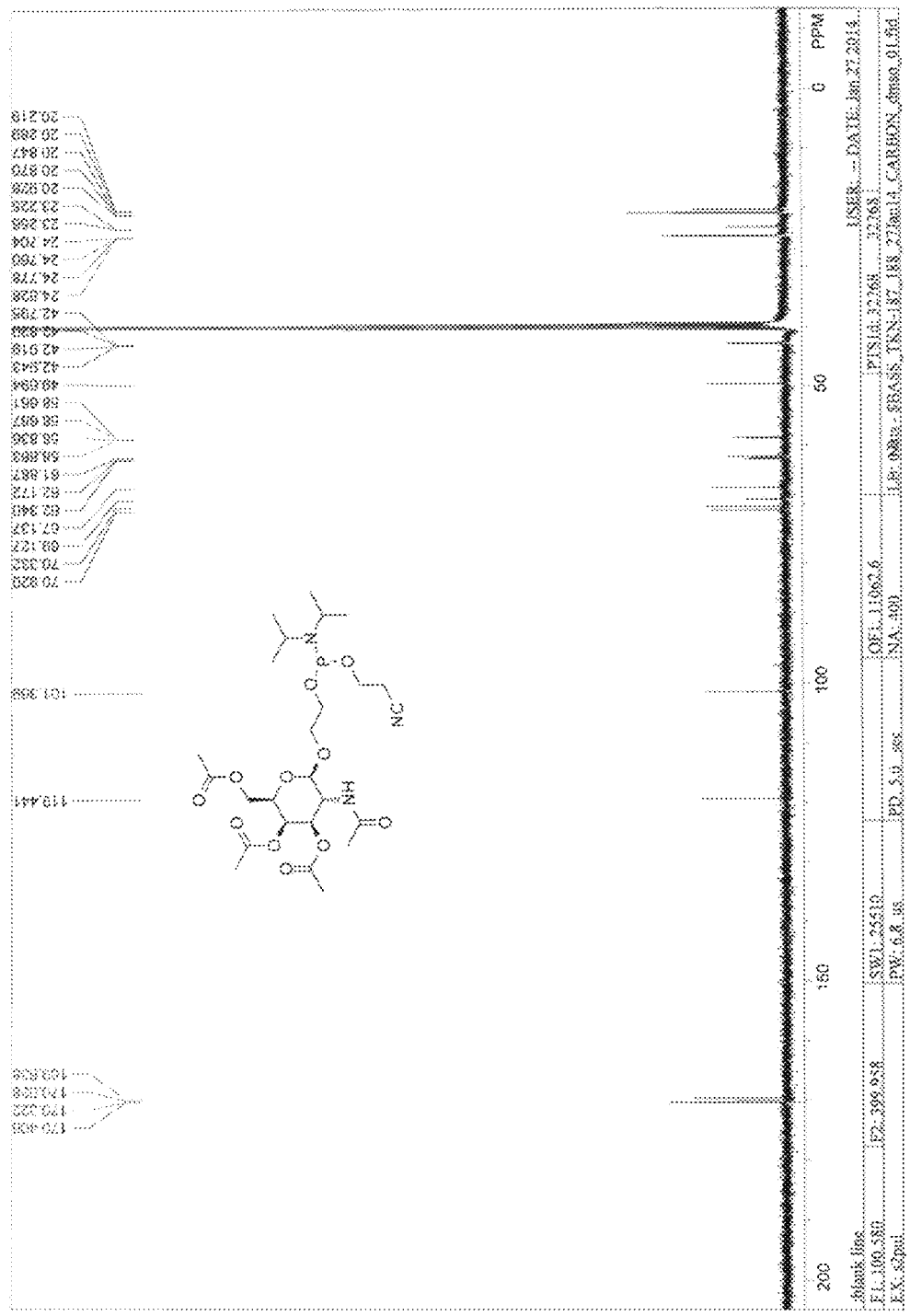
Figure 3c) 13C-NMR

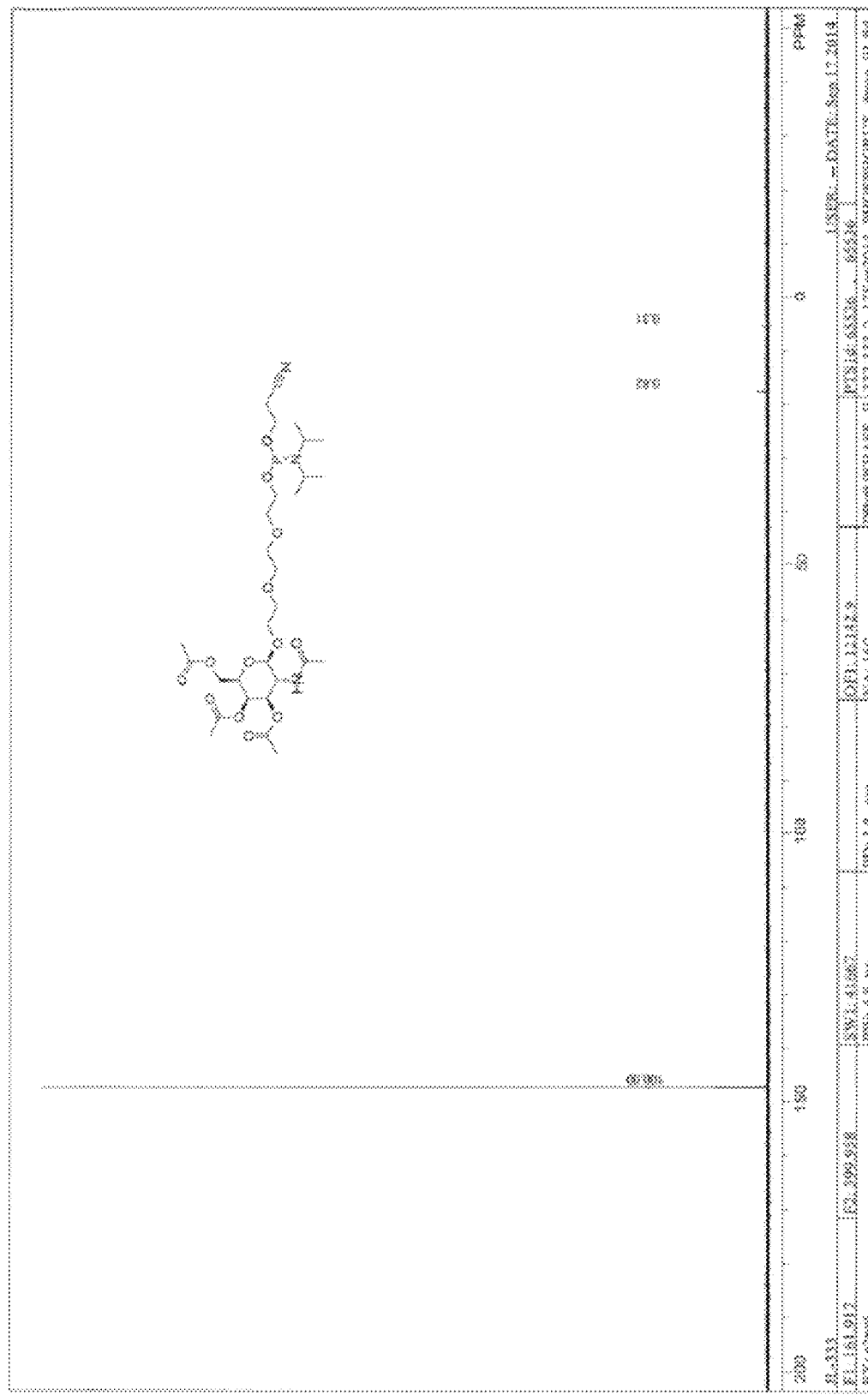
Figure 3d) ³¹P-NMR

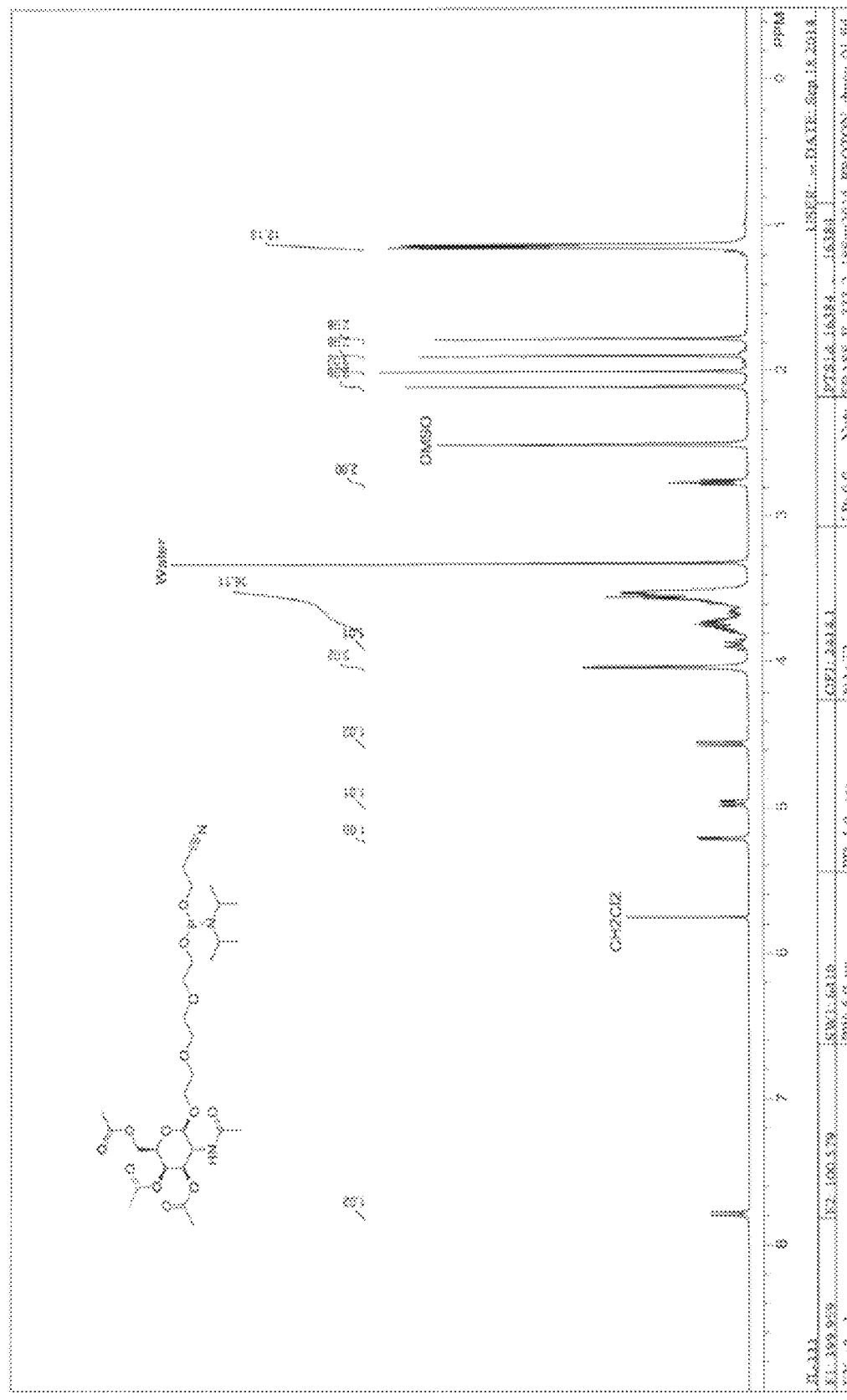
Figure 3e $^1$H-NMR

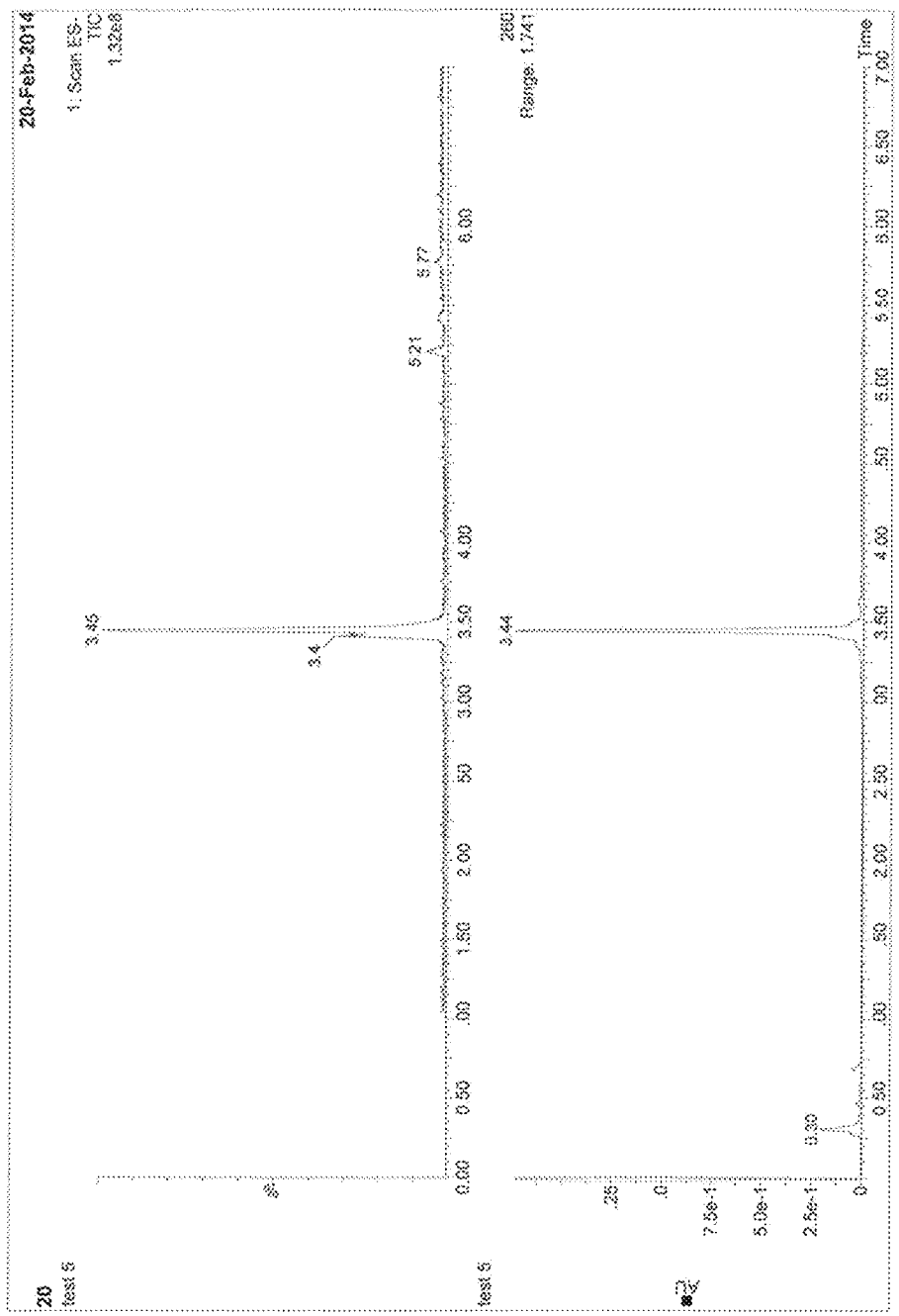
Figure 4a) UPLC

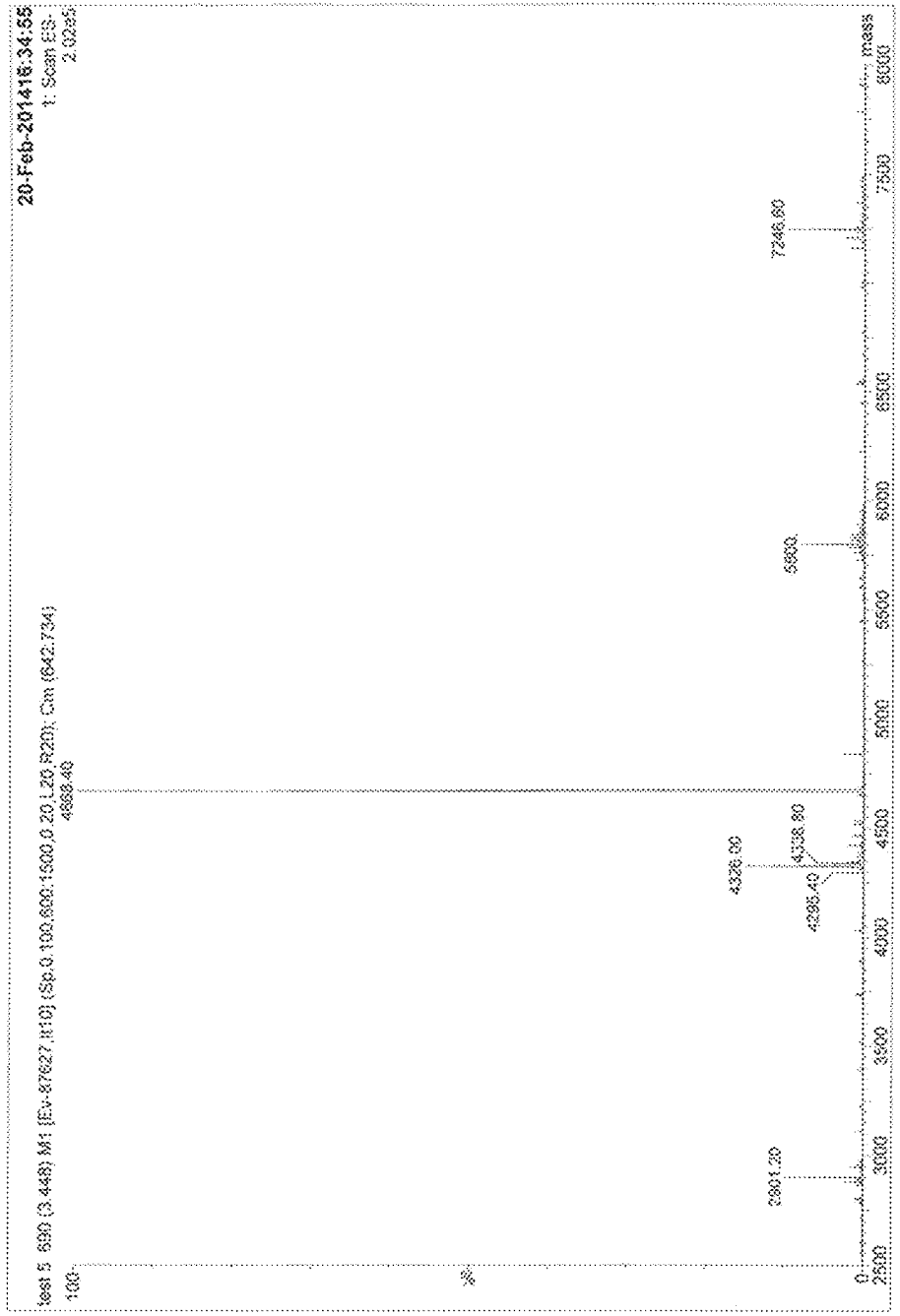
Figure 4b) ESI-MS (A)

(B)

(C)

(D)

Figure 6
(A)
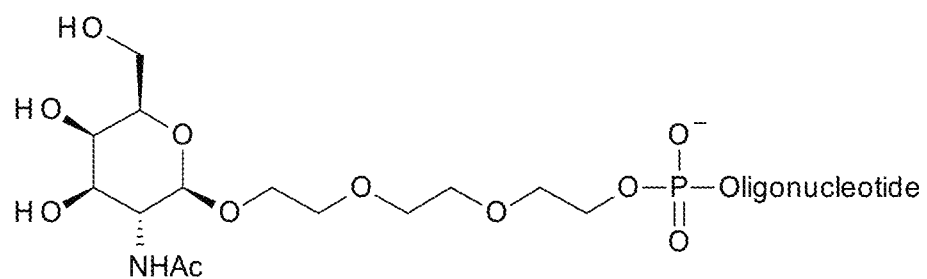
(B)
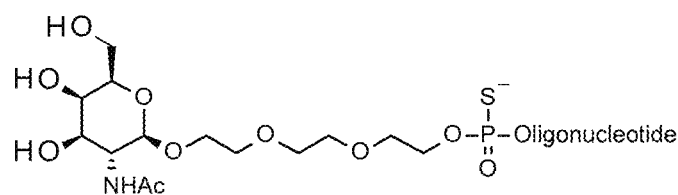
(C)
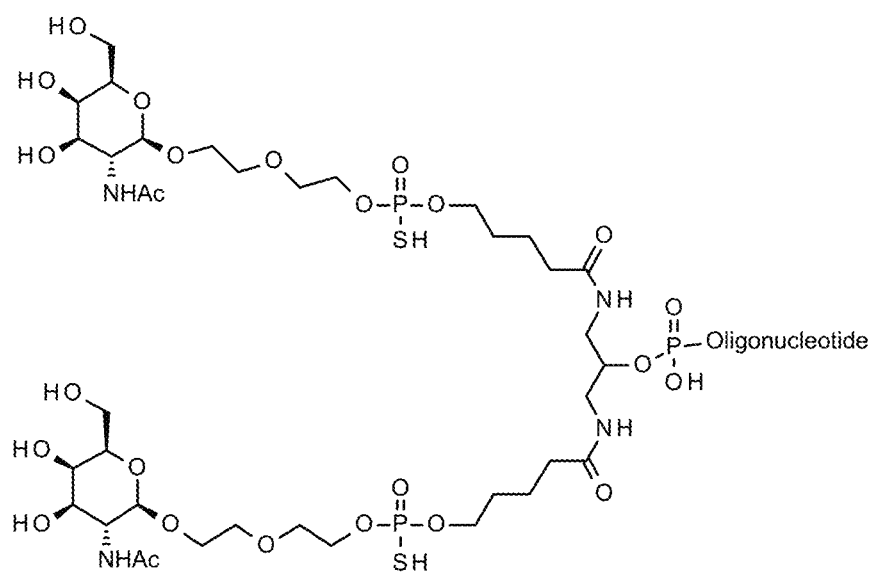

Figure 6 continued
(D)
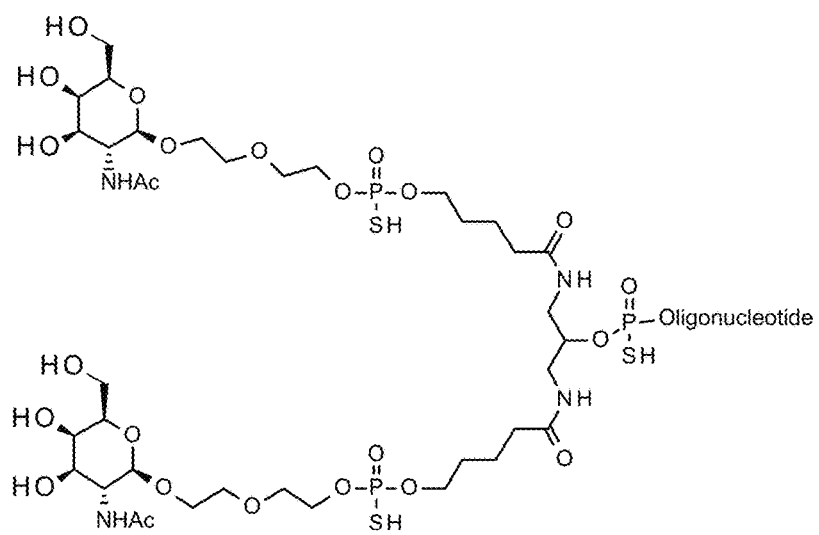
(E)
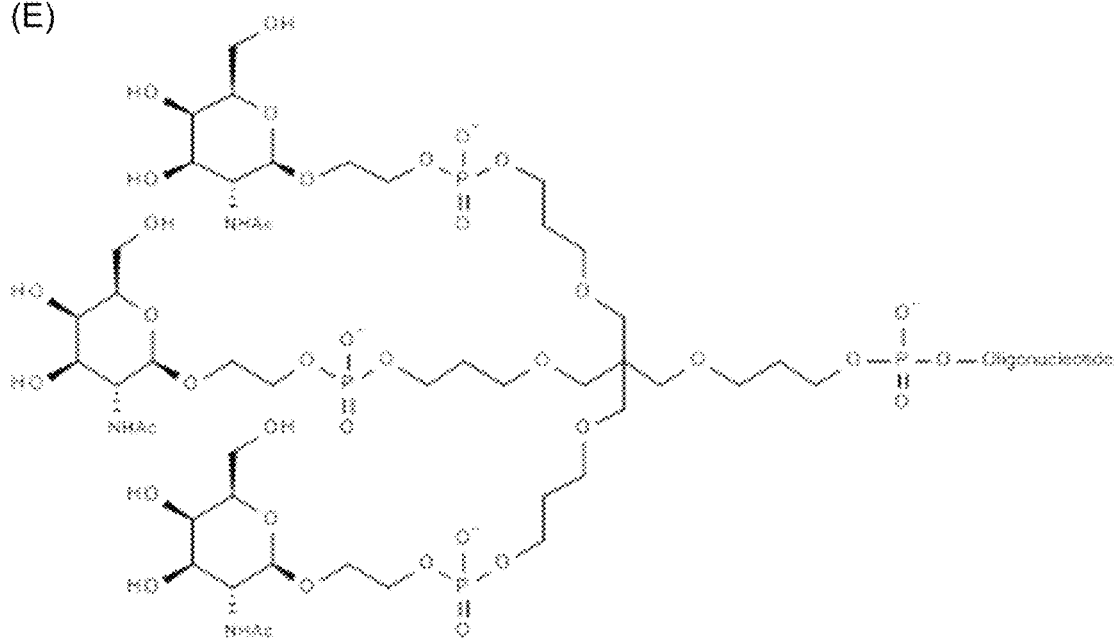

Figure 6 continued
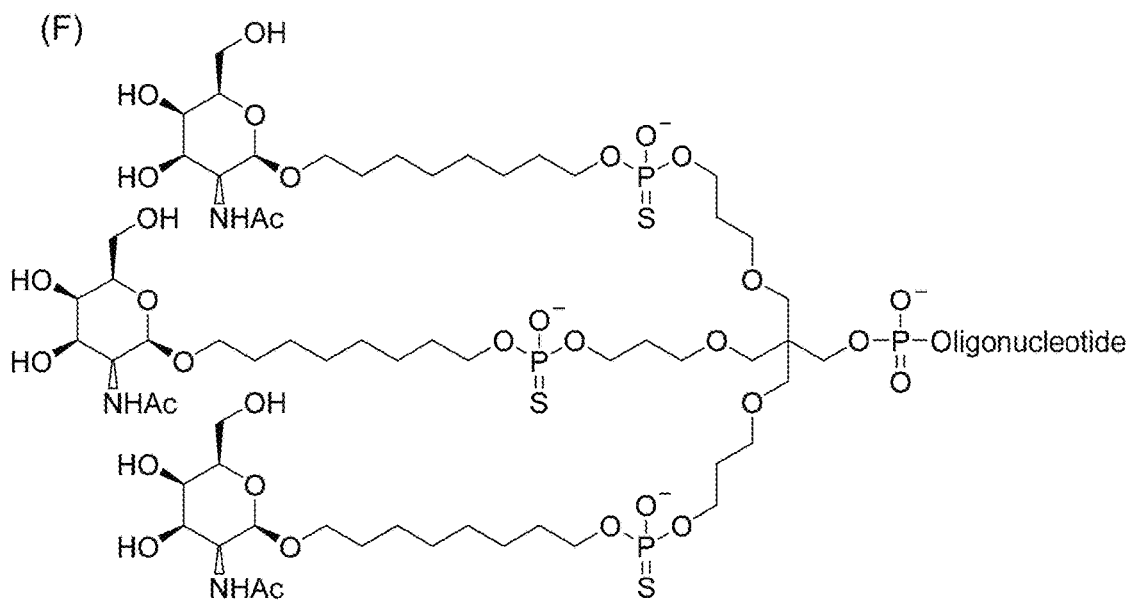
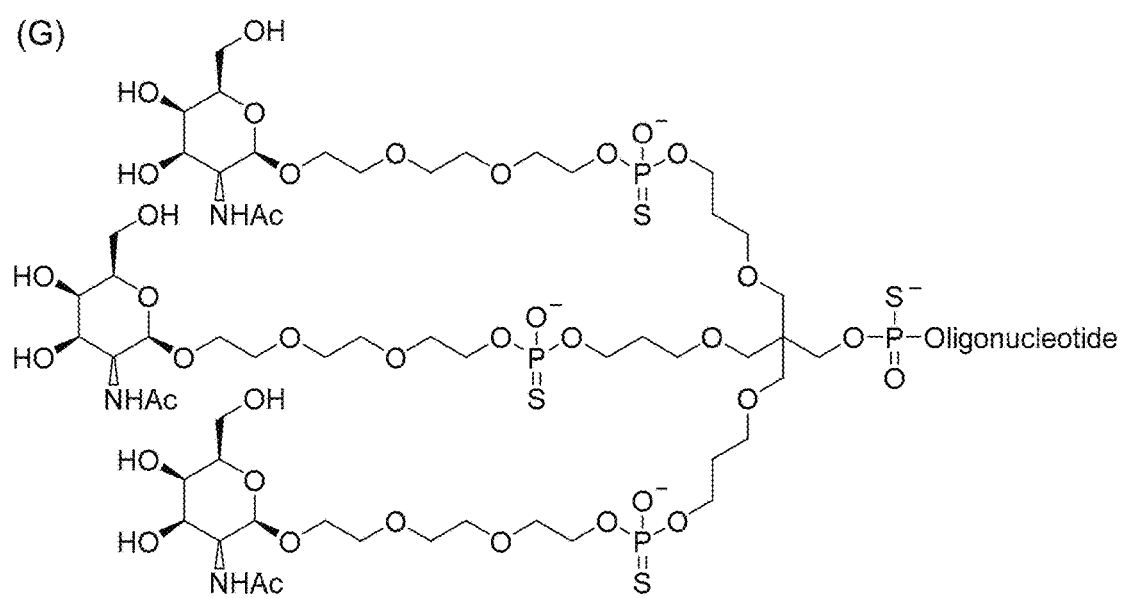

Figure 6 continued
(H)
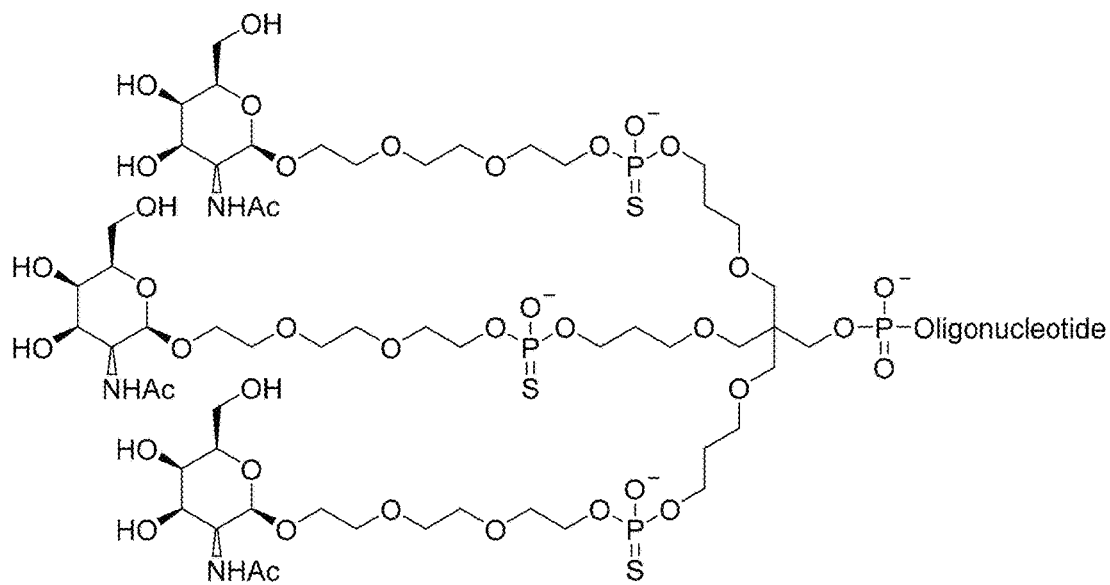
(I)
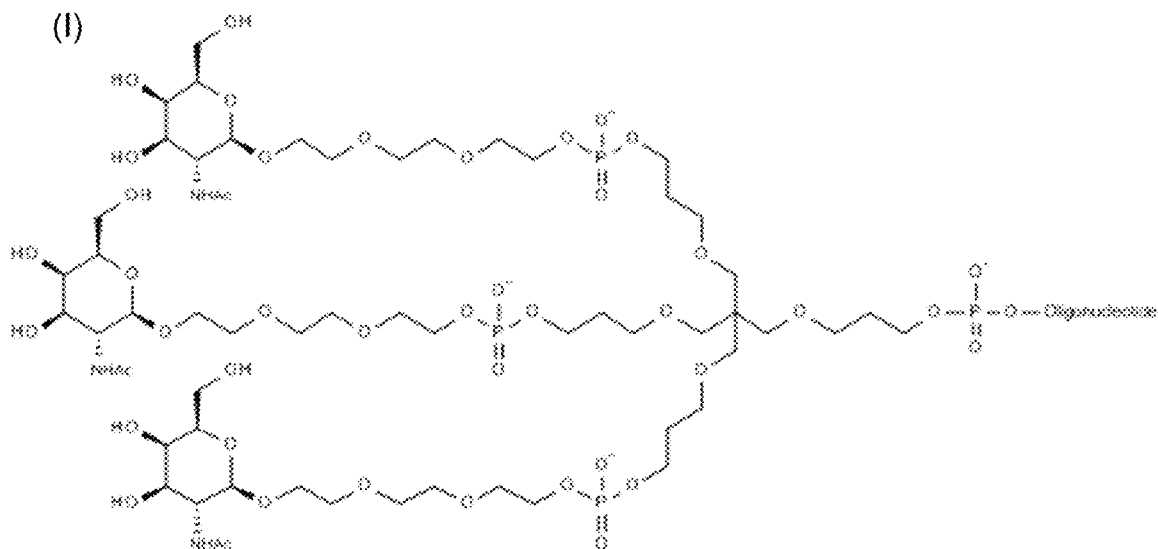

(N)

Figure 7
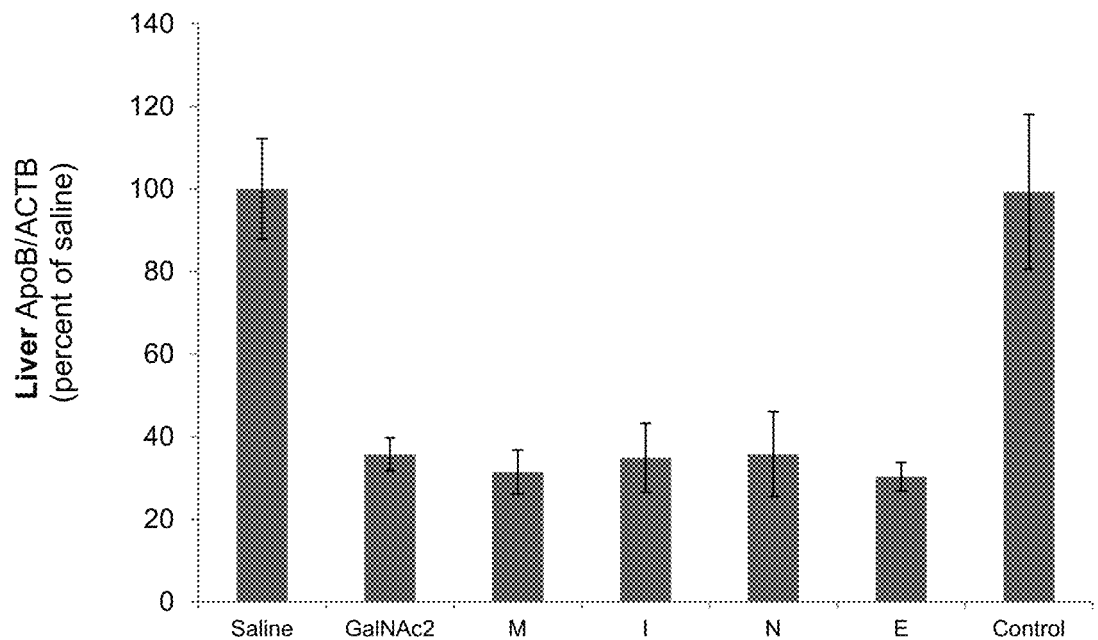
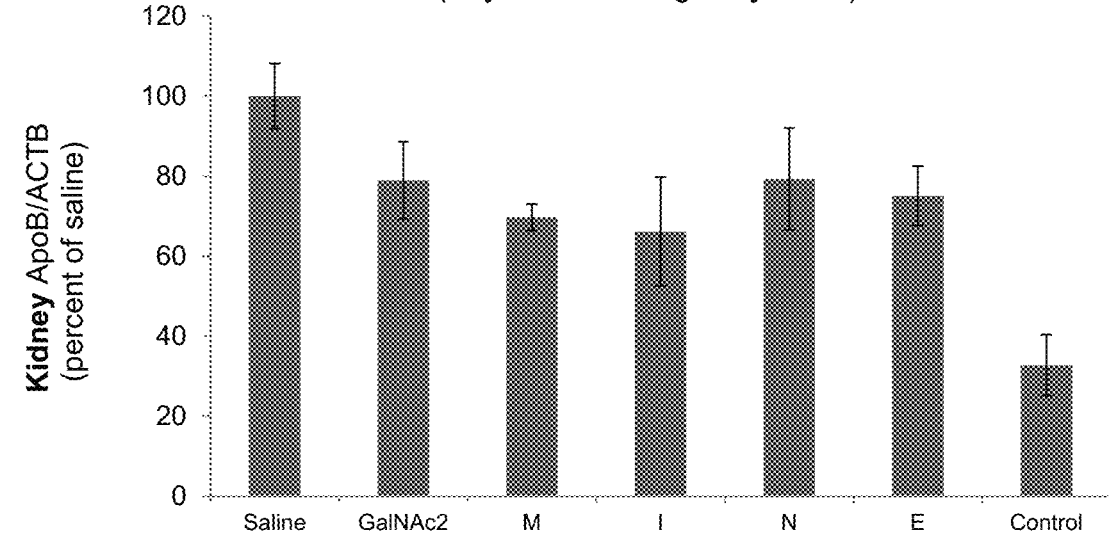

GALNAC PHOSPHORAMIDITES, NUCLEIC ACID CONJUGATES THEREOF AND THEIR USE

CLAIM OF PRIORITY

This application is divisional under 35 U.S.C. § 120 of application Ser. No. 15/517,685 filed Apr. 7, 2017 which is a national stage application under 35 U.S.C. § 371 of PCT Application No. PCT/EP2015/073331 filed Oct. 9, 2015 which claims priority to European Patent Application No. EP14188444.5 filed Oct. 10, 2014 and, European Patent Application No. 15181807.7 filed Aug. 20, 2015, of which each of these applications are hereby incorporated by reference in their entirety.

FIELD OF THE INVENTION

This invention generally relates to the field of phosphoramidite derivatives. In particular, the invention relates to N-Acetylgalactosamine phosphoramidite molecules and to conjugates of nucleic acid molecules with N-Acetylgalactosamine containing molecules. Also provided are methods for preparation of these molecules and possible uses thereof, in particular in medicine.

BACKGROUND OF THE INVENTION

In recent years, approaches have been developed to use nucleic acid molecules in therapy. To favorably influence pharmaceutically relevant properties, the nucleic acid molecules have been conjugated to certain ligands such as peptides, lipids, sterols, and carbohydrates. Nucleic acid conjugates have been extensively evaluated for use in siRNAs, where they are considered essential in order to obtain sufficient in vivo potency. For example, by attachment of a conjugate moiety containing terminal galactose or a derivative thereof to the nucleic acid, thereby targeting the nucleic acid molecule to hepatocytes via binding to the asialoglycoprotein receptor (ASGPR), see for example WO2009/073809, WO2011/104169 and WO2012/083046.

EP2796150 describes hybrid conjugates which comprise a hydrophilic material and hydrophobic material bonded to both ends of an siRNA or an oligonucleotide. In one example the hydrophilic material is a specific GalNAc phosphoramidite to be coupled to a pegylated siRNA molecule.

U.S. Pat. No. 6,057,431 relates to phosphoamidite derivatives having a monosaccharide or a derivative thereof at their terminals, in particular to oligonucleotide derivatives in which oligonucleotides are introduced into said phosphoamidite derivatives.

Dubber and Frechet 2003 Bioconjugate Chem. Vol. 14 page 239 describes synthesis of a trivalent galactose cluster using a DNA synthesizer for coupling phosphoramidite derivatives but without producing an oligonucleotide. WO2002/094185 relates to various conjugates and compositions for cellular delivery.

WO2014/118267 and WO2014/179620 relates to antisense oligonucleotide carbohydrate conjugates, in particular comprising an antisense oligomer and an asialoglycoprotein receptor targeting conjugate moiety, such as a GalNAc conjugate moiety.

However, one major drawback of currently available carbohydrate conjugates is their complex synthesis, which comprises more than ten individual synthesis steps. For each desired conjugate, a complex and specific synthesis protocol has to be set up.

OBJECTIVE OF THE INVENTION

It was an object of the invention to provide novel conjugate molecules which are easy to produce.

Surprisingly, the present inventors have now discovered that the synthesis of carbohydrate nucleic acid conjugates is greatly facilitated by using novel GalNAc phosphoramidites. In particular, their use leads to significantly fewer operations in the manufacture of the conjugates as compared to currently available protocols.

Moreover, due to the compatibility of the GalNAc phosphoramidites of the invention with commercially available branching molecules as well as with commercially available spacers, the invention provides a great flexibility in the synthesis of GalNAc-nucleic acid conjugates. Suitable GalNAc phosphoramidites (with desired linker), nucleic acids and, if desired, brancher molecules and/or spacer molecules can be combined according to specific needs. For example, the individual building blocks can be chosen such that binding of the final conjugate is, e.g. with regard to the spacing between the GalNAc molecules, ideally suited for binding to a specific cell receptor, e.g. the asialoglycoprotein receptor (ASGPR).

In addition, the novel GalNAc phosphoramidites may be used in solid phase synthesis together with e.g. LNA and DNA phosphoramidites. This allows assembly of the nucleic acid carbohydrate conjugate immediately after the nucleic acid molecule synthesis, while the nucleic acid is still attached to the solid support.

SUMMARY OF THE INVENTION

In one aspect, the present invention relates to N-acetylgalactosamine (GalNAc) phosphoramidites.

In a further aspect, the present invention relates to GalNAc-nucleic acid conjugates, i.e. molecules comprising a one or more (e.g. a plurality of) GalNAc moieties which have been covalently bound to a nucleic acid molecule using a linker and phosphoramidite chemistry.

Preferably, the GalNAc moieties have been covalently bound to a branching molecule, optionally via a spacer molecule, thereby generating a cluster comprising 2, 3 or more GalNAc moieties.

In a further aspect, the present invention relates to a manufacturing process of GalNAc phosphoramidites.

In yet a further aspect, the present invention relates to a manufacturing process of GalNAc-nucleic acid conjugates.

In yet a further aspect, the invention relates to various uses of the described novel GalNAc phosphoramidites and the GalNAc-nucleic acid conjugates.

According to a further aspect, the invention provides medical uses of the compounds according to the invention, in particular of GalNAc-nucleic acid conjugates.

Also provided are methods of treatment comprising administration of compounds according to the invention in a therapeutically or diagnostically effective amount, in particular of GalNAc-nucleic acid conjugates, to a subject in need thereof.

a) Flow chart of the synthesis of monovalent, divalent and trivalent GalNAc-nucleic acid conjugates using GalNAc phosphoramidites either alone (a) or in combination with a doubler (b) or trebler branching molecule (c).

b) Flow chart of the synthesis of monovalent (a), divalent (b) and trivalent (c) GalNAc-nucleic acid conjugate using GalNAc phosphoramidites and a spacer and for divalent and trivalent molecules a doubler or trebler branching molecule.

Figure 2A:
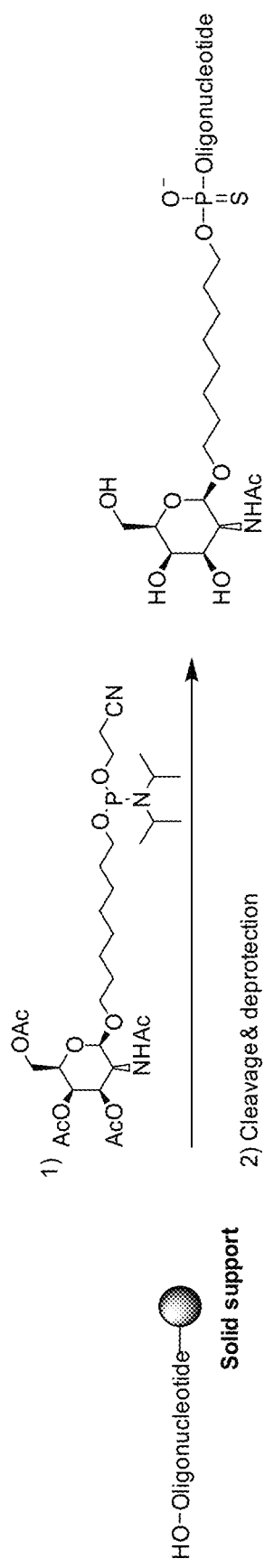
Figure 2B:
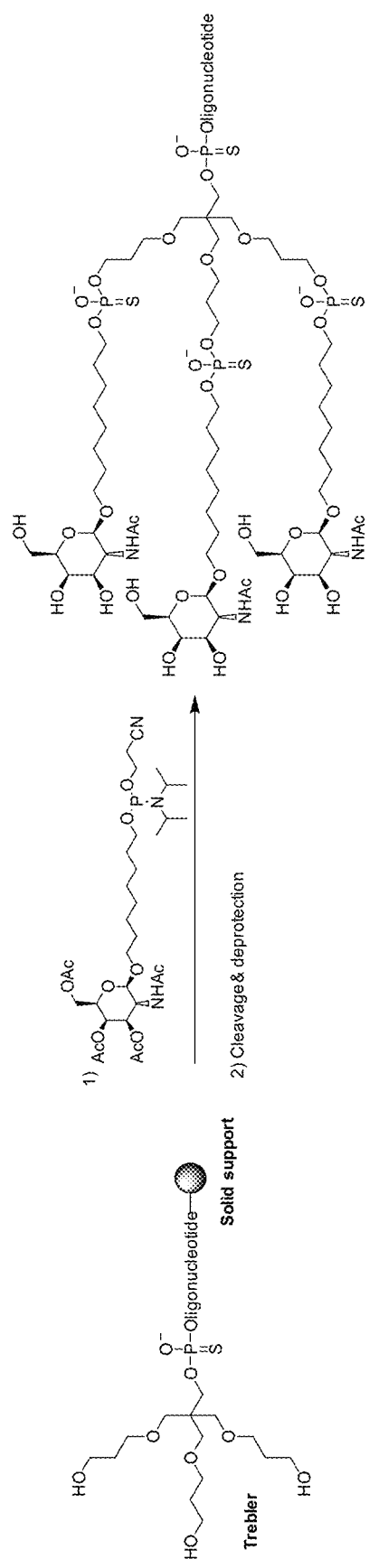
Figure 2C:
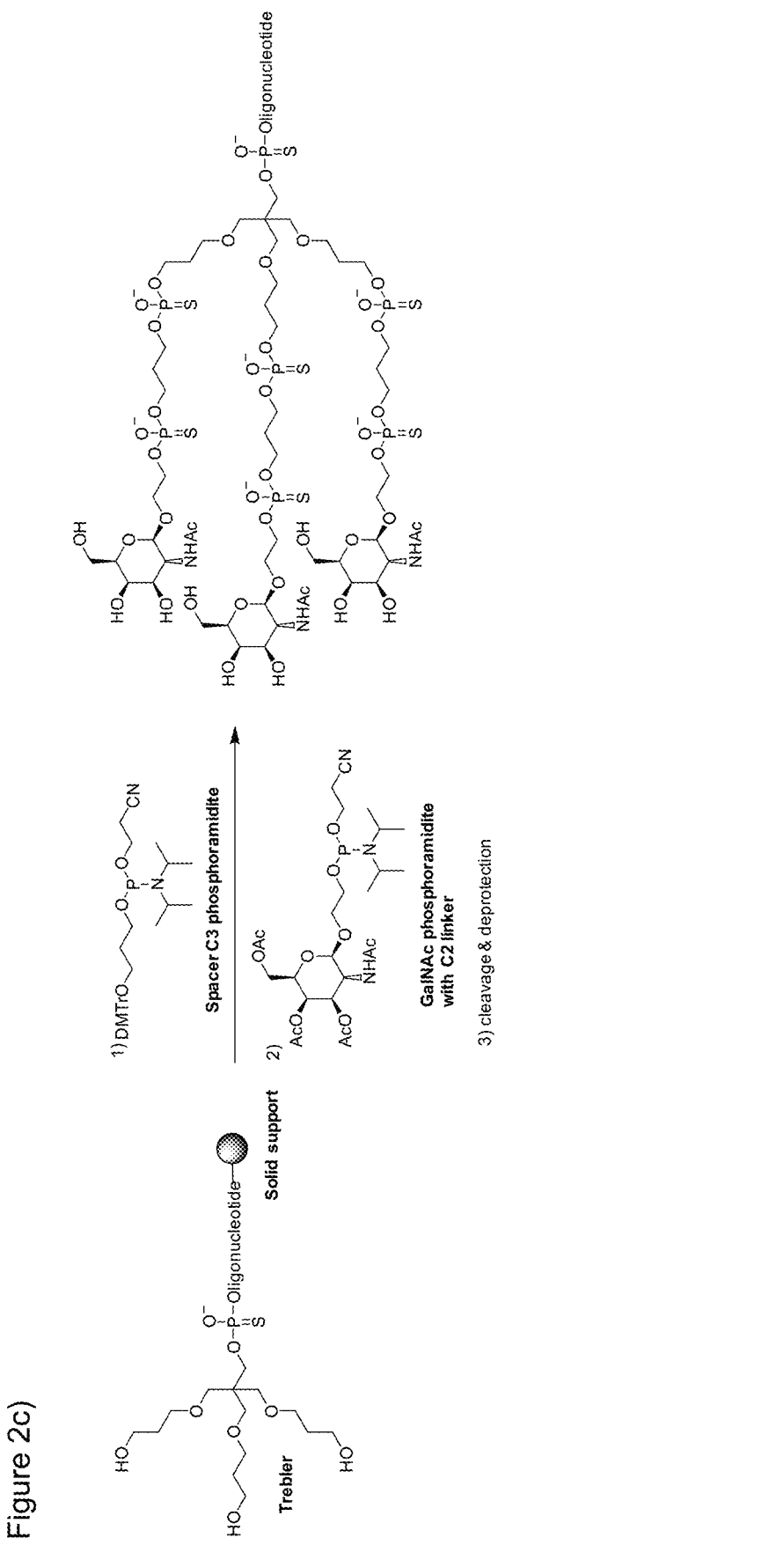

FIGS. 2a-c: Synthesis examples of GalNAc-nucleic acid conjugates.

a) Example of coupling of GalNAc phosphoramidite directly to the 5'-end of an oligonucleotide as part of the sequential synthesis on solid support.

b) Example of coupling of GalNAc phosphoramidite directly on to a trebler and subsequent cleavage and deprotection to give an oligonucleotide GalNAc cluster construct.

c) Example of coupling sequentially a spacer and a GalNAc phosphoramidite on to a trebler and subsequent cleavage and deprotection to give an oligonucleotide GalNAc cluster construct.

FIGS. 3a-e: NMR data on GalNAc phosphoramidite.
a) $^{31}$P-NMR
b) $^{1}$H-NMR
c) $^{13}$C-NMR
d) $^{31}$P-NMR TEG beta-GalNAc phosphoramidite
e) $^{1}$H-NMR TEG beta-GalNAc phosphoramidite FIGS. 4a-b: Data on monovalent GalNAc-oligonucleotide conjugate.
a) Retention time (UPLC)
b) Molecular weight as determined by ESI-MS FIG. 5: Exemplary GalNAc phosphoramidites
(A) to (D) represent GalNAc phosphoramidites with different linkers.

Figure 6:
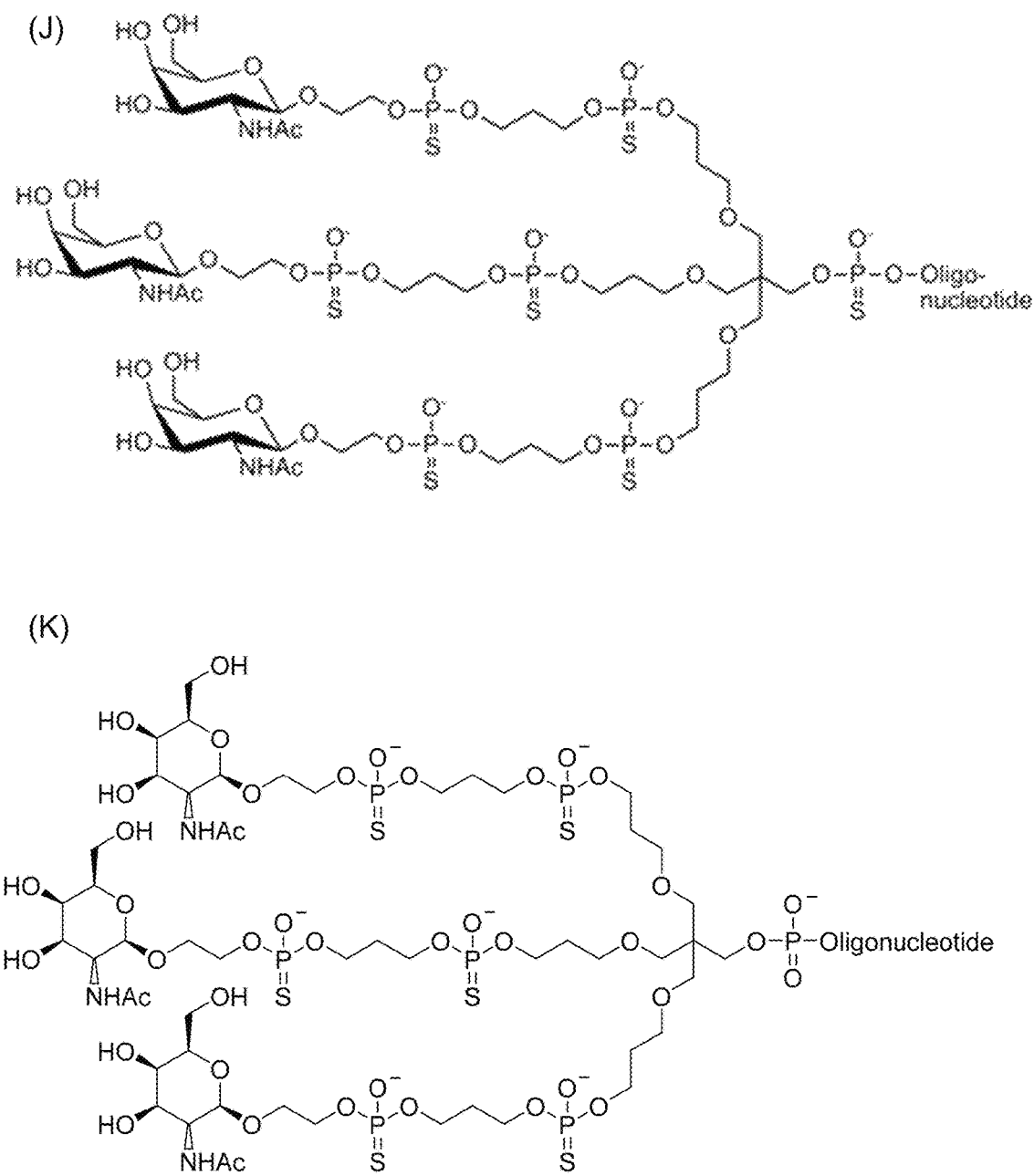
Figure 6:
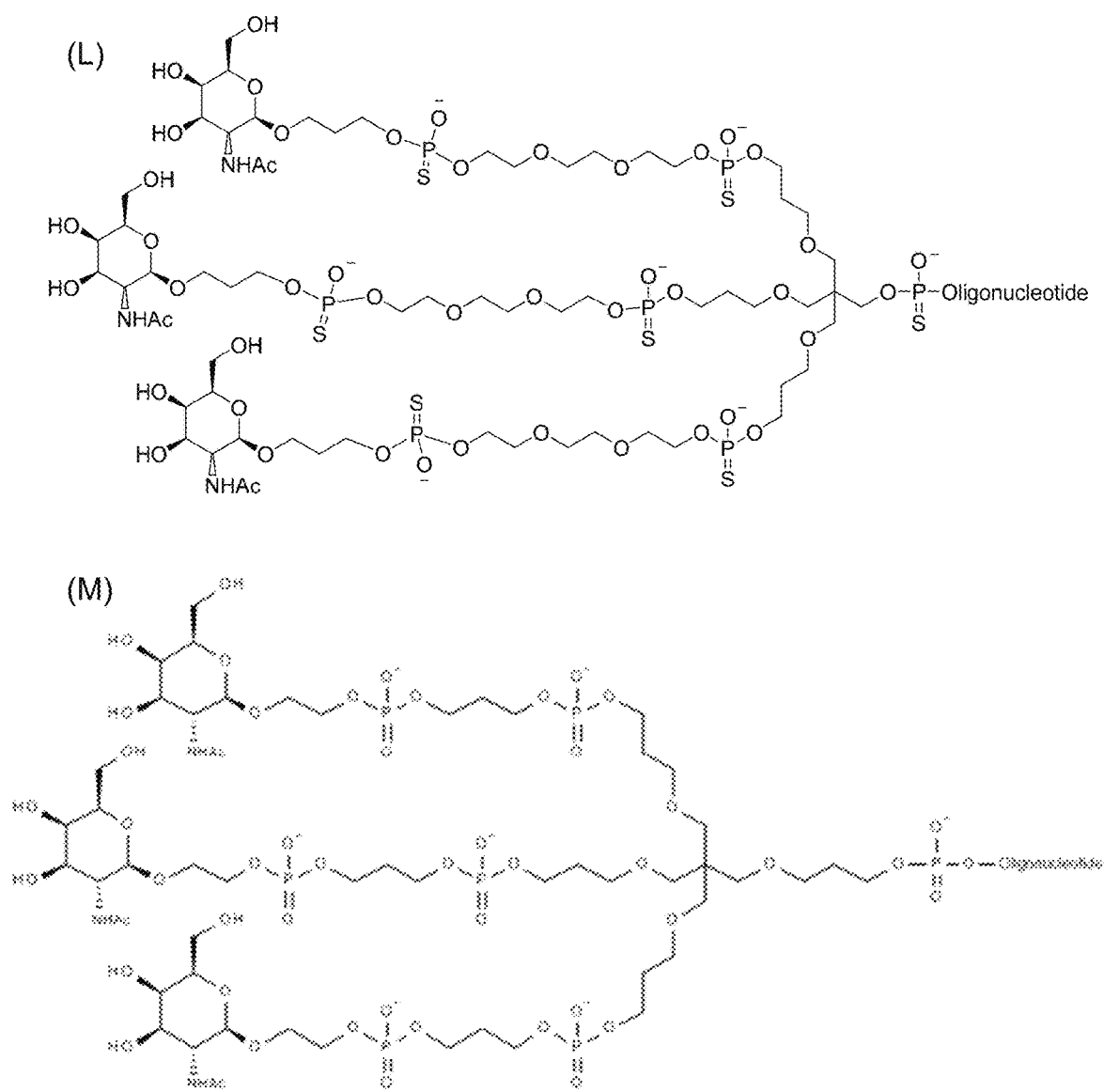
Figure 6:
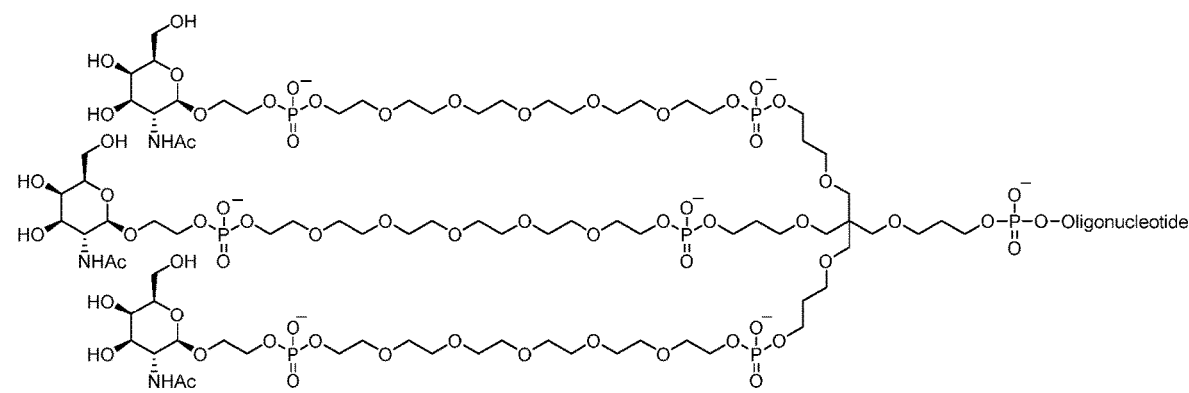

FIG. 6: Exemplary GalNAc-nucleic acid conjugate
(A) and (B) monovalent GalNAc-nucleic acid conjugate with a linker length of 8 atoms.

(C) and (D) are divalent GalNAc-nucleic acid conjugates with a linker length is 5 atoms. The length of the contiguous chain starting with the first atom of linker L in $R^{1, 2 \text{ or } 3}$ and ending with the attachment point in formula (IV), is 15 atoms.

(E) is a trivalent GalNAc-nucleic acid conjugate composed of a GalNAc phosphoramidite, a brancher and an oligonucleotide, the linker length is 2 atoms. The length of the contiguous chain starting with the first atom of linker L in $R^{1, 2 \text{ or } 3}$ and ending with the attachment point in formula (IV), is 10 atoms.

(F) to (I) are trivalent GalNAc-nucleic acid conjugate composed of a GalNAc phosphoramidite, a brancher and an oligonucleotide, the linker length is 8. The length of the contiguous chain starting with the first atom of linker L in $R^{1, 2 \text{ or } 3}$ and ending with the attachment point in formula (IV), is 16 atoms.

(J), (K) and (M) are trivalent GalNAc-nucleic acid conjugates composed of a GalNAc phosphoramidite, a spacer, a brancher and an oligonucleotide. The linker length is 2 and the spacer length is 3. The length of the contiguous chain starting with the first atom of linker L in $R^{1, 2 \text{ or } 3}$ and ending with the attachment point in formula (IV), is 16 atoms.

(L) is a trivalent GalNAc-nucleic acid conjugates composed of a GalNAc phosphoramidite, a spacer, a brancher and an oligonucleotide. The linker length is 3 and the spacer length is 8. The length of the contiguous chain starting with the first atom of linker L in $R^{1, 2 \text{ or } 3}$ and ending with the attachment point in formula (IV), is 22 atoms.

(N) is a trivalent GalNAc-nucleic acid conjugates composed of a GalNAc phosphoramidite, a spacer, a brancher and an oligonucleotide. The linker length is 2 and the spacer length is 17. The length of the contiguous chain starting with the first atom of linker L in $R^{1, 2 \text{ or } 3}$ and ending with the attachment point in formula (IV), is 30 atoms.

FIG. 7 ApoB mRNA knock down
A) shows mRNA knock down by the test compounds in the liver 10 days after a single injection of 25 mg/kg
B) shows mRNA knock down by the test compounds in the kidney 10 days after a single injection of 25 mg/kg.

Figure 8:
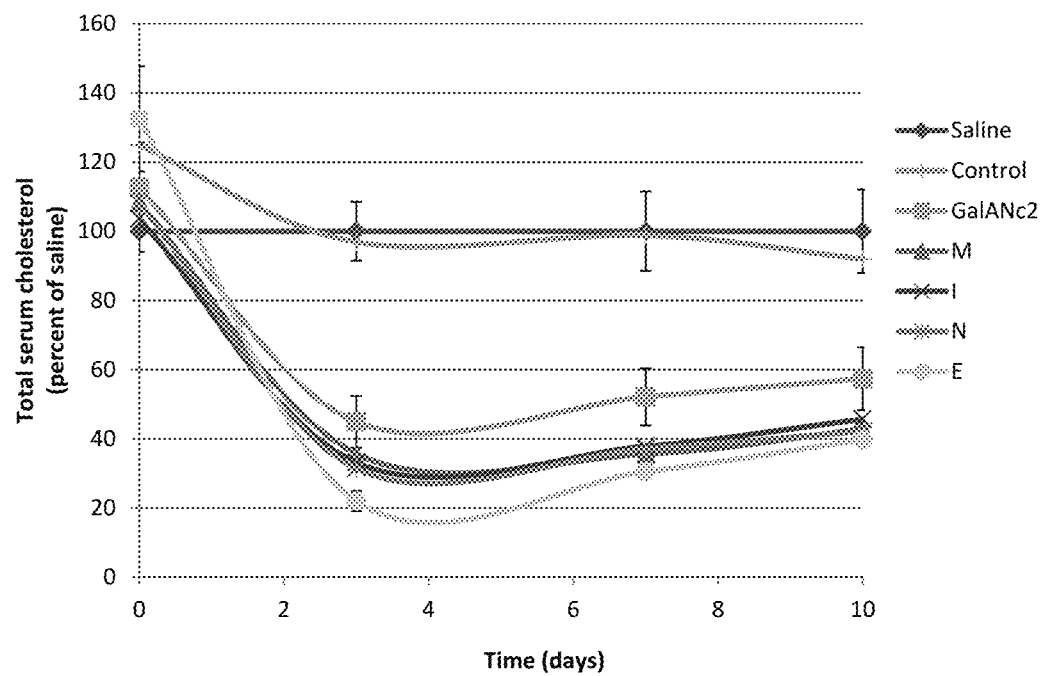

FIG. 8 Down regulation of total cholesterol in serum
The figure shows down regulation of serum cholesterol measured at day 3, 7 and 10 after a single injection of 25 mg/kg of the compound.

DETAILED DESCRIPTION OF THE INVENTION

GalNAc Phosphoramidites

In one aspect, the present invention relates to novel N-acetylgalactosamine (GalNAc) phosphoramidites. Accordingly, the invention provides a compound having the general formula (I)

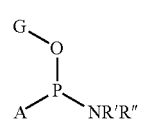

wherein
NR'R" is a secondary amino group, wherein R' and R" are independently selected from $C_1$-$C_6$-alkyl or R' and R" together form a five- or six-membered ring, which may be substituted and which may contain one further heteroatom selected from N and O;

A is a $C_1$-$C_6$-alkyl group or a protected hydroxy- or thio-group; and

G is represented by general formula (II)

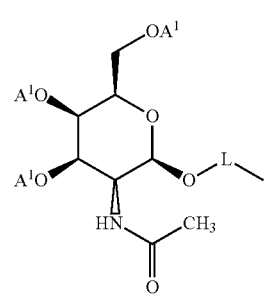

wherein $A^1$ is a suitable hydroxyl protecting group, which may be the same or different at each occurrence; and L is a linker group with a chain length of from 2-30 carbon atoms, wherein one or more of the carbon atoms in the chain may each independently be replaced by —NHCO—, —CONH— and/or a heteroatom, particularly O. In some embodiments the linker group L is selected from the group consisting of $C_2$-$C_{30}$-alkenylene, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$CH$_2$OCH$_2$CH$_2$—, —CH$_2$CH$_2$OCH$_2$CH$_2$OCH$_2$CH$_2$—, and —CH$_2$CH$_2$ $-(OCH_2CH_2)_2OCH_2CH_2-$, more preferably from $-(CH_2)_2-$, $-(CH_2)_3-$, and $-(CH_2)_8-$.

The GalNAc moiety can be either in the alpha or the beta configuration as indicated by the wavy line in formula II. In preferred embodiments the GalNAc moiety is in the beta configuration.

The term "GalNAc moiety" as used herein is the N-Acetylgalactosamine (GalNAc) part of a structure comprising GalNAc. For example in formula (II) the GalNAc moiety is the part of the molecule which does not constitute the L.

The term "GalNAc conjugate moiety" as used herein, refers to a molecule comprising at least one GalNAc moiety and which can be conjugated unto a drug in particular a nucleic acid. Preferably the GalNAc conjugate moiety has affinity towards the asialoglycoprotein receptor.

The term "phosphoramidite" as used herein means any compound containing a phosphor atom in oxidation state III which is bound covalently to at least one nitrogen atom. Preferred phophoramidites of the invention are compounds containing a phosphor atom in oxidation state III which is bound covalently to at least one nitrogen atom and two oxygen atoms. Alternative, phophoramidites of the invention are compounds containing a phosphor atom in oxidation state III which is bound covalently to at least one nitrogen atom and one oxygen atom and instead of a second oxygen has a sulphor atom or a $C_1$-$C_6$-alkyl group.

In certain embodiments, R' and R" of the secondary amino group $-NR'R"$ in formula (I) are independently selected from $C_1$-$C_6$-alkyl, in particular from methyl, ethyl, propyl, isopropyl, n-butyl, sec-butyl, t-butyl, n-pentyl and n-hexyl. In particular embodiments, R' is identical to R", and $-NR'R"$ then preferably is selected from the group consisting of dimethylamino, diethylamino, diisopropylamino, and dibutylamino. In a preferred embodiment R' and R" each are isopropyl.

In other embodiments, R' and R" together form a five- or six-membered ring, which may be substituted and which may contain one further heteroatom selected from N and O. In some embodiments, R' and R" form an unsubstituted five-membered ring, in other embodiments, they form an unsubstituted six-membered ring. In still further embodiments, the five-membered or six-membered ring is substituted at one or more carbon atoms. For example, the ring may be substituted at one, two, three or four carbon atoms, preferably at one or two carbon atoms. Preferred substituents are methyl and ethyl. In particular, the ring is selected from the group consisting of pyrrolidino, piperidino, 2,6-dimethylpiperidino, morpholino, imidazolyl and 4-methylimidazolyl.

The moiety A in formula (I) is, according to some embodiments, selected from $C_1$-$C_6$-alkyl, in particular from the group consisting of methyl and ethyl.

In further embodiments, A is a protected hydroxy group ($-OH$) or a protected thio group ($-SH$). Exemplary non-limited protected hydroxy groups are either groups, exemplary non-limited protected thio groups are thioether groups. In particular, the protected $-OH$ or $-SH$ group represented by A is selected from the group consisting of 2-cyanoethoxy, 2-cyanoethylthio, methoxy, ethoxy, S-isobutanoyl-2-(2-mercapto-ethoxy)ethoxy, S-pivaloyl-2-(2-mercapto-ethoxy) ethoxy, and S-pivaloyl-2-mercaptoethoxy. In a preferred embodiment A is a 2-cyanoethoxy group.

The linker group L is selected according to the desired application of the GalNAc phosphoramidite. In some embodiments, one or more of the carbon atoms in the chain may each independently be replaced by $-NH-CO-$, $-CO-NH-$ and/or a heteroatom, particularly O.

The number of replacements should be adapted such that the total length of the linker does not exceed 30 atoms after replacements and maintaining at least one neighbouring atom to the replacements as carbon atoms in the case of $-NH-CO-$, $-CO-NH$ and at least 2 neighbouring carbon atoms in the case of heteroatom replacements. In some embodiments the number of replacements is less than 5 and the neighbouring atoms to the replacements are carbon atoms. In some embodiments no more than one or two replacements are made in the chain and the neighbouring atoms to the replacements are carbon atoms. For example, the linker between the GalNAc and the phosphoramidite may be derived from a simple diol.

In principle, any symmetrical or unsymmetrical diol could be used as a linker in the GalNAc phosphoramidite of the invention, provided it contains no other nucleophilic groups. In some embodiments, carbon atoms in the chain are replaced by oxygen atoms in order to form an array of $-(OCH_2CH_2)$-groups.

In certain embodiments, L is selected from the group consisting of $C_2$-$C_{30}$-alkylene, $C_2$-$C_{30}$-alkenylene, and $-CH_2CH_2-(OCH_2CH_2)_{0-8}-OCH_2CH_2-$. More specifically, the linker group L may be selected from $C_2$-$C_{20}$-alkylene, $C_2$-$C_{20}$-alkenylene, $-CH_2CH_2-(OCH_2CH_2)_{0-6}-OCH_2CH_2-$, $CH_2CH_2-(OCH_2CH_2)_{0-3}-OCH_2CH_2-$, $CH_2CH_2-(OCH_2CH_2)_{0-4}-OCH_2CH_2-$, and $CH_2CH_2-(OCH_2CH_2)_{6-8}-OCH_2CH_2$. More specifically the alkylene is selected from $C_3$-$C_{19}$-alkylene, but not C alkylene or from $C_7$-$C_{19}$-alkylene. Even more specifically, the linker group L may be selected from the group consisting of $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-(CH_2)_{11}-$, $-(CH_2)_{12}-$, $-CH_2CH_2OCH_2CH_2-$, $-CH_2CH_2OCH_2CH_2OCH_2CH_2-$, and $-CH_2CH_2(OCH_2CH_2)_2OCH_2CH_2-$. In preferred embodiments, the linker L is $-(CH_2)_2-$ or $-(CH_2)_3-$. In other preferred embodiments, the linker L is $-(CH_2)-$ or $-CH_2CH_2OCH_2CH_2OCH_2CH_2-$. In another preferred embodiment, the linker L is $-(CH_2)_5$ or $-CH_2CH_2OCH_2CH_2-$. In another preferred embodiment, the linker L is $-CH_2CH_2OCH_2CH_2-$, $-CH_2CH_2OCH_2CH_2OCH_2CH_2-$, or $-CH_2CH_2(OCH_2CH_2)_2OCH_2CH_2-$.

For $A^1$, a lot of different protecting groups are available. The skilled person will know how to choose a protecting group that is stable to the reaction conditions used in the process for preparing the phosphoramidite, and the coupling and oxidation step of the oligonucleotide synthesis process. As example for a suitable hydroxyl protecting group A according to formula (II), acyl groups and silyl groups may be mentioned. Preferably, the protecting group A is selected from the group consisting of acetyl, benzoyl, phenoxyacetyl, dimethoxytrityl (DMT), pivaloyl, isobutyryl, t-butyldimethylsilyl, t-butyldiphenylsilyl, triisopropylsilyl and isopropyldimethylsilyl. In a preferred embodiment $A^1$ is acetyl.

In some embodiments, acetyl is used as the protecting group $A^1$. When GalNAc phosphoramidites according to formula (I) are used in the synthesis of nucleic acid conjugates, the acetyl groups may be removed together with the protecting groups of the nucleic acid, e.g. LNA or DNA, in the cleavage and deprotecting step normally used in e.g. LNA synthesis.

In some embodiments, dimethoxytrityl (DMT) is used as the protecting group $A^1$ at carbon atom 6 of the GalNAc. The advantage of using DMT at this position is that it allows for easy separation of failure sequences (e.g. non-complete constructs where a failure in the synthesis has resulted in the GalNAc moiety not being added) during purification.

In specific embodiments according to the invention, the compound has the general formula (I), wherein A is —O—CH$_2$CH$_2$CN, R' and R" each are isopropyl, and G is represented by formula (II), wherein $A^1$ is acetyl and L is selected from the group consisting of —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$CH$_2$OCH$_2$CH$_2$—, —CH$_2$CH$_2$OCH$_2$CH$_2$OCH$_2$CH$_2$—, and —CH$_2$CH$_2$(OCH$_2$CH$_2$)$_2$OCH$_2$CH$_2$—. In certain preferred embodiments, A is —O—CH$_2$CH$_2$CN, R' and R" each are isopropyl, $A^1$ is acetyl and L is —(CH$_2$)$_2$—. In other preferred embodiments, A is —O—CH$_2$CH$_2$CN, R' and R" each are isopropyl, $A^1$ is acetyl and L is —(CH$_2$)$_3$—. In other preferred embodiments A is —O—CH$_2$CH$_2$CN, R' and R" each are isopropyl, $A^1$ is acetyl and L is —CH$_2$CH$_2$OCH$_2$CH$_2$OCH$_2$CH$_2$—. In other preferred embodiments, A is —O—CH$_2$CH$_2$CN, R' and R" each are isopropyl, $A^1$ is acetyl and L is —(CH$_2$)$_8$—. Optionally, in the above preferred embodiments $A^1$ at position 6 of the sugar is DMT.

Figure 5:
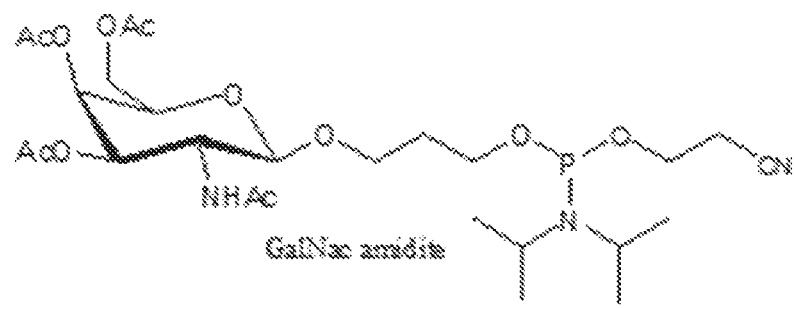
Figure 5:
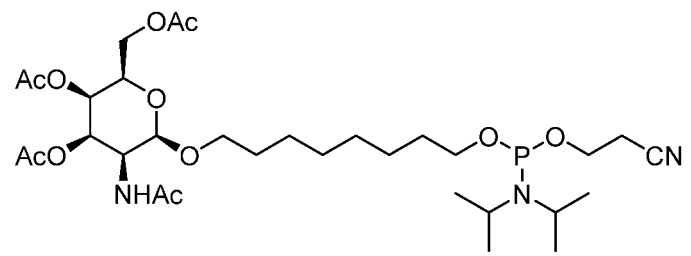
Figure 5:
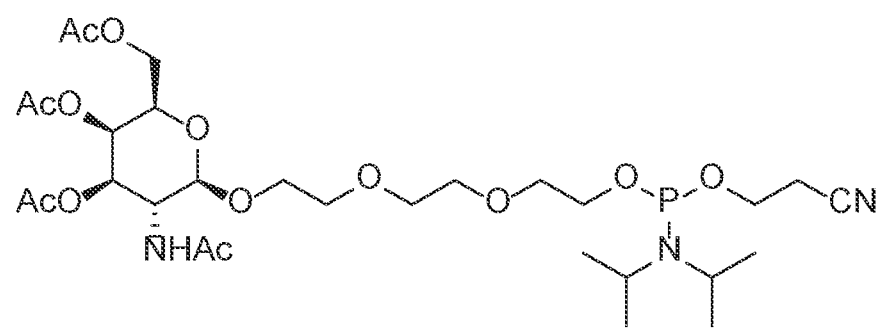
Figure 5:
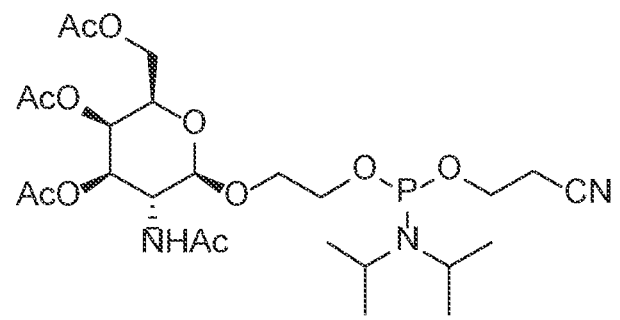

Exemplary GalNAc phosphoramidites are represented in FIG. 5 by formulas (A) to (D).

GalNAc-Nucleic Acid Conjugates

In a further aspect, the present invention relates to novel GalNAc-nucleic acid conjugates, in particular GalNAc cluster conjugates. The GalNAc conjugate moieties can modify or enhance the pharmacokinetic and pharmacodynamic properties of the attached nucleic acid.

Accordingly, the invention provides a compound having the general formula (III)

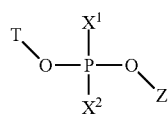

(III)

wherein

Z is a nucleic acid molecule;

T is represented by general formula (IV)

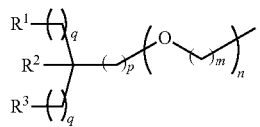

(IV)

wherein $R^2$ represents H or —(CH$_2$)$_q$—$R^1$, $R^1$ and $R^3$ at each occurrence are represented by general formula (V)

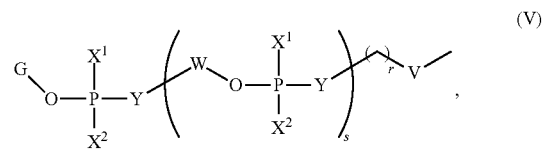

(V)

wherein independently at each occurrence

V is selected from —O—, —NH—CO— and —CO—NH—;

W is selected from the group consisting of —(CH$_2$)$_{2-15}$— and —CH$_2$CH$_2$(OCH$_2$CH$_2$)$_{0-4}$OCH$_2$CH$_2$—;

Y is O or S;

m is an integer from 1 to 3;

n is an integer from 0 to 5;

p is an integer from 0 to 3; and q is an integer from 1 to 2;

r is an integer from 1 to 5;

s is 0 or 1

G is represented by general formula (II)'

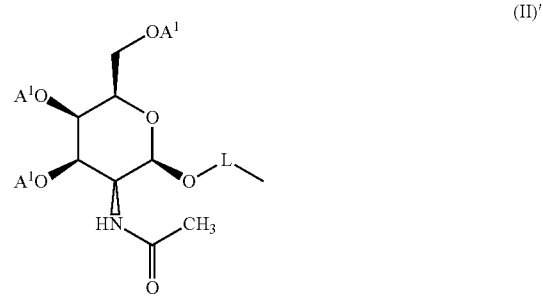

(II)' wherein $A^1$ is H or a suitable hydroxyl protecting group, which may be the same or different at each occurrence; and L is a linker group with a chain length of from 2-23 carbon atoms, wherein one or more of the carbon atoms in the chain may each independently be replaced by —NH—CO—, —CO—NH— and/or a heteroatom, particularly O; and independently at each occurrence $X^1$ is —OH and $X^2$ is selected from =O and =S, or $X^1$ is —O$^-$ and $X^2$ is selected from =O and =S, or $X^1$ is =O and $X^2$ is selected from —CH$_3$, —OR, —NHR, and —BH$_3$, wherein R is independently at each occurrence a $C_1$-$C_6$ alkyl group, or $X^1$ is =S and $X^2$ is selected from —CH$_3$ and —SH, wherein the contiguous chain starting with the first atom of linker L in $R^1$, $R^3$ or, if $R^2$ is not H, $R^2$, and ending with the attachment point in formula (IV) has a minimum length of 8 atoms and a maximum length of 30 atoms.

Alternatively, the invention provides a compound having the general formula (III)×

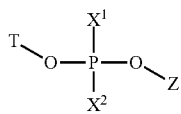
(III)

wherein
Z is a nucleic acid molecule;
T is represented by general formula (VI)

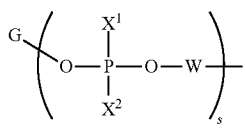
(VI)

wherein independently at each occurrence
W is selected from the group consisting of —$(CH_2)_{2\text{-}15}$— and —$CH_2CH_2(OCH_2CH_2)_{0\text{-}4}OCH_2CH_2$—;
s is 0 or 1
G is represented by general formula (II)'

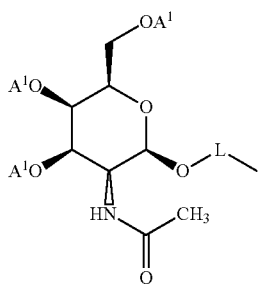
(II)' wherein A is H or a suitable hydroxyl protecting group, which may be the same or different at each occurrence; and L is a linker group with a chain length of from 2-23 carbon atoms, wherein one or more of the carbon atoms in the chain may each independently be replaced by —NH—CO—, —CO—NH— and/or a heteroatom, particularly O; and
independently at each occurrence
$X^1$ is —OH and $X^2$ is selected from =O and =S, or
$X^1$ is —O⁻ and $X^2$ is selected from =O and =S, or
$X^1$ is =O and $X^2$ is selected from —$CH_3$, —OR, —NHR, and —$BH_3$, wherein R is independently at each occurrence a $C_1$-$C_6$ alkyl group, or
$X^1$ is =S and $X^2$ is selected from —$CH_3$ and —SH,
wherein the contiguous chain starting with the first atom of linker L and ending with the attachment point in the nucleic acid molecule has a minimum length of 8 atoms and a maximum length of 30 atoms.

The first atom of the linker L is the atom where the linker is attached to the GalNAc moiety in formula II and II'.

The variable Z in formula (III) represents a nucleic acid molecule. The nucleic acid molecules referred to in the context of the invention will be more extensively described below and can generally be DNA, RNA or may comprise a nucleotide sequence which comprises both nucleotides and nucleotide analogues or is completely consisting of nucleotide analogues. The GalNAc conjugate moiety can either be built on to the 5'- or 3'-end of the nucleic acid. Preferably, the GalNAc conjugate moiety is built on to the 5'-end of the nucleic acid molecule.

In particular, the nucleic acid molecule Z may contain one or more locked nucleic acid nucleosides.

Particularly, the nucleic acid molecule may contain one or more phosphorothioate or boranophosphate internucleoside linkages. Preferably, DNA and RNA nucleosides are linked with phosphorothioate or boranophosphate. In some embodiments, all the nucleosides and/or nucleoside analogues in the nucleic acid molecule are linked with phosphorothioate or boranophosphate. In preferred embodiments a PO linker is placed between the nucleic acid and the GalNAc conjugate moiety. Alternatively other linkers can be placed between the nucleic acid and the GalNAc conjugate moiety.

The variable T in general formula (III) is represented by general formula (IV). General formula (IV) shows the branching region of the GalNAc cluster nucleic acid conjugate. When $R^2$ is H, the branching molecule is a doubler, i.e. during synthesis, two GalNAc phosphoramidites are added to the reactive end of the branching molecule. When $R^2$ is —$(CH_2)_q$—$R^1$, the branching molecule is a trebler, i.e. during synthesis, three GalNAc phosphoramidites are added to the reactive end of the branching molecule.

Alternatively, the variable T in general formula (III) is represented by general formula (VI). This would lead to a monovalent GalNAc-nucleic acid conjugate where the W or G in formula (VI) is conjugated to the nucleic acid or a linker (e.g. a PO linker). In a preferred embodiment s is 0 when T in formula (III) is represented by formula (VI).

R' and R" of the secondary amino group —NR'R" in formula (III) are selected from $C_1$-$C_6$ alkyl or R' and R" together form a five- or six-membered ring, which may be substituted and which may contain one further heteroatom selected from N and O, wherein specific $C_1$-$C_6$ alkyl groups and rings are selected from those defined above with regard to formula (I). In particular embodiments, R' is identical to R", and —NR'R" is selected from the group consisting of dimethylamino, diethylamino, diisopropylamino, and dibutylamino. In a preferred embodiment R' and R" each are isopropyl.

In other embodiments, R' and R" together form a five- or six-membered ring as set forth above with regard to formula (I). In particular, the ring is selected from the group consisting of pyrrolidino, piperidino, 2,6-dimethylpiperidino, morpholino, imidazolyl and 4-methylimidazolyl.

The variable T in formula (III) is represented by general formula (IV), which, via $R^1$, $R^3$ and, if $R^2$ is not H, $R^2$, makes reference to formula (V), which in turn, via G, refers to formula (II)'. The variables occurring in formulae (IV), (V) and (II)' are further defined as follows.

The variable m in formula (IV) is an integer from 1 to 3, i.e. it represents 1, 2 or 3, preferably 2 or 3.

The variable n in formula (IV) is an integer from 0 to 5, i.e. it represents 0, 1, 2, 3, 4 or 5. In preferred embodiments, n is 0.

The variable p in formula (IV) is an integer from 0 to 3, i.e. it represents 0, 1, 2 or 3, preferably 0 or 1. In certain preferred embodiments, p is 1. In other preferred embodiments, p is 0.

The variable q in formula (IV) is, independently at each occurrence, an integer from 1 to 2, i.e. it represents 1, or 2.

In preferred embodiments, q is the same integer at each occurrence. In particularly preferred embodiments, q is 1 at each occurrence.

In particular embodiments of the invention, n is 0, p is 1 and q is 1; in other embodiments, n is 0, p is 0 and q is 1; in still other embodiments, n is 1, m is 1, 2 or 3, preferably 3, p is 1 and q is 1.

For the purposes of the invention, the topological positioning of two or three GalNAc moieties in a cluster is expected to be important for function. For example, this positioning may influence its ability to bind the asialoglycoprotein receptor (ASGPR), which is one exemplary application of the novel compounds described herein. Therefore, it is important that the backbone of the GalNAc-cluster does not superate a certain length. By the term "backbone", a contiguous chain of atoms is meant. For example, the backbone of ethane is C—C (contiguous chain of 2 atoms), and the backbone of diethylether is C—C—O—C—C (contiguous chain of 5 atoms). With regard to the compounds of general formula (III), the contiguous chain starting with the first atom of linker L in R1 and ending with the attachment point in formula (IV), or starting with the first atom of linker L in $R^3$ and ending with the attachment point in formula (IV), or, if $R^2$ is not H, starting with the first atom of linker L in $R^2$ and ending with the attachment point in formula (IV), is defined as having a maximum length of 30 atoms.

It is to be understood that the individual contiguous chains may vary in their length, but no single one of these contiguous chains is longer than 30 atoms. For example, the length of each of the contiguous chains may be independently 8, 9, 10, 12, 14, 16, 18, 20, 25 or 30 atoms in length. In certain embodiments, each of the contiguous chains starting with the first atom of linker L in $R^1$, $R^3$, and, if $R^2$ is not H, $R^2$, and ending with the attachment point in formula (IV), has the same length. In other embodiments each of the contiguous chains starting with the first atom of linker L in $R^1$, $R^3$, and, if $R^2$ is not H, $R^2$, and ending with the attachment point in formula (IV), have different length For example, each of the three contiguous chains may have a length of 16 atoms or 22 atoms, independent of each other.

As an alternative to defining the length by the number of atoms, the length of the backbone can also be defined by units of length, e.g. in Ångström (1 Å=$10^{-10}$ meter). With regard to the compounds general formula (III), the contiguous chain starting with the first atom of linker L in $R^1$ and ending with the attachment point in formula (IV), or starting with the first atom of linker L in $R^3$ and ending with the attachment point in formula (IV), or, if $R^2$ is not H, starting with the first atom of linker L in $R^2$ and ending with the attachment point in formula (IV) is defined as being between 10 and 25 Å, more preferably from 12 to 22 Å and most preferably from 14 to 20 Å. In one embodiment the contiguous chain starting with the first atom of linker L in $R^1$ ending with the attachment point in formula (IV), is between 14 and 20 Å, more preferably between 16 and 18 Å and each of the contiguous chain starting with the first atom of linker L in $R^3$ ending with the attachment point in formula (IV), is between 10 and 18 Å, more preferably between 14 and 16 Å and the contiguous chain starting with the first atom of linker L in $R^1$, $R^3$, and, if $R^2$ is not H, $R^2$, and ending with the attachment point in formula (IV), has the same length is between 16 and 25 Å, more preferably between 18 and 20 Å.

The "attachment point" is the carbon atom of the —$CH_2$- group in —$(CH_2)_q$— directly bound to the branching point carbon atom in each of the branches present in formula (IV).

In certain preferred embodiments, where the GalNAc phosphoramidite is attached via direct coupling onto a trebler, the length of the backbone of linker group L is around 8 atoms, i.e. 6, 7, 8, 9 or 10 atoms.

In certain embodiments, the length of the contiguous chain starting with the first atom of linker L in $R^1$, $R^3$ or, if $R^2$ is not H, $R^2$, and ending with the attachment point in formula (IV) is adjusted mainly by selecting an appropriate linker group L. In these embodiments, the variable s in formula (V) is 0.

However, according to other embodiments of the invention, a similar construct can be assembled using a short linker in the GalNAc phosphoramidite, combining it with a spacer phosphoramidite. This is a convenient way to vary the length of the linker between the brancher (or nucleic acid if no brancher is present) and the GalNAc moiety without having to make separate GalNAc phosphoramidites with different linkers. In these embodiments, the variable s in formula (V) is 1.

In certain preferred embodiments, the contiguous chain starting with the first atom of linker L in $R^1$, $R^3$ or, if $R^2$ is not H, $R^2$, and ending with the branching point carbon atom in formula (IV)

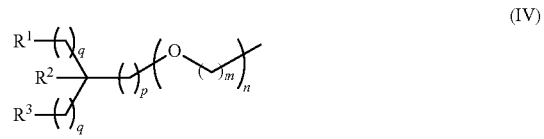

(IV)

has a length of from 9 to 23 atoms. In further preferred embodiments, the contiguous chain starting with the first atom of linker L in $R^1$, $R^3$ or, if $R^2$ is not H, $R^2$, and ending with the branching point carbon atom in formula (IV), has a length of from 9 to 21 atoms, such as 12 to 18 atoms, e.g. 16 atoms. The "branching point carbon atom" is the carbon atom to which —$(CH_2)_q$—$R^1$, —$(CH_2)_q$—$R^3$ and $R^2$ are bound to (see FIG. 1).

In embodiments where s in formula (V) or (VI) is 1, the variable W in formula (V) is selected from the group consisting of —$(CH_2)_{2-15}$—, i.e. —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, and —$CH_2CH_2(OCH_2CH_2)_{0-4}OCH_2CH_2$—, i.e. —$CH_2CH_2OCH_2CH_2$—, —$CH_2CH_2OCH_2CH_2OCH_2CH_2$—, —$CH_2CH_2(OCH_2CH_2)_2OCH_2CH_2$—, —$CH_2CH_2(OCH_2CH_2)_3OCH_2CH_2$—, and —$CH_2CH_2(OCH_2CH_2)_4OCH_2CH_2$—. In a preferred embodiment, W is —$(CH_2)_8$— or $CH_2CH_2OCH_2CH_2OCH_2CH_2$—. In another preferred embodiment W is —$(CH_2)_5$— or —$CH_2CH_2OCH_2CH_2$—. In another preferred embodiment W is —$(CH_2)_2$— or —$CH_2CH_2CH_2$.

The variable r in formula (V) is, independently at each occurrence, an integer from 1 to 5, i.e. it represents 1, 2, 3, 4 or 5. In preferred embodiments, r is the same integer at each occurrence. In particularly preferred embodiments, r is 3 at each occurrence. In other preferred embodiments, r is 4 at each occurrence.

The variable V in formula (V) is, independently at each occurrence, selected from —O—, —NH—CO— and —CO—NH—. In certain preferred embodiments, V is —NH—CO— at each occurrence. In other preferred embodiments, V is —O— at each occurrence.

The variable Y in formula (V) is, independently at each occurrence, selected from O and S. In certain preferred embodiments, Y is O at each occurrence.

The variables $X^1$ and $X^2$ in formula (III), (V) and (VI) are, independently at each occurrence, selected from a number of different combinations:

In some embodiments $X^1$ is —OH and $X^2$ is =O;
in other embodiments, $X^1$ is —OH and $X^2$ is =S;
in still further embodiments, $X^1$ is —O⁻ and $X^2$ is =O;
in still further embodiments, $X^1$ is —O⁻ and $X^2$ is =S;
in still further embodiments, $X^1$ is =O and $X^2$ is —CH$_3$;
in still further embodiments, $X^1$ is =O and $X^2$ is —SH;
in still further embodiments, $X^1$ is =O and $X^2$ is —OR, wherein R is a $C_1$-$C_6$ alkyl group, preferably methyl or ethyl;
in still further embodiments, $X^1$ is =O and $X^2$ is —NHR, wherein R is a $C_1$-$C_6$ alkyl group, preferably methyl or ethyl;
in still further embodiments, $X^1$ is =O and $X^2$ is —BH$_3$;
in still further embodiments, $X^1$ is =S and $X^2$ is —CH$_3$;
in still further embodiments, $X^1$ is =S and $X^2$ is —SH.

In preferred embodiments, the variables $X^1$ and $X^2$ in formula (III), (V) and (VI) are, independently at each occurrence, selected from the group consisting of the following combinations:

$X^1$ is —OH and $X^2$ is =O;
$X^1$ is O⁻ and $X^2$ is =O;
$X^1$ is —OH and $X^2$ is =S;
$X^1$ is O⁻ and $X^2$ is =S; and
$X^1$ is =S and $X^2$ is —SH.

In certain preferred embodiments, Y, $X^1$ and $X^2$ are selected such that the group —O—P($X^1X^2$)—Y— in formula (V), independently at each occurrence, represents a phosphodiester group ($X^1$=—OH or —O⁻, $X^2$=O, Y=O), a methyl phosphonate group ($X^1$=O, $X^2$=—CH$_3$, Y=O), a phosphorothioate group ($X^1$=—OH, $X^2$=S, Y=O), a phosphorodithioate group ($X^1$=S, $X^2$=—SH, Y=O), an alkylphosphotriester group ($X^1$=O, $X^2$=—OC$_1$-C$_6$-alkyl, Y=O), a methylphosphonothioate group ($X^1$=S, $X^2$=—CH$_3$, Y=O), an alkylphosphoramidite group ($X^1$=O, $X^2$=—NHC$_1$-C$_6$-alkyl, Y=O), or a boranophosphate group ($X^1$=O, $X^2$=—BH$_3$, Y=O).

In further preferred embodiments, Y, $X^1$ and $X^2$ are selected such that the group —O—P($X^1X^2$)—Y— in formula (V), independently at each occurrence, represents a phosphodiester group, a phosphorothioate group or a phosphorodithioate group. In particularly preferred embodiments, Y, $X^1$ and $X^2$ are selected such that the group —O—P($X^1X^2$)—Y— in formula (V), independently at each occurrence, represents a phosphodiester group or a phosphorothioate group.

In some embodiments, Y, $X^1$ and $X^2$ are selected such that they represent the same group at each occurrence, preferably a phosphodiester group or a phosphorothioate group.

The variable G in formula (V) or (VI) is represented by formula (II)'. In formula (II)', $A^1$ is a protecting group which is selected such that it is stable to the reaction conditions it will be exposed to, such as the conditions used in the process for preparing the phosphoramidite, and the coupling and oxidation step of the cluster and oligonucleotide synthesis process. As example for a suitable hydroxyl protecting group $A^1$ according to formula (II)', acyl groups and silyl groups may be mentioned. Preferably, the protecting group $A^1$ is selected from the group consisting of acetyl, benzoyl, phenoxy-acetyl, pivaloyl, dimethoxytrityl (DMT), isobutyryl, t-butyldimethylsilyl, t-butyldiphenylsilyl, triisopropylsilyl and isopropyldimethylsilyl.

In a preferred embodiment $A^1$ is acetyl. In some embodiments, dimethoxytrityl (DMT) is used as the protecting group $A^1$ at position 6 of the sugar. The advantage of using DMT at this position is that it allows for easy separation of failure sequences (e.g. non-complete constructs where a failure in the synthesis has resulted in the GalNAc moiety not being added) during purification.

The linker group L in formula (II)' is selected according to the desired application of the GalNAc nucleic acid conjugate. In some embodiments, one or more of the carbon atoms in the chain may each independently be replaced by —NH—CO—, —CO—NH— and/or a heteroatom, particularly O. The number of replacements should be adapted such that the total length of the linker does not exceed 30 atoms after replacements and maintaining at least one neighbouring atom to the replacements as carbon atoms in the case of —NH—CO—, —CO—NH and at least 2 neighbouring carbon atoms in the case of heteroatom replacements. In some embodiments the number of replacements is less than 5 and the neighbouring atoms to the replacements are carbon atoms. In some embodiments no more than one or two replacements are made in the chain and the neighbouring atoms to the replacements are carbon atoms. For example, the linker between the GalNAc moiety and the phosphoramidite may be derived from a simple diol. In principle, any symmetrical or unsymmetrical diol could be used as a linker in the GalNAc phosphoramidite of the invention, provided they contain no other nucleophilic groups.

In some embodiments, carbon atoms in the chain are replaced by oxygen atoms in order to form an array of —(OCH$_2$CH$_2$)-groups.

In certain embodiments, L is selected from the group consisting of $C_2$-$C_2$-alkylene, $C_2$-$C_{20}$-alkenylene, and —CH$_2$CH$_2$—(OCH$_2$CH$_2$)$_{0-6}$—OCH$_2$CH$_2$—, CH$_2$CH$_2$—(OCH$_2$CH$_2$)$_{0-3}$—OCH$_2$CH$_2$—, and CH$_2$CH$_2$—(OCH$_2$CH$_2$)$_{0-4}$—OCH$_2$CH$_2$. More specifically the alkylene is selected from $C_3$-$C_{19}$-alkylene, but not C alkylene or from $C_7$-$C_{19}$-alkylene. More specifically, the linker group L may be selected from the group consisting of —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$CH$_2$OCH$_2$CH$_2$—, —CH$_2$CH$_2$OCH$_2$CH$_2$OCH$_2$CH$_2$—, and —CH$_2$CH$_2$(OCH$_2$CH$_2$)$_2$OCH$_2$CH$_2$—. In preferred embodiments, the linker L is —(CH$_2$)$_2$— or —(CH$_2$)$_3$—. In other preferred embodiments, the linker L is —(CH$_2$)— or —CH$_2$CH$_2$OCH$_2$CH$_2$OCH$_2$CH$_2$—. In another preferred embodiment, the linker L is —(CH$_2$)$_5$ or —CH$_2$CH$_2$OCH$_2$CH$_2$—. In another preferred embodiment, the linker L is CH$_2$CH$_2$OCH$_2$CH$_2$—, —CH$_2$CH$_2$OCH$_2$CH$_2$OCH$_2$CH$_2$—, or —CH$_2$CH$_2$(OCH$_2$CH$_2$)$_2$OCH$_2$CH$_2$—.

In certain embodiments according to the present invention, the doubler or trebler is asymmetrical, i.e. at least one of the variables q, r, s, $X^1$ and $X^2$ in formula (IV) and (V) has one specific meaning at its first occurrence (e.g. in $R^1$) and a different specific meaning at the second and/or further occurrence(s) (e.g. in $R^3$ and/or $R^2$). In some embodiments, the asymmetry regards particularly the length of the branches defined by $R^1$, $R^3$ and optionally $R^2$, meaning that at least one of the variables q, r and s has a different value at its first occurrence as compared to its second and/or third occurrence.

In preferred embodiments, the doubler or trebler is symmetrical at least with regard to the length of the branches defined by $R^1$, $R^3$ and optionally $R^2$, i.e. the variables q, r and s have the same value at each occurrence. In some embodiments, additionally the variables $X^1$ and $X^2$ and/or $A^1$ represent the same group at each occurrence.

In certain specific embodiments of the GalNAc-nucleic acid conjugate according to formula (III), n is 0, p is 0, $R^2$ is H, q is 1, V is —NH—CO—, and r is 4. In other specific embodiments, n is 0, p is 1, $R^2$ is —$(CH_2)_q$—$R^1$, q is 1, V is —O—, and r is 3. In yet other specific embodiments, n is 1, m is 3, p is 1, $R^2$ is —$(CH_2)_q$—$R^1$, q is 1, V is —O—, and r is 3.

Still more specifically, in some preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is =O, $X^2$ is —SH, W is —$CH_2CH_2OCH_2CH_2OCH_2CH_2$—, Y is O, L is —$CH_2CH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is —$O^-$, $X^2$ is =S, W is —$CH_2CH_2OCH_2CH_2OCH_2CH_2$—, Y is O, L is —$CH_2CH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is —$O^-$, $X^2$ is =S, W is —$CH_2CH_2CH_2$—, Y is O, L is —$CH_2CH_2OCH_2CH_2OCH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is =O, $X^2$ is —SH, W is —$CH_2CH_2CH_2$—, Y is O, L is —$CH_2CH_2OCH_2CH_2OCH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is =O, $X^2$ is —SH, W is —$CH_2CH_2OCH_2CH_2OCH_2CH_2$—, Y is O, L is —$CH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is —$O^-$, $X^2$ is =S, W is —$CH_2CH_2OCH_2CH_2OCH_2CH_2$—, Y is O, L is —$CH_2CH_2$—, and $A^1$ is acetyl.

In other preferred embodiments of the GalNAc-nucleic acid conjugate according to formula (III), n is 0, p is 1, $R^2$ is —$(CH_2)_q$—$R^1$, q is 1, V is —O—, r is 3, s is 1, $X^1$ is —$O^-$ or =O, $X^2$ is =S or —SH, W is —$CH_2CH_2$—, Y is O, L is —$CH_2CH_2OCH_2CH_2OCH_2CH_2$—, and $A^1$ is acetyl.

In other preferred embodiments, n is 0, p is 1, $R^2$ is —$(CH_2)_q$—$R^1$, q is 1, V is —O—, r is 3, s is 0, $X^1$ is —$O^-$, $X^2$ is =S, Y is O, L is —$(CH_2)_8$—, and $A^1$ is acetyl.

In other preferred embodiments, n is 0, p is 1, $R^2$ is —$(CH_2)_q$—$R^1$, q is 1, V is —O—, r is 3, s is 0, $X^1$ is =O, $X^2$ is SH, Y is O, L is —$(CH_2)_8$—, and $A^1$ is acetyl.

In other preferred embodiments, n is 0, p is 1, $R^2$ is —$(CH_2)_q$—$R^1$, q is 1, V is —O—, r is 3, s is 0, $X^1$ is —$O^-$, $X^2$ is =S, Y is O, L is $CH_2CH_2OCH_2CH_2OCH_2CH_2$—, and $A^1$ is acetyl.

In other preferred embodiments, n is 0, p is 1, $R^2$ is —$(CH_2)_q$—$R^1$, q is 1, V is —O—, r is 3, s is 0, $X^1$ is =O, $X^2$ is —SH, Y is O, L is $CH_2CH_2CH_2CH_2OCH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is —$O^-$, $X^2$ is =S, W is —$CH_2CH_2CH_2$—, Y is O, L is —$CH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is =O, $X^2$ is —SH, W is —$CH_2CH_2CH_2$—, Y is O, L is —$CH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is =O, $X^2$ is —SH, W is —$CH_2CH_2CH_2$—, Y is O, L is —$CH_2CH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is =O, $X^2$ is —SH, W is —$CH_2CH_2OCH_2CH_2$—, Y is O, L is —$CH_2CH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is —$O^-$, $X^2$ is =S, W is —$CH_2CH_2OCH_2CH_2$—, Y is O, L is —$CH_2CH_2CH_2$—, and $A^1$ is acetyl.

In yet other preferred embodiments, n is 0, p is 1, $R^2$ is —$(CH_2)_q$—$R^1$, q is 1, V is —O—, r is 3, s is 1, $X^1$ is —$O^-$ or =O, $X^2$ is =S or —SH, W is —$CH_2CH_2CH_2$—, Y is O, L is —$CH_2CH_2OCH_2CH_2$—, and $A^1$ is acetyl.

In yet other preferred embodiments, n is 0, p is 1, $R^2$ is —H, q is 0, V is —O—, r is 3, s is 1, $X^1$ is —$O^-$ or =O, $X^2$ is =S or —SH, Y is O, L is —$CH_2CH_2OCH_2CH_2$—, and $A^1$ is acetyl.

In all the preferred embodiments indicated above the $X^1$ and $X^2$ of formula (III) may be selected independently of the $X^1$ and $X^2$ in formula (V) and (VI). Preferably in the preferred embodiments above $X^1$ and $X^2$ of formula (III) are $X^1$ is —$S^-$ or —$O^-$ or =O and $X^2$ is =O or =S or —OH or —SH.

Exemplary embodiments of a GalNAc-nucleic acid conjugates are represented in FIG. 6 by formulas (A)-(N).

The term oligonucleotide in the formulas (A)-(N) is to be understood in the broad contexts of nucleic acid.

The GalNAc cluster nucleic acid conjugates according to the invention may be specifically designed for binding to the asialoglycoprotein receptor (ASGPR). Thus, according to some embodiments, a monovalent, a bivalent or, preferably, trivalent GalNAc nucleic acid conjugate according to the invention has a strong affinity for the ASGPR. In relation to the present invention "strong affinity" means an affinity characterized by an $IC_{50}$ value below 50 nM, preferably 25 nM or less, more preferably 10 nM or less, more preferably 5 nM or less.

In particularly preferred embodiments, the $IC_{50}$ for ASGPR of a GalNAc-nucleic acid conjugate with a monovalent GalNAc cluster is 50 nM, preferably 25 nM or less, more preferably 15 nM or less, more preferably 10 nM or less, more preferably 5 nM or less.

In particularly preferred embodiments, the $IC_{50}$ for ASGPR of a GalNAc-nucleic acid conjugate with a bivalent GalNAc cluster is 50 nM, preferably 25 nM or less, more preferably 15 nM or less, more preferably 10 nM or less, more preferably 5 nM or less.

In further particularly preferred embodiments, the $IC_{50}$ for ASGPR of a GalNAc-nucleic acid conjugate with a trivalent GalNAc phosphoramidite cluster is 25 nM or less, preferably 15 nM or less, more preferably 10 nM or less, more preferably 5 nM or less, more preferably between 1 nM and 5 nM, e.g. about 3 nM. The $IC_{50}$ is the concentration of GalNAc-nucleic acid conjugate that inhibits labelled ligand binding to the ASPGR by 50%. The $IC_{50}$ can be determined by the method described in Rensen et al 2001 Journal of Biological Chemistry Vol 276 pp 37577. In brief Hepatocytes (primary or in culture) are incubated with the ligand $^{125}$I-labelled asialylated orosomucoid (ASOR) at one concentration (e.g. 5 nM) for 2 h at 4° C. in the presence of increasing amounts of the GalNAc-nucleic acid conjugate to be investigated. For monovalent GalNAc-nucleic acid conjugates the concentrations could be from 2 to 200 mM; for bivalent GalNAc-nucleic acid conjugates the concentrations could be from 1 to 1000 nM; and for trivalent GalNAc-nucleic acid conjugates the concentrations could be from 0.2 to 200 nM, at increasing concentrations. The binding of the labelled ASOR is followed in the presence of the GalNAc-nucleic acid conjugate to be investigated.

Nonspecific binding can be determined in the presence of 100 mM GalNAc. Displacement binding data can be analysed using a single site binding model and the $IC_{50}$ is calculated.

Preparation of GalNAc Phosphoramidites

In a further aspect, the present invention relates to a manufacturing process of GalNAc phosphoramidites. Accordingly, the invention provides a process for the preparation of a compound of formula (I), comprising the steps:

(i) stereoselectively forming an internal oxazoline ring between carbon atoms 1 and 2 of N-Acetylgalactosamine (GalNAc);

(ii) reacting the product of step (i) with a compound having the general formula HO-L-O-$A^3$, wherein $A^3$ is a suitable protecting group and L is a linker group with a chain length of from 2-30 carbon atoms, wherein one or more of the carbon atoms in the chain may each independently be replaced by —NH—CO—, —CO—NH— and/or a heteroatom, particularly O, wherein L is preferably selected from the group consisting of —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$CH_2CH_2OCH_2CH_2$—, —$CH_2CH_2OCH_2CH_2OCH_2CH_2$—, and —$CH_2CH_2(OCH_2CH_2)_2OCH_2CH_2$—, thereby forming an ether bond at carbon atom 1 of the GalNAc ring;

(iii) deprotecting the —O-$A^3$ group in the product of step (ii), thereby providing a deprotected —OH group, (iv) reacting the product of step (iii) with a phosphordiamidite, or a chlorophosphoramidite thereby providing a compound according to formula (I).

The protecting group $A^3$ must be suitable to protect one of the hydroxy groups of a diol of general formula HO-L-OH. Such protecting groups are known to the skilled person in the field of organic synthesis. For example, acyl groups and silyl groups may be used. In certain preferred embodiments, the protecting group $A^3$ is selected from the group consisting of acetyl, benzoyl, phenoxy-acetyl, pivaloyl, isobutyryl, t-butyldimethylsilyl, t-butyldiphenylsilyl, triisopropylsilyl and isopropyldimethylsilyl. In a preferred embodiment $A^3$ is an t-butyldiphenylsilyl group.

The linker group L in HO-L-O-$A^3$ is selected according to the desired application of the GalNAc phosphoramidite. In some embodiments, one or more of the carbon atoms in the chain may each independently be replaced by —NH—CO—, —CO—NH— and/or a heteroatom, particularly O. The number of replacements should be adapted such that the total length of the linker does not exceed 30 atoms after replacements and maintaining at least one neighbouring atom to the replacements as carbon atoms in the case of —NH—CO—, —CO—NH and at least 2 neighbouring carbon atoms in the case of heteroatom replacements. In some embodiments the number of replacements is less than 5 and the neighbouring atoms to the replacements are carbon atoms. In some embodiments no more than one or two replacements are made in the chain and the neighbouring atoms to the replacements are carbon atoms.

In certain embodiments, L is selected from the group consisting of $C_2$-$C_{30}$-alkylene, $C_2$-$C_3$-alkenylene, and —$CH_2CH_2$—$(OCH_2CH_2)_{0-8}$—$OCH_2CH_2$—. More specifically, the linker group L may be selected from $C_2$-$C_{20}$-alkylene, $C_2$-$C_{20}$-alkenylene, and —$CH_2CH_2$—$(OCH_2CH_2)_{0-6}$—$OCH_2CH_2$—. Even more specifically, the linker group L may be selected from the group consisting of —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$CH_2CH_2OCH_2CH_2$—, —$CH_2CH_2OCH_2CH_2OCH_2CH_2$—, and —$CH_2CH_2(OCH_2CH_2)_2OCH_2CH_2$—. In preferred embodiments, the linker L is —$(CH_2)_2$— or —$(CH_2)_3$—. In other preferred embodiments, the linker L is —$(CH_2)$— or —$CH_2CH_2OCH_2CH_2OCH_2CH_2$—. In another preferred embodiment, the linker L —$CH_2CH_2OCH_2CH_2$—. In another preferred embodiment, the linker L is —$CH_2CH_2OCH_2CH_2$—, —$CH_2CH_2OCH_2CH_2OCH_2CH_2$—, or —$CH_2CH_2(OCH_2CH_2)_2OCH_2CH_2$—.

The skilled person in the field of organic synthesis is aware of several standard protocols for deprotecting protected hydroxy groups. Depending on the used protection group, deprotection can be carried out e.g. by adding mild acid or mild base or a catalyst etc.

Preparation of GalNAc Nucleic Acid Conjugates

In yet a further aspect, the present invention relates to a manufacturing process of a nucleic acid conjugate using at least one GalNAc phosphoramidite.

Accordingly, the invention provides a process for the preparation of a GalNAc-nucleic acid conjugate, comprising the steps:

(i) providing a nucleic acid molecule on a solid support;

(ii) optionally adding a brancher molecule to the nucleic acid molecule using phosphoramidite chemistry;

(iii) optionally adding a spacer phosphoramidite molecule to each of the branches of the brancher molecule using phosphoramidite chemistry;

(iv) reacting a compound according to formula (I) with the reactive end of the nucleic acid molecule, if no brancher molecule is present, or reacting a compound according to formula (I) with the reactive end of each of the branches, if a brancher molecule is present and no spacers are present, or reacting a compound according to formula (I) with the reactive end of each of the spacers, if spacers are present; and (v) cleaving the product of step (iv) from the solid support;

wherein the contiguous chain starting with the first atom of linker L in the compound according to formula (I) and ending with the phosphorus atom linking the conjugate moiety to the nucleic acid has a minimum length of 10 atoms and a maximum length of 34 atoms.

More particularly, the invention provides a process for the preparation of a nucleic acid conjugate, comprising the steps:

(i) providing a nucleic acid molecule on a solid support;

(ii) optionally adding a brancher molecule to the nucleic acid molecule using phosphoramidite chemistry, wherein said brancher molecule after addition results in structures preferably represented by general formula (IV a)

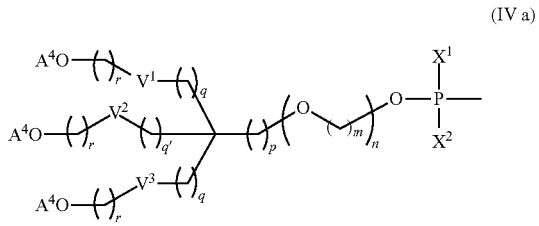

(IV a)

wherein
A⁴ is a suitable protecting group;
V¹ is selected from —O—, —NH—CO— and —CO—NH—;
V² is absent or is selected from —O—, —NH—CO— and —CO—NH—;
V³ is selected from —O—, —NH—CO— and —CO—NH—;
X¹ is —OH and X² is selected from =O and =S, or
X¹ is O⁻ and X² is selected from =O and =S, or
X¹ is =O and X² is selected from —CH₃, —SH, —OR, —NHR, and —BH₃, wherein R is independently at each occurrence a $C_1$-$C_6$ alkyl group, or
X¹ is =S and X² is selected from —CH₃ and —SH;
m is an integer from 1 to 3;
n is an integer from 0 to 5;
p is an integer from 0 to 3; and independently at each occurrence
q is an integer from 1 to 2;
q' is an integer from 0 to 2; and
r is an integer from 1 to 5;
with the proviso that when V² is absent, q' is 0 and —(CH₂)ᵣ—OA⁴ attached to V² in formula (IV a) is also absent;

(iii) optionally adding a spacer phosphoramidite molecule to each of the branches of the brancher molecule using phosphoramidite chemistry, wherein said spacer molecule after addition results in structures preferably represented by general formula (V a)

(V a)

wherein independently at each occurrence
A⁵ is a suitable protecting group;
W is selected from the group consisting of —(CH₂)₂₋₁₅— and —CH₂CH₂(OCH₂CH₂)₀₋₄OCH₂CH₂—;
X¹ is —OH and X² is selected from =O and =S, or
X¹ is O⁻ and X² is selected from =O and =S, or
X¹ is =O and X² is selected from —CH₃, —SH, —OR, —NHR, and —BH₃, wherein R is independently at each occurrence a $C_1$-$C_6$ alkyl group, or
X¹ is =S and X² is selected from —CH₃ and —SH;

(iv) reacting a compound according to formula (I) with the reactive end of the nucleic acid molecule, if no brancher molecule is present, or reacting a compound according to formula (I) with the reactive end of each of the branches, if a brancher molecule is present and no spacer molecule is present, or reacting a compound according to formula (I) with the reactive end of each of the spacers, if spacers are present; and (v) cleaving the product of step (iv) from the solid support;

wherein the contiguous chain starting with the first atom of linker L in the compound according to formula (I), and ending with the attachment point in formula (IVa) or the attachment point in the nucleic acid molecule has a minimum length of 8 atoms and a maximum length of 30 atoms.

More particularly, the invention provides a process for the preparation of a nucleic acid conjugate, comprising the steps:

(i) providing a nucleic acid molecule on a solid support;
(ii) adding a brancher molecule to the nucleic acid molecule using phosphoramidite chemistry, wherein said brancher molecule after addition results in structures preferably represented by general formula (IV a)

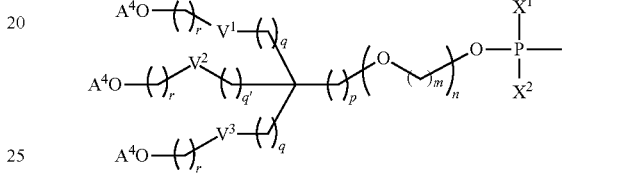

(IV a)

wherein
A⁴ is a suitable protecting group;
V¹ is selected from —O—, —NH—CO— and —CO—NH—;
V² is absent or is selected from —O—, —NH—CO— and —CO—NH—;
V³ is selected from —O—, —NH—CO— and —CO—NH—;
X¹ is —OH and X² is selected from =O and =S, or
X¹ is O⁻ and X² is selected from =O and =S, or
X¹ is =O and X² is selected from —CH₃, —SH, —OR, —NHR, and —BH₃, wherein R is independently at each occurrence a $C_1$-$C_6$ alkyl group, or
X¹ is =S and X² is selected from —CH₃ and —SH;
m is an integer from 1 to 3;
n is an integer from 0 to 5;
p is an integer from 0 to 3; and independently at each occurrence
q is an integer from 1 to 2;
q' is an integer from 0 to 2; and
r is an integer from 1 to 5;
with the proviso that when V² is absent, q' is 0 and —(CH₂)ᵣ—OA⁴ attached to V² in formula (IV a) is also absent;

(iii) reacting a compound according to formula (I) with the reactive end of each of the branches; and
(v) cleaving the product of step (iv) from the solid support;

wherein the contiguous chain starting with the first atom of linker L in formula (I) and ending with the attachment point in formula (IVa) has a minimum length of 8 atoms and a maximum length of 30 atoms.

In a preferred embodiment the linker L in formula (I) is selected from the group consisting of, —(CH₂)₆—, —(CH₂)₇—, —(CH₂)₈—, —(CH₂)₉—, —(CH₂)₁₀—, —(CH₂)₁₁—, —(CH₂)₁₂—, CH₂CH₂OCH₂CH₂OCH₂CH₂—, and —CH₂CH₂(OCH₂CH₂)₂OCH₂CH₂.

More particularly if the conjugate moiety in the GalNAc-nucleic acid conjugate is produced from a brancher and a compound according to formula (I), i.e. without a spacer, then q is 1; q' is 1; and r is 3 and L is —(CH$_2$)$_8$— or CH$_2$CH$_2$OCH$_2$CH$_2$OCH$_2$CH$_2$— or —(CH$_2$)$_5$ or CH$_2$CH$_2$OCH$_2$CH$_2$—.

More particularly if the conjugate moiety in the GalNAc-nucleic acid conjugate is produced from a doubler and a compound according to formula (I), i.e. without a spacer, then q is 1; q' is 1; and r is 3 and L is —(CH$_2$)$_8$— or CH$_2$CH$_2$OCH$_2$CH$_2$—.

More particularly if the conjugate moiety in the GalNAc-nucleic acid conjugate is produced from a trebler and a compound according to formula (I), i.e. without a spacer, then q is 1; q' is 1; and r is 3 and L is —(CH$_2$)— or CH$_2$CH$_2$OCH$_2$CH$_2$OCH$_2$CH$_2$—.

Alternatively, the process applies a brancher, a spacer, and a compound of formula (I). More particularly, the invention provides a process for the preparation of a nucleic acid conjugate, comprising the steps:

(i) providing a nucleic acid molecule on a solid support;

(ii) adding a brancher molecule to the nucleic acid molecule using phosphoramidite chemistry, wherein said brancher molecule after addition results in structures preferably represented by general formula (IV a)

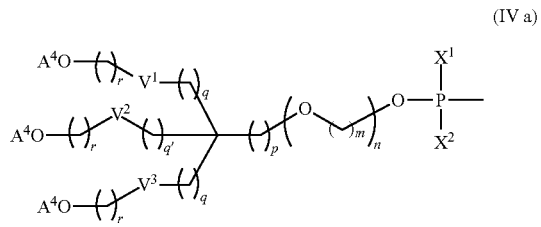

(IV a)

wherein
A$^4$ is a suitable protecting group;
V$^1$ is selected from —O—, —NH—CO— and —CO—NH—;
V$^2$ is absent or is selected from —O—, —NH—CO— and —CO—NH—;
V$^3$ is selected from —O—, —NH—CO— and —CO—NH—;
X$^1$ is —OH and X$^2$ is selected from =O and =S, or
X$^1$ is O$^-$ and X$^2$ is selected from =O and =S, or
X$^1$ is =O and X$^2$ is selected from —CH$_3$, —SH, —OR, —NHR, and —BH$_3$, wherein R is independently at each occurrence a C$_1$-C$_6$ alkyl group, or
X$^1$ is =S and X$^2$ is selected from —CH$_3$ and —SH;
m is an integer from 1 to 3;
n is an integer from 0 to 5;
p is an integer from 0 to 3; and independently at each occurrence
q is an integer from 1 to 2;
q' is an integer from 0 to 2; and
r is an integer from 1 to 5;
with the proviso that when V$^2$ is absent, q' is 0 and —(CH$_2$)$_r$—OA$^4$ attached to V$^2$ in formula (IV a) is also absent;

(iii) adding a spacer phosphoramidite molecule to each of the branches of the brancher molecule using phosphoramidite chemistry, wherein said spacer molecule after addition results in structures preferably represented by general formula (V a)

(V a)

wherein independently at each occurrence
A$^5$ is a suitable protecting group;
W is selected from the group consisting of —(CH$_2$)$_{2\text{-}15}$— and —CH$_2$CH$_2$(OCH$_2$CH$_2$)$_{0\text{-}4}$OCH$_2$CH$_2$—;
X$^1$ is —OH and X$^2$ is selected from =O and =S, or
X$^1$ is O$^-$ and X$^2$ is selected from =O and =S, or
X$^1$ is =O and X$^2$ is selected from —CH$_3$, —SH, —OR, —NHR, and —BH$_3$, wherein R is independently at each occurrence a C$_1$-C$_6$ alkyl group, or
X$^1$ is =S and X$^2$ is selected from —CH$_3$ and —SH;

(iv) reacting a compound according to formula (I) with the reactive end of each of the spacers; and (v) cleaving the product of step (iv) from the solid support;

wherein the contiguous chain starting with the first atom of linker L in formula (I) and ending with the attachment point in formula (IVa)) has a minimum length of 8 atoms and a maximum length of 30 atoms.

More particularly if the conjugate part in the nucleic acid conjugate is produced from a brancher where q is 1; q' is 1; and r is 3, a spacer where W is selected from —(CH$_2$)$_{2\text{-}5}$- or —CH$_2$CH$_2$OCH$_2$CH$_2$— or —CH$_2$CH$_2$OCH$_2$CH$_2$OCH$_2$CH$_2$— and a compound according to formula (I) where L is —(CH$_2$)$_{2\text{-}5}$- or CH$_2$CH$_2$OCH$_2$CH$_2$—. In preferred embodiments the W is —(CH$_2$)$_3$ and L is CH$_2$CH$_2$OCH$_2$CH$_2$—. In another preferred embodiment W is —(CH$_2$)$_3$ or —(CH$_2$)$_2$ and L is —CH$_2$CH$_2$OCH$_2$CH$_2$OCH$_2$CH$_2$—. In another preferred embodiment W is CH$_2$CH$_2$OCH$_2$CH$_2$OCH$_2$CH$_2$ and L is —(CH$_2$)$_3$— or —(CH$_2$)$_2$. In another preferred embodiment W is —(CH$_2$)$_3$— and L is —(CH$_2$)$_2$.

The nucleic acid molecule used in the generation of the GalNAc nucleic acid conjugates will be more extensively described below. Generally the nucleic acid molecule can be DNA, RNA or may comprise a nucleotide sequence which comprises both nucleosides and nucleoside analogues or is completely consisting of nucleoside analogues. The GalNAc conjugate moiety can either be built on to the 5'- or 3'-end of the nucleic acid molecule. Preferably, the GalNAc conjugation moiety is built on to the 5'-end of the nucleic acid molecule. In some embodiments a PO linker is placed between the nucleic acid and the GalNAc conjugate moiety.

Particularly, the nucleic acid molecule may contain one or more locked nucleic acid nucleosides.

Particularly, the nucleic acid molecule may contain one or more phosphorothioate or boranophosphate internucleoside linkages. Preferably, DNA and RNA nucleosides are linked with phosphorothioate or boranophosphate. More preferably all the nucleosides and/or nucleoside analogues in the nucleic acid molecule are linked with phosphorothioate or boranophosphate. In some embodiments, a GalNAc-nucleic acid conjugate can be made by coupling a GalNAc phosphoramidite according to formula (I) of the present invention directly to the 5'-end of a nucleic acid molecule, e.g. an oligonucleotide, as part of e.g. a sequential synthesis on solid support, using phosphoramidite chemistry. In these embodiments, no brancher or spacer molecules are added to the nucleic acid molecule.

By "phosphoramidite chemistry", a sequence of reactions is meant, which involves at least the following steps:

(a) deprotecting a protected hydroxy group, e.g. a 5-OH group of a nucleoside, or a linker moiety or the deprotecting the oxy group in $A^4$-O or $A^5$-O in formula (IV a) and (V a);

(b) coupling a phosphoramidite-containing compound, e.g. a GalNAc amidite according to the invention or a brancher molecule or a spacer molecule, to the unprotected hydroxy group (which may also be referred to as the "reactive end" of the respective molecule), and (c) oxidation of the intermediate.

Accordingly, when performing steps (ii), (iii) and (iv) of the process for the preparation of a GalNAc-nucleic acid conjugate, the protected hydroxy group or hydroxy groups of the nucleic acid (step (ii)), the brancher molecule (step (iii); e.g. $A^4O—$), and the spacer molecule(s) (step (iv); e.g. $A^5O—$), respectively, are deprotected before they are reacted further, i.e. before the brancher molecule in step (ii) is added, the spacer molecule in step (iii) is added or the compound according to formula (I) or formula (III) is added.

Suitable deprotection reactions are known to the skilled person in the field of organic synthesis.

In some embodiments of the process for the preparation of a GalNAc-nucleic acid conjugate, a brancher molecule is added to the nucleic acid molecule using phosphoramidite chemistry. After addition, the brancher molecule is preferably represented by general formula (IV a)

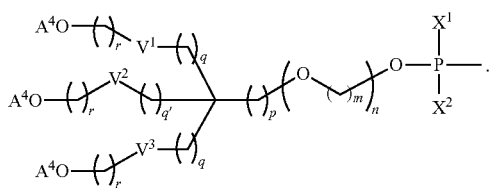

(IV a)

Within formula (IV a), $A^4$ is a suitable protecting group. Such protecting groups are known to the skilled person in the field of organic synthesis. For example, groups forming ethers with the free OH group may be mentioned. In certain preferred embodiments, the protecting group $A^4$ is dimethoxytrityl (DMT).

The variables $V^1$ and $V^3$ in formula (IV a) are independently selected from $—O—$, $—NH—CO—$ and $—CO—NH—$; in certain embodiments, they are both $—O—$; in other embodiments, they are both $—NH—CO—$.

The variable $V^2$ in formula (IV a) is absent or is selected from $—O—$, $—NH—CO—$ and $—CO—NH—$.

When $V^2$ is absent, q' is 0 and $—(CH_2)_r—OA^4$ attached to $V^2$ in formula (IV a) is also absent. In certain embodiments, $V^2$ is $—O—$; in other embodiments, $V^2$ is $—NH—CO—$.

In certain specific embodiments, all of $V^1$, $V^2$ and $V^3$ are $—O—$.

The variables $X^1$ and $X^2$ in formula (IV a) are selected from a number of different combinations:

In some embodiments $X^1$ is $—OH$ and $X^2$ is $=O$;
in other embodiments, $X^1$ is $—OH$ and $X^2$ is $=S$;
in still further embodiments, $X^1$ is $O^-$ and $X^2$ is $=O$;
in still further embodiments, $X^1$ is $O^-$ and $X^2$ is $=S$;
in still further embodiments, $X^1$ is $=O$ and $X^2$ is $—CH_3$;
in still further embodiments, $X^1$ is $=O$ and $X^2$ is $—SH$;
in still further embodiments, $X^1$ is $=O$ and $X^2$ is $—OR$, wherein R is a $C_1$-$C_6$ alkyl group, preferably methyl or ethyl;
in still further embodiments, $X^1$ is $=O$ and $X^2$ is $—NHR$,
wherein R is a $C_1$-$C_6$ alkyl group, preferably methyl or ethyl;
in still further embodiments, $X^1$ is $=O$ and $X^2$ is $—BH_3$;
in still further embodiments, $X^1$ is $=S$ and $X^2$ is $—CH_3$;
in still further embodiments, $X^1$ is $=S$ and $X^2$ is $—SH$.

In preferred embodiments, the variables $X^1$ and $X^2$ in formula (IV a) are selected from the group consisting of the following combinations:
$X^1$ is $—OH$ and $X^2$ is $=O$;
$X^1$ is $O^-$ and $X^2$ is $=O$;
$X^1$ is $—OH$ and $X^2$ is $=S$;
$X^1$ is $O^-$ and $X^2$ is $=S$; and
$X^1$ is $=S$ and $X^2$ is $—SH$.

In certain preferred embodiments, $X^1$ and $X^2$ are selected such that the group $—O—P(X^1X^2)—$ in formula (IV a), together with the hydroxy group to which it is attached, represents a phosphodiester group, a phosphorothioate group or a phosphorodithioate group.

The variable q' is an integer from 0 to 2, i.e. it represents 0, 1 or 2. In certain preferred embodiments, q'=q.

The variables m, n, p, q and r of formula (IV a) are defined as disclosed hereinabove with regard to formula (IV).

In some preferred specific embodiments of the invention, the brancher molecule is selected from the group consisting of:

1,3-bis-[5-(4,4'-dimethoxytrityloxy)pentylamido]propyl-2-[(2-cyanoethyl)-(N,N-diisopropyl)]phosphoramidite (Glen Research Catalogue Number: 10-1920-xx);

tris-2,2,2-[3-(4,4'-dimethoxytrityloxy)propyloxymethyl] ethyl-[(2-cyanoethyl)-(N,N-diisopropyl)]-phosphoramidite (Glen Research Catalogue Number: 10-1922-xx); and tris-2,2,2-[3-(4,4'-dimethoxytrityloxy)propyloxymethyl] methyleneoxypropyl-[(2-cyanoethyl)-(N,N-diisopropyl)]-phosphoramidite.

In another embodiment, the brancher may be 1-[5-(4,4'-dimethoxy-trityloxy)pentylamido]-3-[5-fluorenomethoxy-carbonyl-oxy-pentylamido]-propyl-2-[(2-cyanoethyl)-(N,N-diisopropyl)]-phosphoramidite (Glen Research Catalogue Number: 10-1925-xx).

In some embodiments, a spacer molecule is added to each of the branches of the brancher molecule using phosphoramidite chemistry. After addition, the spacer molecule is preferably represented by general formula (V a)

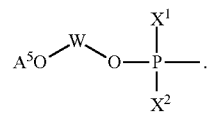

(V a)

Within formula (V a), $A^5$ is a suitable protecting group. Such protecting groups are known to the skilled person in the field of organic synthesis.

The protecting group $A^5$ may be independently selected at each occurrence. In preferred embodiments, however, the same protecting group is used for all spacers.

For example, groups forming ethers with the free OH group may be mentioned as suitable protecting groups $A^5$. In certain preferred embodiments, the protecting group $A^5$ is dimethoxytrityl (DMT).

The variable W in formula (V a) is selected from the group consisting of $—(CH_2)_{2-15}—$, i.e. $—(CH_2)_2—$, $—(CH_2)_3—$, $—(CH_2)_4—$, $—(CH_2)_5—$, $—(CH_2)_6—$, $—(CH_2)_7—$, $—(CH_2)_8—$, $—(CH_2)_9—$, $—(CH_2)_{10}—$, —(CH$_2$)$_{11}$—, —(CH$_2$)$_{12}$—, —(CH$_2$)$_{13}$—, —(CH$_2$)$_{14}$—, —(CH$_2$)$_{15}$—, and —CH$_2$CH$_2$(OCH$_2$CH$_2$)$_{0-4}$OCH$_2$CH$_2$—, i.e. —CH$_2$CH$_2$OCH$_2$CH$_2$—, —CH$_2$CH$_2$OCH$_2$CH$_2$OCH$_2$CH$_2$—, —CH$_2$CH$_2$(OCH$_2$CH$_2$)$_2$OCH$_2$CH$_2$—, —CH$_2$CH$_2$(OCH$_2$CH$_2$)$_3$OCH$_2$CH$_2$—, and —CH$_2$CH$_2$(OCH$_2$CH$_2$)$_4$OCH$_2$CH$_2$—. In a preferred embodiment, W is —(CH$_2$)$_8$— or CH$_2$CH$_2$OCH$_2$CH$_2$OCH$_2$CH$_2$—. In another preferred embodiment W is —(CH$_2$)$_5$— or —CH$_2$CH$_2$OCH$_2$CH$_2$—. In another preferred embodiment W is —(CH$_2$)$_2$— or —CH$_2$CH$_2$CH$_2$.

The variables $X^1$ and $X^2$ in formula (V a) are independently selected from the combinations defined with regard to $X^1$ and $X^2$ in formula (IV a) above.

In certain preferred embodiments, $X^1$ and $X^2$ are selected such that the group —O—P($X^1X^2$)— in formula (V a), together with the hydroxy group to which it is attached, represents a phosphodiester group, a phosphorothioate group or a phosphorodithioate group.

In some embodiments of the invention, the spacer phosphoramidite molecule is represented by general formula (VII)

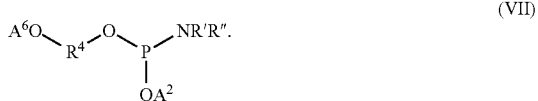

(VII)

R' and R" of the secondary amino group —NR'R" in formula (VII) are selected from $C_1$-$C_6$ alkyl or R' and R" together form a five- or six-membered ring, which may be substituted and which may contain one further heteroatom selected from N and O, wherein specific $C_1$-$C_6$ alkyl groups and rings are selected from those defined above with regard to formula (I). In particular embodiments, R' is identical to R", and —NR'R" is selected from the group consisting of dimethylamino, diethylamino, diisopropylamino, and dibutylamino, preferably diisopropylamino. In other embodiments, R' and R" together form a five- or six-membered ring as set forth above with regard to formula (I). In particular, the ring is selected from the group consisting of pyrrolidino, piperidino, 2,6-dimethylpiperidino, morpholino, imidazolyl and 4-methylimidazolyl.

As suitable protecting group $A^2$ in formula (VII) is a protected hydroxy group (—OH) or a protected thio group (—SH). Exemplary non-limited protected hydroxy groups are ether groups, exemplary non-limited protected thio groups are thioether groups. In particular, the protected —OH or —SH group represented by $A^2$ is selected from the group consisting of 2-cyanoethoxy, 2-cyanoethylthio, methoxy, ethoxy, S-isobutanoyl-2-(2-mercapto-ethoxy) ethoxy, S-pivaloyl-2-(2-mercapto-ethoxy)ethoxy, and S-pivaloyl-2-mercaptoethoxy.

Protecting group $A^6$ in formula (VII) may be independently selected at each occurrence: In preferred embodiments, however, the same protecting group is used for all spacers. For example, groups forming ethers with the free OH group may be mentioned as suitable protecting groups $A^6$. In certain preferred embodiments, the protecting group $A^6$ is dimethoxytrityl (DMT).

In certain preferred embodiments, $A^2$ is —CH$_2$CH$_2$CN, $A^6$ is 4',4'-Dimethoxytrityl, $R^4$ is selected from the group consisting of: —CH$_2$CH$_2$OCH$_2$CH$_2$OCH$_2$CH$_2$—, —CH$_2$CH$_2$(OCH$_2$CH$_2$)$_4$OCH$_2$CH$_2$—, —CH$_2$CH$_2$CH$_2$—, and —(CH$_2$)$_{12}$—; and NR'R" is a secondary amino group, wherein R' and R" are independently selected from $C_1$-$C_6$-alkyl or R' and R" together form a five- or six-membered ring, which may be substituted and which may contain one further heteroatom selected from N and O.

In preferred specific embodiments, $A^2$ is —CH$_2$CH$_2$CN, $A^6$ is 4',4'-Dimethoxytrityl, $R^4$ is —CH$_2$CH$_2$CH$_2$— and R' and R" are each isopropyl. In further preferred specific embodiments, $A^2$ is —CH$_2$CH$_2$CN, $A^6$ is 4',4'-Dimethoxytrityl, $R^4$ is —CH$_2$CH$_2$OCH$_2$CH$_2$OCH$_2$CH$_2$— and R' and R" are each isopropyl.

As already mentioned supra, the length of the backbone of the GalNAc-phosphoramidite shall not exceed a certain length. Accordingly, the compounds used in the process for the preparation of a GalNAc-nucleic acid conjugate according to the invention, the contiguous chain starting with the first atom of linker L in the compound according to formula (I), if no brancher and/or spacer molecules are used, and ending with the phosphorus atom linking the conjugate moiety to the nucleic acid, is defined as having a minimum length of 10 atoms and a maximum length of 34 atoms.

Similarly, in cases where a brancher and/or spacer molecules are added, the contiguous chain starting with the first atom of linker L in R1, R3 or, if R2 is not H, R2, and ending with the attachment point in formula (IV) has a minimum length of 8 atoms and a maximum length of 30 atoms.

The individual contiguous chains may vary in their length, but no single one of these contiguous chains is longer than 34 atoms. For example, the length of each of the contiguous chains may be independently 8, 9, 10, 12, 14, 16, 18, 20, 25, 30, 31, 32, 33 or 34 atoms in length starting with the first atom of linker L in the compound according to formula (I), if no brancher and/or spacer molecules are used, and ending with the phosphorus atom linking the conjugate moiety to the nucleic acid. The maximum length of the contiguous chain starting with the first atom of linker L in the compound according to formula (I), where no brancher and/or spacer molecules are present, is preferably 10, 12 atoms or 14 atoms. Preferably the length is between 10 and 34 atoms, more preferably between 10 and 30 atoms, more preferably between 14 and 26 atoms, even more preferably between 16 and 20 atoms.

In embodiments where brancher and/or spacer molecules are used, each of the contiguous chains starting with the first atom of linker L in $R^1$, $R^3$, and, if $R^2$ is not H, $R^2$, and ending with the attachment point in formula (IV), may be independently 8, 9, 10, 11, 12, 13, 14, 15, 16, 17, 18, 19, 20, 22, 24, 26, 28, 30 atoms in length. For example, each of the three contiguous chains may have a length of 14 atoms, 16 atoms or 18 atoms. Preferably the length is between 8 and 30 atoms, more preferably between 14 and 22 atoms, even more preferably between 16 and 20 atoms.

In some embodiments of the process for the preparation of a GalNAc-nucleic acid conjugate described herein, a branched conjugate moiety is added to the nucleic acid molecule via step (ii). In these embodiments, the contiguous chain starting with the first atom of linker L in the compound according to formula (I) and ending with the branching point carbon atom in formula (IV a)

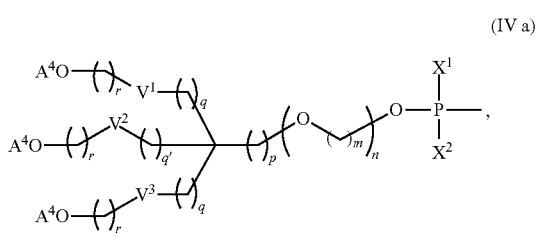

(IVa)

may preferably have a length of from 9 to 23 atoms.

Figure 1A:
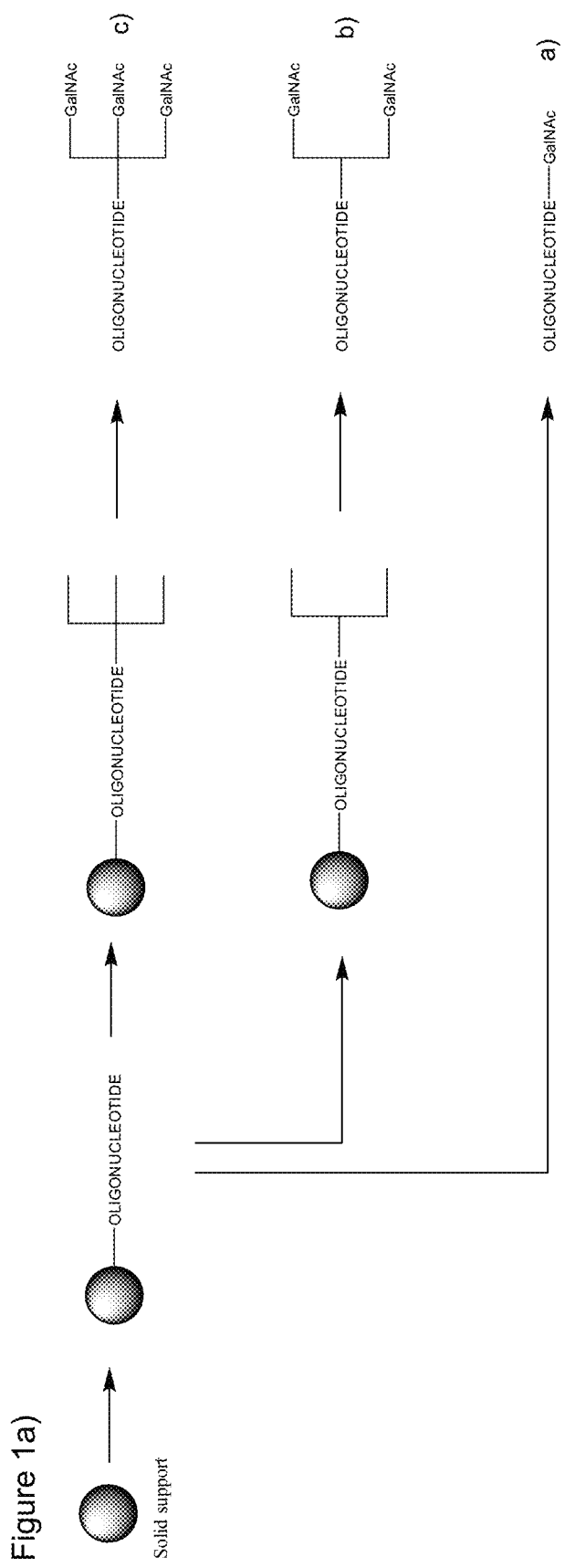
FIGS. 1a-b: Overview of solid phase synthesis of oligomers according to the invention.
Figure 1B:
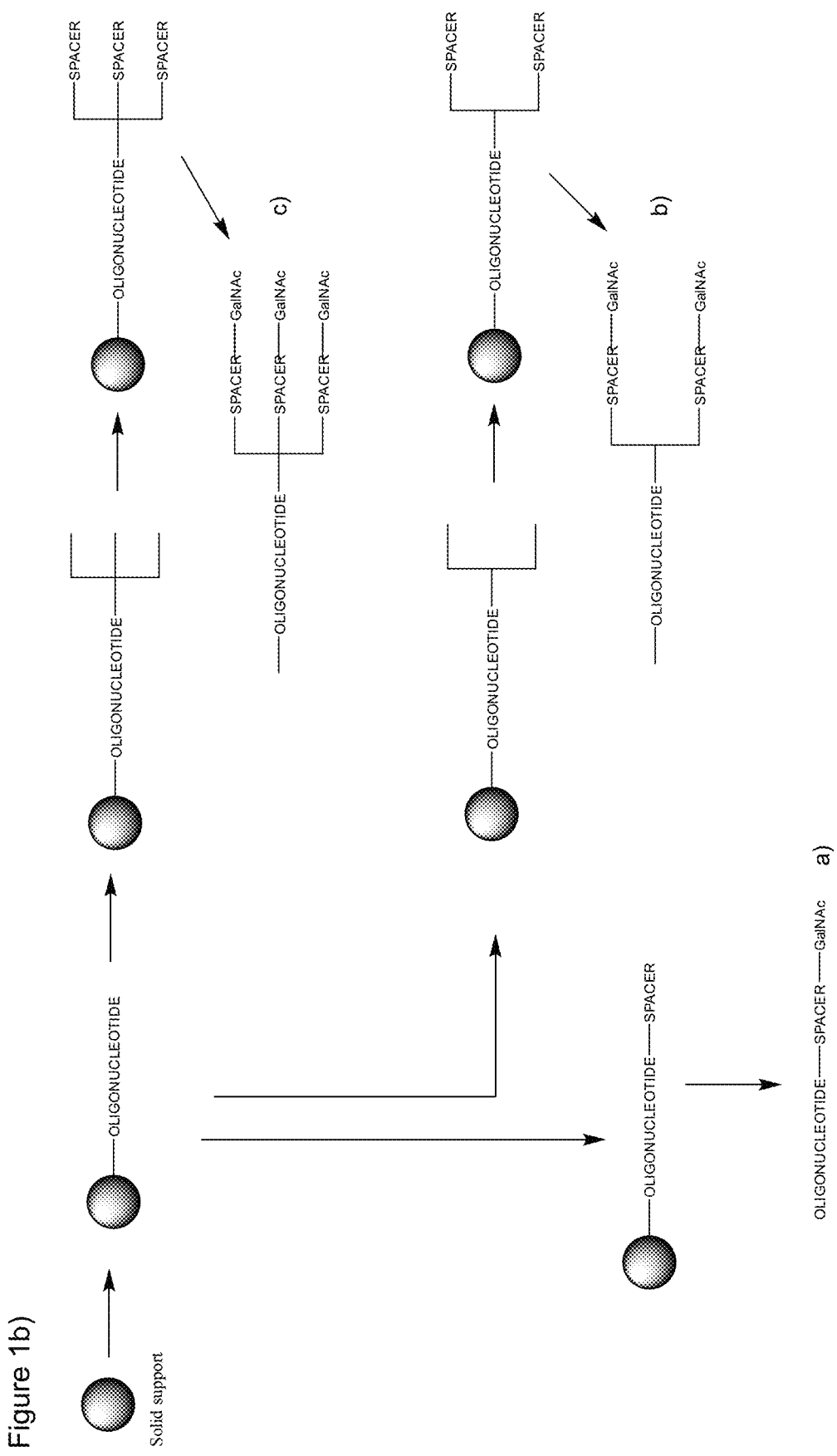

According to some embodiments of the invention, the GalNAc-nucleic acid conjugates, may be synthesized (on solid support using phosphoramidite chemistry) by the sequential synthesis of a nucleic acid followed by the addition of optionally a brancher and, optionally a spacer, and the GalNAc phosphoramidite and cleavage from the support (see FIG. 1 for an overview scheme).

The synthesis of exemplary GalNAc-nucleic acid conjugates is shown in FIG. 2.

Uses of the GalNAc Phosphoramidites and Compounds Derived from them

In yet a further aspect, the invention relates to various uses of the described novel GalNAc phosphoramidites. For example, the invention provides the use of a compound according to formula (I) for the preparation of GalNAc-nucleic acid conjugates. The conjugate moiety can be monovalent or a cluster. Preferably the clusters are divalent or trivalent with respect to GalNAc moieties. GalNAc-nucleic acid conjugates of the invention, i.e. compounds according to formula (III), with or without brancher and/or spacer molecule(s), preferably with brancher and/or spacer molecules can be produced using the GalNAc phophoramidites of the invention. In particular, a compound according to formula (I) may be used in the manufacturing process for GalNAc-nucleic acid conjugates described above.

In particular embodiments of the invention, conjugated GalNAc clusters can be used to facilitate drug delivery of the drug moiety conjugated to the GalNAc conjugate moiety. For example, drugs conjugated to a GalNAc conjugate moiety may have improved uptake to the liver compared to the unconjugated drug moiety. Suitable drugs may for example be nucleic acids capable of regulating a target gene or RNA in a cell or mammalian, e.g. single stranded oligonucleotides or siRNAs.

In yet a further aspect, the invention relates to medical uses of the compounds according to the invention. Accordingly, the invention provides the use of a compound according to formula (I) for use in delivering a medicine to the liver, in particular to a hepatocyte. Further, the invention provides the use of a compound according to formula (III) for use in medicine, particularly human medicine. In particular, the invention provides the use of a compound according to formula (III) as a medicament.

In particular embodiments, GalNAc-nucleic acid conjugates according to the invention, e.g. a nucleic acid conjugated to a trivalent (i.e. which has a brancher with three branches) GalNAc cluster is capable of binding to the asialoglycoprotein receptor (ASGPR), thereby allowing cellular uptake of the GalNAc-nucleic acid compounds of the invention.

Particularly, GalNAc nucleic acid conjugates according to the invention, e.g. LNA containing oligonucleotide conjugates, are for use in down-regulating a liver-expressed RNA. In particular for use in the prevention or treatment of a metabolic disease or disorder, or a hepatic disease or disorder. In particular for the treatment of diseases such as hepatitis (including viral hepatitis, such as HBV or HCV), hepatic steatosis (including metabolic malfunctions), atherosclerosis, hyperlipidemia, hypercholesterolemia, familiar hypercholesterolemia e.g. gain of function mutations in Apolipoprotein B, HDL/LDL cholesterol imbalance, dyslipidemias, e.g., familial hyperlipidemia (FCHL), acquired hyperlipidemia, statin-resistant hypercholesterolemia, coronary artery disease (CAD), and coronary heart disease (CHD), acute coronary syndrome (ACS), liver-fibrosis (or disease associated with liver-fibrosis), cirrhosis and cancer.

Further, the invention provides methods of treatment of liver diseases such as hepatitis (including viral hepatitis, such as HBV or HCV), hepatic steatosis (including metabolic malfunctions), atherosclerosis, hyperlipidemia, hypercholesterolemia, familiar hypercholesterolemia e.g. gain of function mutations in Apolipoprotein B, HDL/LDL cholesterol imbalance, dyslipidemias, e.g., familial hyperlipidemia (FCHL), acquired hyperlipidemia, statin-resistant hypercholesterolemia, coronary artery disease (CAD), and coronary heart disease (CHD), cirrhosis and cancer.

The Nucleic Acid Molecule

The term "nucleic acid molecule" in the context of the present invention, refers to a molecule formed by covalent linkage of two or more nucleosides (i.e. an oligonucleotide). Herein, a single nucleoside (unit) may also be referred to as a monomer or unit. In some embodiments, the terms "nucleoside", "nucleotide", "unit" and "monomer" are used interchangeably. It will be recognised that when referring to a sequence of nucleotides or monomers, what is referred to is the sequence of bases, such as A, T, G, C or U or analogues thereof.

The nucleic acid molecule can be DNA, RNA or may comprise a nucleotide sequence which comprises both nucleotides and nucleotide analogues. In particularly nucleic acid analogue molecules that modulate RNA within a cell are desired. The modulation can for example be facilitating degradation of mRNA, blockage of mRNA transcription, repair of splice sites, prevention of splicing or blockage of micro RNA.

The nucleic acid molecule may comprise or consist of a contiguous nucleotide sequence which corresponds to the reverse complement of the target nucleic acid. In some embodiments, the nucleic acid molecule may tolerate 1, 2, 3, or 4 (or more) mismatches, when hybridising to the target nucleic acid sequence and still sufficiently bind to the target to show the desired effect, i.e. down-regulation of the target. Mismatches may, for example, be compensated by increased length of the oligomer nucleotide sequence and/or an increased number of nucleotide analogues, such as LNA, present within the nucleotide sequence.

In some embodiments, the contiguous nucleotide sequence comprises no more than 3, such as no more than 2 mismatches when hybridizing to the target sequence, such as to the corresponding region of a nucleic acid which encodes a mammalian target protein.

In some embodiments, the contiguous nucleotide sequence comprises no more than a single mismatch when hybridizing to the target sequence, such as the corresponding region of a nucleic acid which encodes a mammalian target protein.

The nucleotide sequence of the nucleic acid molecules is preferably at least 80% identical to the reverse complement of a corresponding sequence present in the target nucleic acid, such as at least 85%, at least 90%, at least 91%, at least 92% at least 93%, at least 94%, at least 95%, at least 96% identical, at least 97% identical, at least 98% identical, at least 99% identical, such as 100% identical.

The term "complementary" means that two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Normally, the complementary sequence of the nucleic acid molecule has at least 80% complementary to a sub-sequence present in the target nucleic acid molecule, such as at least 85%, at least 90%, at least 91%, at least 92%, at least 93%, at least 94%, at least 95%, at least 96% complementary, at least 97% complementary, at least 98% complementary, at least 99% complementary, such as 100% complementary (perfectly complementary).

In determining the degree of complementarity between a nucleic acid molecule and the target nucleic acid sequence, the degree of complementarity is expressed as the percentage complementarity between the sequence of the nucleic acid molecule and the sequence of the target region that best aligns therewith. The percentage is calculated by counting the number of aligned bases that form pairs between the 2 sequences, dividing by the total number of monomers in the nucleic acid molecule (antisense oligonucleotide or siRNA), and multiplying by 100. In such a comparison a nucleobase/nucleotide which does not align is termed a mismatch. mRNA modulation can be facilitated through interaction with the RNA interference pathway machinery of the cell involving the RNAi-induced silencing complex (RISC). RNAi polynucleotides may be selected from the group comprising: siRNA, microRNA, double-strand RNA (dsRNA), short hairpin RNA (shRNA), and expression cassettes encoding RNA capable of inducing RNA interference.

siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. Preferably the conjugate of the invention is coupled to the sense strand of the siRNA. If a cleavable linker is present between the siRNA and the conjugate the conjugate can be linked to either the sense or antisense strand.

MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Blocking the seed region of the miRNA with an oligomer or facilitation of the binding of the RISC/miRNA complex to the mRNA can lead to either the repression of protein translation or cleavage and degradation of the mRNA.

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, HI promoters, and tRNA promoters. RNA polymerase II promoters include UI, U2, U4, and U5 promoters, snRNA promoters, microRNA promoters, and mRNA promoters.

Alternatively, RNA modulation can be facilitated by single stranded oligonucleotides complementary to the target mRNA or miRNA (antisense oligonucleotides). It is recognised that antisense oligonucleotides may function via non RNase mediated degradation of target mRNA, such as by steric hindrance of translation, or other methods, however, the preferred antisense oligonucleotides of the invention are capable of recruiting an endoribonuclease (RNase), such as RNase H.

EP 1 222 309 provides in vitro methods for determining RNase H activity, which may be used to determine the ability to recruit RNase H. An antisense oligonucleotide is deemed capable of recruiting RNase H if, when provided with the complementary RNA target, it has an initial rate, as measured in pmol/l/min, of at least 1%, such as at least 5%, such as at least 10% or more than 20% of the of the initial rate determined using DNA only oligonucleotide, having the same base sequence but containing only DNA monomers, with no 2' substitutions, with phosphorothioate linkage groups between all monomers in the oligonucleotide, using the methodology provided by Example 91-95 of EP 1 222 309.

In some embodiments, an antisense oligonucleotide is deemed essentially incapable of recruiting RNase H if, when provided with the complementary RNA target, and RNase H, the RNase H initial rate, as measured in pmol/l/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

In other embodiments, an antisense oligonucleotide is deemed capable of recruiting RNase H if, when provided with the complementary RNA target, and RNase H, the RNase H initial rate, as measured in pmol/l/min, is at least 20%, such as at least 40%, such as at least 60%, such as at least 80% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Typically the region of the oligomer which forms the consecutive nucleotide units which, when formed in a duplex with the complementary target RNA is capable of recruiting RNase consists of nucleotide units which form a DNA/RNA like duplex with the RNA target—and include both DNA units and LNA units which are in the alpha-L configuration, particularly preferred being alpha-L-oxy LNA.

The antisense oligonucleotide is a single stranded molecule, and preferably does not comprise short regions of, for example, at least 3, 4 or 5 contiguous nucleotides, which are complementary to equivalent regions within the same antisense oligonucleotide (i.e. duplexes)—in this regards, the antisense oligonucleotide is not (essentially) double stranded. In some embodiments, the antisense oligonucleotide is essentially not double stranded, such as is not a siRNA. In various embodiments, the antisense oligonucleotide of the invention may consist entirely of the contiguous nucleotide region. Thus, the antisense oligonucleotide is not substantially self-complementary. In various embodiments, the compound of the invention does not comprise RNA (units). It is preferred that the compound according to the invention is a linear molecule or is synthesised as a linear molecule.

The antisense oligonucleotide consists of or comprises a contiguous nucleotide sequence from 10-50, such as 10-30 nucleotides in length.

In some embodiments, the antisense oligonucleotides comprise or consist of a contiguous nucleotide sequence of a total of from 10-22, such as 10-16, such as 10-14, such as 11-20, such as 12-18, such as 12-16, such as 13-17, or such as 10, 11, 12, 13, 14, 15, 16. 17, 18, 19, 20, 21, 22, 23, 24, 25, 26, 27, 28, 29 or 30 contiguous nucleotides in length.

To recruit RNase H, the antisense oligonucleotide, or contiguous nucleotide sequence, may be in the form of a gapmer, a headmer or a mixmer.

A "headmer" is defined as an antisense oligonucleotide that comprises a region X and a region Y that is contiguous thereto, with the 5'-most monomer of region Y linked to the 3'-most monomer of region X. Region X comprises a contiguous stretch of non-RNase recruiting nucleoside analogues and region Y comprises a contiguous stretch (such as at least 7 contiguous monomers) of DNA monomers or nucleoside analogue monomers recognizable and cleavable by the RNase.

A "tailmer" is defined as an antisense oligonucleotide that comprises a region X and a region Y that is contiguous thereto, with the 5'-most monomer of region Y linked to the 3'-most monomer of the region X. Region X comprises a contiguous stretch (such as at least 7 contiguous monomers) of DNA monomers or nucleoside analogue monomers recognizable and cleavable by the RNase, and region X comprises a contiguous stretch of non-RNase recruiting nucleoside analogues.

A "mixmer" consists of an alternating composition of (i) DNA monomers or nucleoside analogue monomers recognizable and cleavable by RNase, and (ii) non-RNase recruiting nucleoside analogue monomers. Examples of mixmers can be found in WO2005/023995, hereby incorporated by reference.

Preferably, the antisense oligonucleotide of the invention is a gapmer. A gapmer antisense oligonucleotide is an antisense oligonucleotide which comprises a contiguous stretch of nucleotides which is capable of recruiting an RNAse, such as RNase H, such as a region of at least 6 or 7 DNA nucleotides, referred to herein in as region B, wherein region B is flanked both 5' and 3' by regions of affinity enhancing nucleotide analogues, such as from 1-6 nucleotide analogues 5' and 3' to the contiguous stretch of nucleotides which is capable of recruiting RNAse—these regions are referred to as regions A and A' respectively. The A and A' regions can also be termed the wings of the Gapmer.

Preferably, the gapmer comprises a (poly)nucleotide sequence of formula (5' to 3'), A-B-A', or optionally A-B-A'-PO or PO-A-B-A', wherein; region A (5' region wing) consists or comprises of at least one nucleoside analogue, such as at least one LNA unit, such as from 1-6 nucleoside analogues, such as LNA units, and; region B consists or comprises of at least five consecutive nucleotides which are capable of recruiting RNAse (when formed in a duplex with a complementary RNA molecule, such as the mRNA target), such as DNA nucleosides, and; region A' (3'region wing) consists or comprises of at least one nucleoside analogue, such as at least one LNA unit, such as from 1-6 nucleoside analogues, such as LNA units, and; region PO when present consists or comprises of 1-10 nucleoside units, preferably from 1-4 nucleoside units, such as DNA nucleotides.

In some embodiments, region A and A' consists independently of each other of 1, 2, 3, 4, 5 or 6 nucleoside analogues, such as LNA units, such as from 2-5 nucleoside analogues, such as 2-5 LNA units, such as 2-4 nucleoside analogues, such as 2-4 LNA, such as 3 or 4 nucleotide analogues, such as 3 or 4 LNA units.

In some embodiments B consists or comprises of 5, 6, 7, 8, 9, 10, 11 or 12 consecutive nucleotides which are capable of recruiting RNAse, or from 5-12, or from 6-10, or from 7-9, such as 8 consecutive nucleotides which are capable of recruiting RNAse. In some embodiments region B consists or comprises at least one DNA nucleoside unit, such as 1-12 DNA units, preferably from 4-12 DNA units, more preferably from 6-10 DNA units, such as from 7-10 DNA units, most preferably 8, 9 or 10 DNA units. In some embodiments, the monomers which are capable of recruiting RNAse are selected from the group consisting of DNA monomers, alpha-L-LNA monomers, C4' alkylayted DNA monomers (see PCT/EP2009/050349 and Vester et al., Bioorg. Med. Chem. Lett. 18 (2008) 2296-2300, hereby incorporated by reference), and UNA (unlinked nucleic acid) nucleotides (see Fluiter et al., Mol. Biosyst., 2009, 10, 1039 hereby incorporated by reference). In some embodiments the internucleoside linkages in the gapmer region B comprises one or more nucleoside linkages selected from the group consisting of phosphorothioate, phosphorodithioate and boranophosphate. Preferably all the internucleoside linkages of region B are phosphorothioate.

In some embodiments the gapmer is designed with one the following A-B-A' motifs 2-7-1, 1-7-2, 2-7-2, 3-7-3, 2-7-3, 3-7-2, 3-7-4, 4-7-3 or 1-8-1, 1-8-2, 2-8-1, 2-8-2, 3-8-2, 2-8-3, 3-8-2, 3-8-3, 3-8-4, 4-8-3, 4-8-1, 4-8-2, 1-8-4, 2-8-4, or 1-9-1, 1-9-2, 2-9-1, 2-9-2, 2-9-3, 3-9-2, 1-9-3, 3-9-1, 4-9-1, 1-9-4, 3-9-3, 3-9-4, 4-9-3, or; 1-10-1, 1-10-2, 2-10-1, 2-10-2, 1-10-3, 3- 10-1, 3-10-3, 3-10-4, 4-10-3. Further gapmer designs are disclosed in WO2004/046160 and WO2005/023825, which is hereby incorporated by reference. WO2007/146511 and WO2008/113832, hereby incorporated by reference, refers to 'shortmer' gapmer antisense oligonucleotides. In some embodiments, antisense oligonucleotides presented here may be such shortmer gapmers.

In some embodiments region PO is a biocleavable linker that comprise or consists of at least one DNA or RNA nucleosides linked to the 5' or 3' end of the antisense oligonucleotide via a phosphodiester linkage. In some aspects, the internucleoside linkage between the first and second region is considered as part of region PO. In some embodiments all the internucleoside linkages in region PO are phosphodiester linkage.

In some embodiments, the sequence of bases in region PO is selected to provide an optimal endonuclease cleavage site, based upon the predominant endonuclease cleavage enzymes present in the target tissue or cell or sub-cellular compartment.

In some embodiments region PO comprises a dinucleotide of sequence AA, AT, AC, AG, TA, TT, TC, TG, CA, CT, CC, CG, GA, GT, GC, or GG, wherein C may be 5-methylcytosine (also referred to as $^m$C), and/or T may be replaced with U. In some embodiments region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-methylcytosine and/or T may be replaced with U. In some embodiments region L' comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C, wherein C may be 5-methylcytosine and/or T may be replaced with U. It will be recognized that when referring to (naturally occurring) nucleobases A, T, U, G, C, these may be substituted with nucleobase analogues which function as the equivalent natural nucleobase (e.g. base pair with the complementary nucleoside).

An exemplary nucleic acid molecule that can be incorporated into the conjugates according to the invention is 5'-G$^m$CattggtatT$^m$CA-3' (capital letters=LNA monomers; lower case letters=DNA monomer).

The Target

The term "target" in the context of the present invention, refers to a naturally existing cellular or molecular structure within a cell, wherein the target is involved in a pathology of interest that the pharmaceutically active molecule is meant to act on. In preferred embodiments the target is a nucleic acid sequence (target nucleic acid) that upon modulation changes the pathology of interest.

The term "target nucleic acid", as used herein refers to a DNA or RNA encoding a mammalian target polypeptide, such as human a target polypeptide or a non-coding DNA or RNA molecule exerting a regulatory effect on mechanisms within a cell, such as viral infection mechanisms, RNA silencing or post-transcriptional regulation of gene expression. Non-coding RNA molecules can for example be micro RNA. In preferred embodiments the target nucleic acid is a gene, a messenger RNA (mRNA) or micro RNA (miRNA) present in a cell, such as a mammalian cell in particular a human cell in vitro or in vivo. In preferred embodiments the cell is a cell comprising asialoglycoprotein receptors (AS-PGR) on the surface, such as liver cells and testis cells, in particular hepatocytes and Leydig cells. In further preferred embodiments the target nucleic acid is mRNA, such as pre-mRNA, although preferably mature mRNA. Preferably the target mRNA or pre-mRNA is expressed in a liver cell. In some embodiments, for example when used in research or diagnostics the "target nucleic acid" may be a cDNA or a synthetic oligonucleotide derived from the above DNA or RNA nucleic acid targets. The nucleic acid molecule (e.g. siRNA or antisense oligonucleotide) is preferably capable of hybridising to the target nucleic acid.

Suitably the pharmaceutically active molecule, preferably a nucleic acid molecule, is capable of modulating down-regulating (e.g. reducing or removing) expression of the target nucleic acid. In this regards, the pharmaceutically active molecule of the invention can affect the inhibition of the target, typically in a mammalian such as a human cell. In some embodiments, the nucleic acid molecule bind to the target nucleic acid and affect inhibition of expression of at least 10% or 20% compared to the normal expression level, more preferably at least a 30%, 40%, 50%, 60%, 70%, 80%, 90% or 95% inhibition compared to the normal expression level (such as the expression level in the absence of the nucleic acid molecule or nucleic acid molecule conjugate. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR.

The invention therefore provides a method of modulating, e.g. down-regulating or inhibiting the expression or functionality of a protein and/or mRNA and/or microRNA in a cell comprising administering the nucleic acid molecule conjugate according to the invention to said cell to down-regulate or inhibit the expression or functionality of a target protein and/or mRNA and/or microRNA in said cell. Suitably the cell is a mammalian cell such as a human cell and preferably it is a liver cell. The administration may occur, in some embodiments, in vitro. The administration may occur, in some embodiments, in vivo. The administration of the composition is in an amount sufficient to be effective in treating or preventing a disorder or to regulate a physiological condition in humans.

The term "naturally occurring variant thereof" refers to variants of the target polypeptide of nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the target encoding genomic DNA which are found at the Chromosome by chromosomal translocation or duplication, and the RNA, such as mRNA derived therefrom. "Naturally occurring variants" may also include variants derived from alternative splicing of the target mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

Nucleosides and Nucleoside Analogues

In some embodiments, the terms "nucleoside analogue" and "nucleotide analogue" are used interchangeably.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In the field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifying the presence or nature of the linkages between the nucleosides.

As one of ordinary skill in the art would recognise, the 5' terminal nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleoside analogues" are variants of natural nucleosides, such as DNA or RNA nucleosides, by virtue of modifications in the sugar and/or base moieties. Analogues could in principle be merely "silent" or "equivalent" to the natural nucleosides in the context of the nucleic acid molecule, i.e. have no functional effect on the way the nucleic acid molecule works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the nucleic acid molecule works to inhibit expression; for example by producing increased binding affinity to the target and/or increased resistance to intracellular nucleases and/or increased ease of transport into the cell. Increased binding affinity to the target results in enhanced duplex stability of the nucleic acid molecule with the complementary RNA in term of a positive change in the melting temperature (ΔTm) of the duplex by at least +0.5° C. per modification, preferably by at least +1° C., 1.5° C., +2° C., +2.5° C., +3° C. per modification, more preferably by at least +4° C. per modification, most preferably by at least +4.5° C. per modification. Analogues providing such an affinity increase are also termed affinity-enhancing analogues. Specific examples of nucleoside analogues with a functional effect on the way in which the nucleic acid molecule works are described by e.g. Freier & Altmann; Nucl. Acid Res., 1997, 25, 4429-4443 and Uhlmann; Curr. Opinion in Drug Development, 2000, 3(2), 293-213, and shown below:

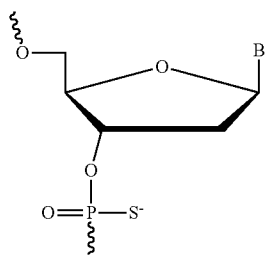

Phosphorthioate

-continued

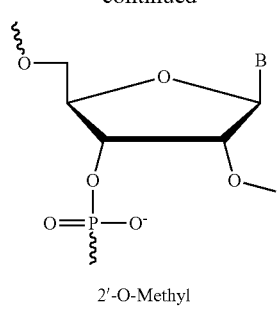

2'-O-Methyl

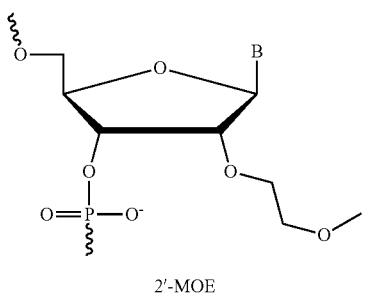

2'-MOE

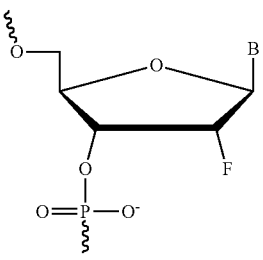

2'-Fluoro

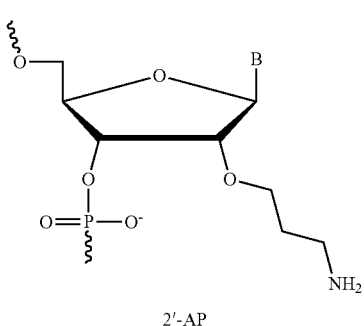

2'-AP

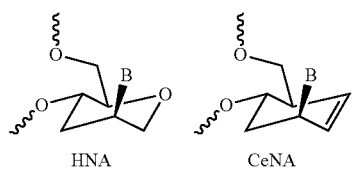

HNA          CeNA

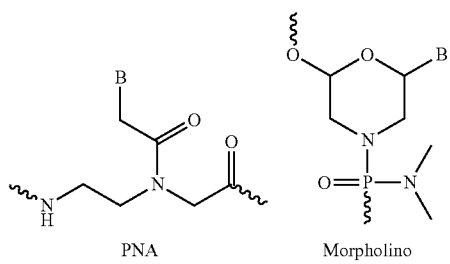

PNA          Morpholino

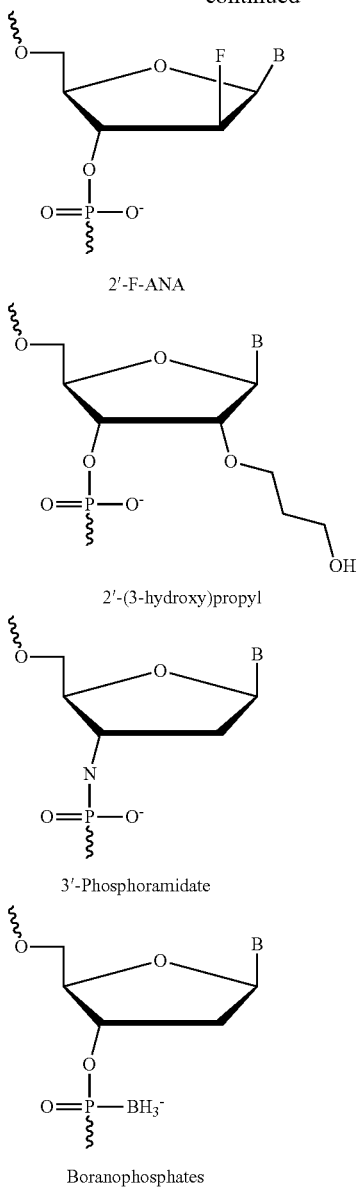

2'-F-ANA

2'-(3-hydroxy)propyl

3'-Phosphoramidate

Boranophosphates

The nucleic acid molecule may thus comprise or consist of a simple sequence of natural occurring nucleosides—preferably 2'-deoxynucleotides (referred to herein generally as "DNA"), but also possibly ribonucleotides (referred to herein generally as "RNA"), or a combination of such naturally occurring nucleosides and one or more non-naturally occurring nucleotides, i.e. nucleotide analogues. The natural occurring nucleosides may contain natural internucleoside linkages such as phophodiesters or stabilizing linkages such as phosphodiester, phosphorothioate or boranophosphate or a mixture of these linkages. Nucleotide analogues may suitably enhance the affinity of the nucleic acid molecule for the target sequence.

Examples of suitable and preferred nucleotide analogues are provided by WO2007/031091 or are referenced therein.

The term "LNA" refers to a bicyclic nucleoside analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a linker group (such as a bridge) between C2' and C4' of the ribose sugar ring—for example as shown as the biradical $R^{4*}$-$R^{2*}$ as described below.

The LNA used in the oligonucleotide compounds of the invention preferably has the structure of formula (VIII)

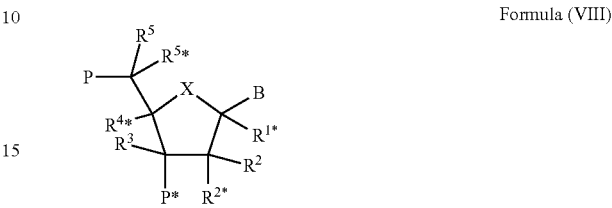

Formula (VIII)

wherein for all chiral centers, asymmetric groups may be found in either R or S orientation;

wherein X is selected from —O—, —S—, —N($R^{N*}$), C($R^6R^{6*}$)—, such as, in some embodiments —O—; B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue; P designates an internucleotide linkage to an adjacent monomer, or a 5-terminal group, such internucleotide linkage or 5-terminal group optionally including the substituent $R^5$ or equally applicable the substituent $R^{5*}$;

P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and; each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, C$_{2-12}$-alkoxyalkyl, C$_{2-12}$-alkenyloxy, carboxy, C$_{1-12}$-alkoxycarbonyl, C$_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene;

wherein R$^N$ is selected from hydrogen and C$_{1-4}$-alkyl, and where two adjacent (non-geminal) substituents may designate an additional bond resulting in a double bond; and R$^{N*}$, when present and not involved in a biradical, is selected from hydrogen and C$_{1-4}$-alkyl; and basic salts and acid addition salts thereof. For all chiral centers, asymmetric groups may be found in either R or S orientation.

In some embodiments, R$^{4*}$ and R$^{2*}$ together designate a biradical consisting of a groups selected from the group consisting of C(R$^a$R$^b$)—C(R$^a$R$^b$)—, C(R$^a$R$^b$)—O—, C(R$^a$R$^b$)—NR$^a$—, C(R$^a$R$^b$)—S—, and C(R$^a$R$^b$)—C(R$^a$R$^b$)—O—, wherein each R$^a$ and R$^b$ may optionally be independently selected. In some embodiments, R$^a$ and R$^b$ may be, optionally independently selected from the group consisting of hydrogen and C$_{1-6}$alkyl, such as methyl, such as hydrogen.

In some embodiments, R$^{4*}$ and R$^{2*}$ together designate the biradical —O—CH(CH$_2$OCH$_3$)— (2'O-methoxyethyl bicyclic nucleic acid—Seth at al., 2010, J. Org. Chem)—in either the R- or S-configuration.

In some embodiments, R$^{4*}$ and R$^{2*}$ together designate the biradical —O—CH(CH$_2$CH$_3$)— (2'O-ethyl bicyclic nucleic acid—Seth at al., 2010, J. Org. Chem).—in either the R- or S-configuration.

In some embodiments, R$^{4*}$ and R$^{2*}$ together designate the biradical —O—CH(CH$_3$)—.—in either the R- or S-configuration. In some embodiments, R$^{4*}$ and R$^{2*}$ together designate the biradical —O—CH$_2$—O—CH$_2$— (Seth at al., 2010, J. Org. Chem).

In some embodiments, R$^{4*}$ and R$^{2*}$ together designate the biradical —O—NR—CH$_3$——(Seth at al., 2010, J. Org. Chem).

In some embodiments, the LNA units have a structure selected from the following group:

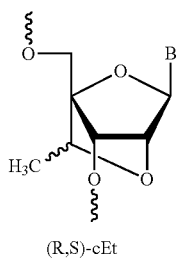

(R,S)-cEt

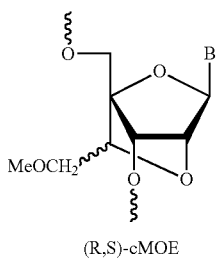

(R,S)-cMOE

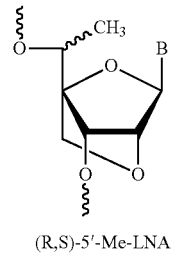

(R,S)-5'-Me-LNA

In some embodiments, R$^{1*}$, R$^2$, R$^3$, R$^5$, R$^{5*}$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$ alkoxyl, substituted C$_{1-6}$ alkoxyl, acyl, substituted acyl, C$_{1-6}$ aminoalkyl or substituted C$_{1-6}$ aminoalkyl. For all chiral centers, asymmetric groups may be found in either R or S orientation.

In some embodiments, R$^{1*}$, R$^2$, R$^3$, R$^5$, R$^{5*}$ are hydrogen.

In some embodiments, R$^{1*}$, R$^2$, R$^3$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$ alkoxyl, substituted C$_{1-6}$ alkoxyl, acyl, substituted acyl, C$_{1-6}$ aminoalkyl or substituted C$_{1-6}$ aminoalkyl. For all chiral centers, asymmetric groups may be found in either R or S orientation.

In some embodiments, R$^{1*}$, R$^2$, R$^3$ are hydrogen.

In some embodiments, R$^5$ and R$^{5*}$ are each independently selected from the group consisting of H, —CH$_3$, —CH$_2$—CH$_3$, —CH$_2$—O—CH$_3$, and —CH=CH$_2$. Suitably in some embodiments, either R$^5$ or R$^{5*}$ are hydrogen, whereas the other group (R$^5$ or R$^{5*}$ respectively) is selected from the group consisting of C$_{1-5}$ alkyl, C$_{2-6}$ alkenyl, C$_{2-6}$ alkynyl, substituted C$_{1-6}$ alkyl, substituted C$_{2-6}$ alkenyl, substituted C$_{2-6}$ alkynyl or substituted acyl (—C(=O)—); wherein each substituted group is mono or poly substituted with substituent groups independently selected from halogen, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, OJ$_1$, SJ$_1$, NJ$_1$J$_2$, N$_3$, COOJ$_1$, CN, O—C(=O)NJ$_1$J$_2$, N(H)C(=NH)NJ$_1$J$_2$ or N(H)C(=X)N(H)J$_2$ wherein X is O or S; and each J$_1$ and J$_2$ is, independently, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{1-6}$ aminoalkyl, substituted C$_{1-6}$ aminoalkyl or a protecting group. In some embodiments either R$^5$ or R$^{5*}$ is substituted C$_{1-6}$ alkyl. In some embodiments either R$^5$ or R$^{5*}$ is substituted methylene wherein preferred substituent groups include one or more groups independently selected from F, NJ$_1$J$_2$, N$_3$, CN, OJ$_1$, SJ$_1$, O—C(=O)NJ$_1$J$_2$, N(H)C(=NH)NJ, J$_2$ or N(H)C(O)N(H)J$_2$. In some embodiments each J$_1$ and J$_2$ is, independently H or C$_{1-6}$ alkyl. In some embodiments either R$^5$ or R$^{5*}$ is methyl, ethyl or methoxymethyl. In some embodiments either R$^5$ or R$^{5*}$ is methyl. In a further embodiment either R$^5$ or R$^{5*}$ is ethylenyl. In some embodiments either R$^5$ or R$^{5*}$ is substituted acyl. In some embodiments either R$^5$ or R$^{5*}$ is C(=O)NJ$_1$J$_2$. For all chiral centers, asymmetric groups may be found in either R or S orientation. Such 5' modified bicyclic nucleotides are disclosed in WO 2007/134181, which is hereby incorporated by reference in its entirety.

In some embodiments B in relation to nucleosides and nucleotides and analogues thereof, is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2'thiothymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^aR^b$)—N($R^c$)—, —C($R^aR^b$)—C($R^cR^d$)—N($R^e$)—, —C($R^aR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$). For all chiral centers, asymmetric groups may be found in either R or S orientation.

In a further embodiment $R^{4*}$ and $R^{2*}$ together designate a biradical (bivalent group) selected from —$CH_2$—O—, —$CH_2$—S—, —$CH_2$—NH—, —$CH_2$—N($CH_3$)—, —$CH_2$—$CH_2$—O—, —$CH_2$—CH($CH_3$)—, —$CH_2$—$CH_2$—S—, —$CH_2$—$CH_2$—NH—, —$CH_2$—$CH_2$—$CH_2$—, —$CH_2$—$CH_2$—$CH_2$—O—, —$CH_2$—$CH_2$—CH($CH_3$)—, —CH=CH—$CH_2$—, —$CH_2$—O—$CH_2$—O—, —$CH_2$—NH—O—, —$CH_2$—N($CH_3$)—O—, —$CH_2$—O—$CH_2$—, —CH($CH_3$)—O—, and —CH($CH_2$—O—$CH_3$)—O—, and/or, —$CH_2$—$CH_2$—, and —CH=CH— For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted C2-6 alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, OC(=X)$J_1$, OC(=X)$NJ_1J_2$, $NJ^3$C(=X)$NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$ alkyl. In some embodiments said substituent group is $C_{1-6}$ alkoxy. In some embodiments Z is $CH_3OCH_2$—. For all chiral centers, asymmetric groups may be found in either R or S orientation. Such bicyclic nucleotides are disclosed in U.S. Pat. No. 7,399,845, which is hereby incorporated by reference in its entirety. In some embodiments, $R^{1*}$, $R^2$, $R^3$, $R^5$, $R^{5*}$ are hydrogen. In some some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$ alkyloxy. In some embodiments $R^{4*}$ and $R^{2*}$ together designate a biradical -$Cq_3q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl; wherein each substituted group is, independently, mono- or poly-substituted with substituent groups independently selected from halogen, $OJ_1$, $SJ_1$, $NJ_1J_2$, $COOJ_1$, CN, O—C(=O)$NJ_1J_2$, N(H)C(=NH)N $J_1J_2$ or N(H)C(=X=N(H)$J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^aR^b$)—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$ $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C($q_3$)($q_4$); $q_3$ and $q_4$ are each, independently, H, halogen, $C_1$-$C_{12}$alkyl or substituted $C_1$-$C_{12}$ alkyl; each substituted group is, independently, mono or poly substituted with substituent groups independently selected from halogen, $C_1$—C alkyl, substituted $C_1$—C alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O) $NJ_1J_2$, N(H)C(=O)$NJ_1J_2$ or N(H)C(=S)$NJ_1J_2$, and; each $J_1$ and $J_2$ is, independently, H, C1-$C_6$ alkyl, substituted C1-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, C1-$C_6$ aminoalkyl, substituted C1-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is C($q_1$)($q_2$)C($q_3$)($q_4$), C($q_1$)=C($q_3$), C[=C($q_1$)($q_2$)]-C($q_3$)($q_4$) or C($q_1$)($q_2$)-C[=C($q_3$)($q_4$)]; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C (=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is C($q_1$)($q_2$)($q_3$)($q_4$) and one of $q_3$ or $q_4$ is $CH_3$ then at least one of the other of $q_3$ or $q_4$ or one of $q_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

Further bicyclic nucleoside analogues and their use in antisense oligonucleotides are disclosed in WO2011/115818, WO2011/085102, WO2011/017521, WO2009/100320, WO2010/036698, WO2009/124295 and WO2009/006478. Such nucleoside analogues may in some aspects be useful in the nucleic acid molecules of present invention.

In some embodiments the LNA used in the nucleic acid molecules preferably has the structure of the general formula (IX):

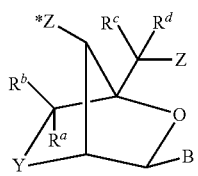

Formula (IX)

wherein Y is selected from the group consisting of —O—, —$CH_2O$—, —S—, —NH—, N($R^e$) and/or —$CH_2$—; Z and Z* are independently selected among an internucleotide linkage, RH, a terminal group or a protecting group; B constitutes a natural or non-natural nucleotide base moiety (nucleobase), and RH is selected from hydrogen and $C_{1-4}$-alkyl; $R^a$, $R^b$ $R^c$, $R^d$ and $R^e$ are, optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and RH is selected from hydrogen and $C_{1-4}$-alkyl. In some embodiments $R^a$, $R^b$ $R^c$, $R^d$ and $R^e$ are, optionally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

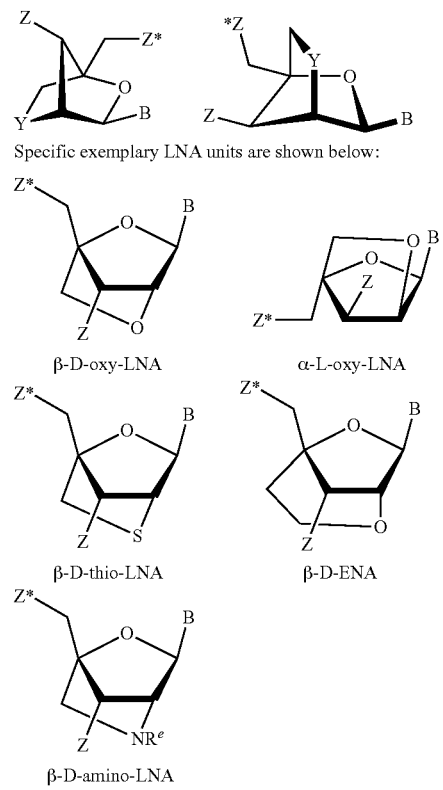

Specific exemplary LNA units are shown below:

β-D-oxy-LNA   α-L-oxy-LNA

β-D-thio-LNA   β-D-ENA

β-D-amino-LNA

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration.

The term "ENA" comprises a locked nucleotide in which Y in the general formula above is —$CH_2$—O— (where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Incorporation of affinity-enhancing nucleotide analogues in the nucleic acid molecule, such as LNA or 2'-substituted sugars, can allow the size of the specifically binding nucleic acid molecule to be reduced, and may also reduce the upper limit to the size of the nucleic acid molecule before non-specific or aberrant binding takes place.

In some embodiments, the nucleic acid molecule comprises at least 1 nucleoside analogue. In some embodiments the nucleic acid molecule comprises at least 2 nucleotide analogues. In some embodiments, the nucleic acid molecule comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the nucleic acid molecules of the invention which are defined by that sequence may comprise a corresponding nucleotide analogue in place of one or more of the nucleotides present in said sequence, such as LNA units or other nucleotide analogues, which raise the duplex stability/$T_m$ of the nucleic acid molecule/target duplex (i.e. affinity enhancing nucleotide analogues).

In some embodiments, any mismatches between the nucleotide sequence of the nucleic acid molecule and the target sequence are preferably found in regions outside the affinity enhancing nucleotide analogues, such as region B as referred to herein, and/or region L as referred to herein, and/or at the site of non-modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the nucleic acid molecule of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the nucleic acid molecule of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the nucleic acid molecule according to the invention comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA. In some embodiments, the nucleic acid molecule may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5'methyl-Cytosine. In some embodiments of the invention, the nucleic acid molecule may comprise both LNA and DNA units. Preferably the combined total of LNA and DNA units is 10-25, such as 10-24, preferably 10-20, such as 10-18, even more preferably 12-16. In some embodiments of the invention, the nucleotide sequence of the nucleic acid molecule, such as the contiguous nucleotide sequence consists of at least one LNA and the remaining nucleotide units are DNA units. In some embodiments the nucleic acid molecule comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring, as well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the nucleic acid molecule is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

Internucleotide Linkages

The monomers of the nucleic acid molecules described herein are coupled together via linkage groups. Suitably, each monomer is linked to the 3' adjacent monomer via a linkage group.

The person having ordinary skill in the art would understand that, in the context of the present invention, the 5' monomer at the end of an nucleic acid molecule does not comprise a 5' linkage group, although it may or may not comprise a 5' terminal group.

The terms "linkage group" or "internucleotide linkage" are intended to mean a group capable of covalently coupling together two nucleosides. Specific and preferred examples include phosphate groups and phosphorothioate groups.

The nucleosides of the nucleic acid molecule of the invention or contiguous nucleotide sequence thereof are coupled together via linkage groups. Suitably each nucleoside is linked to the 3' adjacent nucleoside via a linkage group.

Suitable internucleotide linkages include those listed within WO2007/031091, for example the internucleotide linkages listed on the first paragraph of page 34 of WO2007/031091 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. Phosphorothioate linkages may also be used for the flanking regions (A and A', and for linking A or A' to L, and within region L, as appropriate).

Regions A, B and A', may however comprise internucleotide linkages other than phosphorothioate, such as phosphodiester linkages, particularly, for instance when the use of nucleotide analogues protects the internucleotide linkages within regions A and A' from endonuclease degradation—such as when regions A and A' comprise LNA nucleotides.

The internucleotide linkages in the nucleic acid molecule may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the nucleic acid molecule of the invention, the nucleosides and/or nucleoside analogues are linked to each other by means of phosphorothioate groups.

It is recognised that the inclusion of phosphodiester linkages, such as one or two linkages, into an otherwise phosphorothioate nucleic acid molecule, particularly between or adjacent to nucleoside analogue units (typically in region A and or A') can modify the bioavailability and/or bio-distribution of a nucleic acid molecule—see WO2008/113832, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to specific gapmer antisense oligonucleotide sequences, such as those provided herein it will be understood that, in various embodiments, when the linkages are phosphorothioate linkages, alternative linkages, such as those disclosed herein may be used, for example phosphate (phosphodiester) linkages may be used, particularly for linkages between nucleoside analogues, such as LNA, units. Likewise, when referring to specific gapmer oligonucleotide sequences, such as those provided herein, when the C residues are annotated as 5'methyl modified cytosine, in various embodiments, one or more of the Cs present in the nucleic acid molecule may be unmodified C residues.

WO2009/124238 refers to oligomeric compounds having at least one bicyclic nucleoside attached to the 3' or 5' termini by a neutral internucleoside linkage. The nucleic acid molecules of the invention may therefore have at least one bicyclic nucleoside attached to the 3' or 5' termini by a neutral internucleoside linkage, such as one or more phosphotriester, methylphosphonate, MMI, amide-3, formacetal orthioformacetal. The remaining linkages may be phosphorothioate.

Compositions

The compounds of the invention may be used in pharmaceutical formulations and compositions. Suitably, such compositions comprise a pharmaceutically acceptable diluent, carrier, salt or adjuvant. WO2007/031091 provides suitable and preferred pharmaceutically acceptable diluent, carrier and adjuvants—which are hereby incorporated by reference. Suitable dosages, formulations, administration routes, compositions, dosage forms, combinations with other therapeutic agents, pro-drug formulations are also provided in WO2007/031091—which are also hereby incorporated by reference.

Applications

The compounds of the invention may be utilized as research reagents for, for example, diagnostics, therapeutics and prophylaxis.

In therapy compounds of the invention may be used to specifically modulate the synthesis of a target protein (typically by degrading or inhibiting the mRNA and thereby prevent protein formation) in a cell.

Alternatively, in therapy compounds of the invention may be used to modulate a non-coding DNA or RNA molecule exerting a regulatory effect on mechanisms within a cell in cells and experimental animals thereby facilitating functional analysis of the target or an appraisal of its usefulness as a target for therapeutic intervention.

In preferred embodiments the cell is a cell comprising asialoglycoprotein receptors (ASPGR) on the surface, such as liver cells and testis cells, in particular hepatocytes and Leydig cells.

For therapeutics, an animal or a human, suspected of having a disease or disorder, which can be alleviated or treated by modulating a DNA or RNA encoding a mammalian target polypeptide, such as human a target polypeptide or by modulating a non-coding DNA or RNA molecule exerting a regulatory effect on mechanisms within a cell, such as viral infection mechanisms, RNA silencing or post-transcriptional regulation of gene expression. Non-coding RNA molecules can for example be micro RNA. In preferred embodiments the target nucleic acid is a gene, a messenger RNA (mRNA) or micro RNA (miRNA).

Further provided are methods of treating a mammal, such as treating a human, suspected of having or being prone to a disease or condition, by administering a therapeutically or prophylactically effective amount of one or more of the compounds or compositions of the invention. The nucleic acid conjugate or a pharmaceutical composition according to the invention is typically administered in an effective amount.

In particular compounds of formula (III) may be used in the applications of the invention.

The invention also provides for the use of the compound or conjugate of the invention as described for the manufacture of a medicament for the treatment of a disorder or for a method of the treatment of as a disorder affected by the modulation of a target nucleic acid.

The invention also provides for a method for treating a disorder, said method comprising administering a compound according to the invention and/or a pharmaceutical composition according to the invention to a patient in need thereof.

Examples of disorders to be treated are liver diseases such as hepatitis (including viral hepatitis, such as HBV or HCV), hepatic steatosis, atherosclerosis, hyperlipidemia, hypercholesterolemia, familiar hypercholesterolemia e.g. gain of function mutations in Apolipoprotein B, HDL/LDL cholesterol imbalance, dyslipidemias, e.g., familial hyperlipidemia (FCHL), acquired hyperlipidemia, statin-resistant hypercholesterolemia, coronary artery disease (CAD), and coronary heart disease (CHD), cirrhosis and cancer.

The invention is further illustrated by the following examples.

EXAMPLES

Example 1: Synthesis of GalNAc Phosphoramidites

Synthesis of beta-GalNAc Phophoramidites

Step 1

tert-butyldiphenylsilylchloride (TBDPSCl) (2.6 mL, 10 mmol) was added dropwise to a mixture of ethyleneglycol (3.4 mL, 60.7 mmol) and pyridine (3.4 mL, 42.2 mmol) at room temperature. After stirring for 3.5 hours, the reaction mixture was diluted with EtOAc (50 mL). The organic phase was extracted with water (30 mL), 20% $NaHCO_3$ (30 mL), brine (30 ml), dried over $Na_2SO_4$ and evaporated. The residue was purified by DCVC chromatography (eluent EtOAc in hexanes from 10% to 25%). Product (TBDPS glycol) was isolated as a white solid, 2.54 g, yield 84%.

Step 2

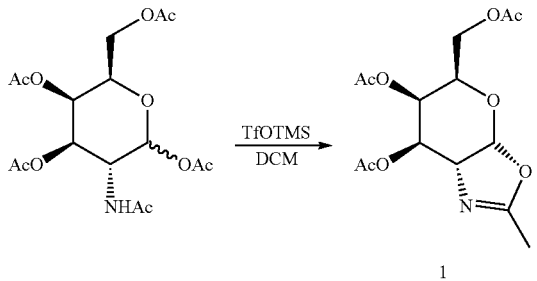

To suspension of peracetylated galactosamine (1.63 g, 4.17 mmol) in 30 mL DCM. TMSOTf (1.90 mL, 10.4 mmol) was added and reaction mixture stirred at 40-45° C. for 5 h. An additional portion of TMSOTf (0.30 mL 2.8 mmol) was added and the reaction mixture was stirred for additional 16 h. Then the reaction was quenched with $NEt_3$ (0.90 mL) at 0° C. and diluted with DCM, extracted with cold sat. $NaHCO_3$ (2×100 mL), brine (50 mL), dried over $Na_2SO_4$ and evaporated. Product 1 isolated as a yellow oil, 1.40 g crude yield.

Step 3

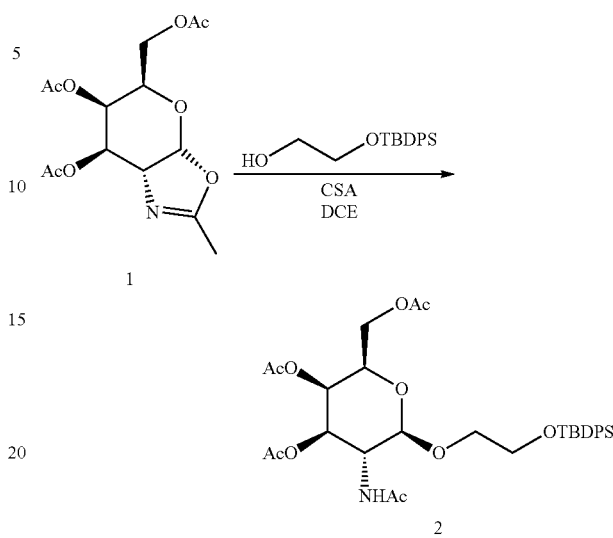

1 (1.40 g, 4.17 mmol) and TBDPS glycol (1.08 g, 1.60 mmol) was dissolved in 20 mL DCE. Camphor-sulfonic acid (CSA) (84 mg, 0.36 mmol) was added and the reaction mixture was stirred at 70-75° C. for 2 hours. Additional CSA (84 mg, 0.36 mmol) was added and the reaction mixture was stirred at 70-75° C. for additional 2 hours. $NEt_3$ (80 L) was added to the reaction mixture at room temperature and then it was diluted with DCM (20 mL). The mixture was washed with sat. $NaHCO_3$ (100 mL), water (100 ml), brine (50 mL), and the organic phase was dried over $Na_2SO_4$ and evaporated. The resulting residue was purified by column chromatography (eluent: EtOAc in hexanes from 30% to 50%). The product was isolated as a white foam (1.59 g, yield 70%), $^1$H-NMR and MS, HPLC 99%

Step 4

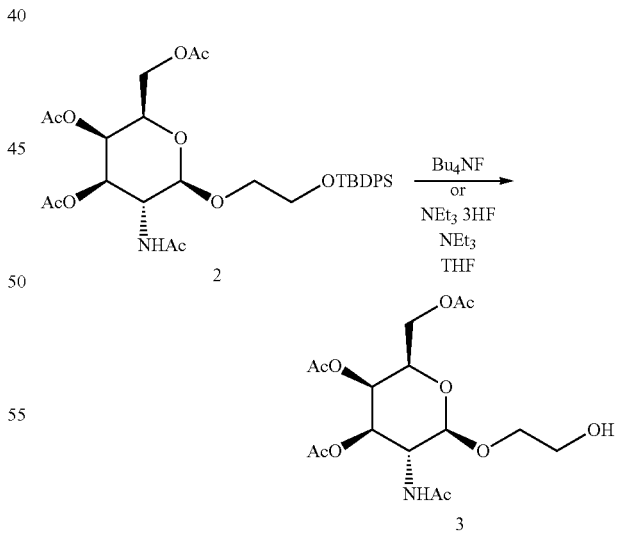

$NEt_3$*3HF (1.2 mL, 7.4 mmol) was added to a solution of 2 (776 mg, 1.23 mmol) and $NEt_3$ (0.44 mL, 3.07 mmol) in 12 mL THF. The reaction mixture was stirred and room temperature for 20 hours, and then evaporated. The residue was purified by column chromatography (eluent MeOH in DCM from 4% to 10%). 3 was isolated as a white solid 416 mg, yield 86%, $^1$H-NMR.

Step 5

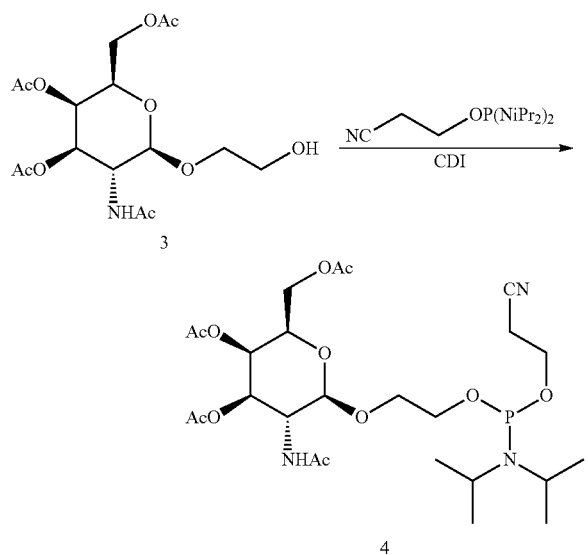

To a solution of 3 (1.51 g, 3.87 mmol) in DCM (60 mL) and MeCN (4 mL) a solution of DCI (320 g, 2.71 mmol) in MeCN (2 mL) was added followed by addition of a solution of PN2 (1.42 g, 4.47 mmol) in DCM (2.5 mL). The reaction mixture stirred at room temperature for 4 h. DCM (30 mL) was added and the reaction mixture was washed with $NaHCO_3$ (2×100 mL), water/brine 1/1 (50 mL), dried over $Na_2SO_4$, and evaporated. The residue was purified by column chromatography (eluent DCM+3% $NEt_3$) and then purified by a second column chromatography (EtOAc/hexanes).

The product was isolated as a yellow oil (1.02 g, yield 44%). $^{31}$P-NMR (160 MHz): (DMSO-$d_6$) δ: 147.5, 147.1. $^1$H-NMR (400 MHz): (DMSO-$d_6$) δ: 7.80 (1H, d, J=9.0 Hz), 5.22 (1H, d, J=3.1 Hz), 4.97 (1H, dd, J=11.3, 3.1 Hz), 4.57 (1H, dd, J=9.0, 1.6 Hz), 4-08-3.99 (3H, m), 3.98 (1H, m), 3.83-3.50 (8H, m), 2.81-2.71 (2H, m), 2.10 (3H, s). 1.99 (3H, s), 1.89 (3H, s), 1.77 (3H, d, J=1.6 Hz), 1.17-1.09 (12H, m). $^{13}$C-NMR (100 MHz): (DMSO-$d_6$) δ: 170.41, 170.33, 170.04, 169.64, 119.44, 101.37, 70.92, 70.33, 69.13, 67.14, 62.34, 62.17, 61.89, 58.86, 58.69, 49.70, 42.94, 42.92, 42.82, 42.80, 24.84, 24.78, 24.76, 24.70, 23.26, 23.23, 20.94, 20.87, 20.84, 20.29, 20.22.

See also FIG. 3a-c.

Synthesis of TEG Beta-GalNAc Phosphoramidite

Step 6

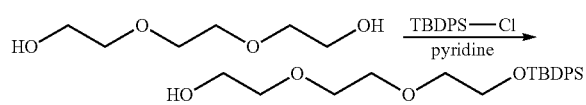

TBDPSCl (9.1 mL, 35 mmol) was added dropwise to a mixture of ethyleneglycol (28.4 mL, 210 mmol) and pyridine (11.3 mL) at room temperature. After stirring for 2 h the reaction mixture was diluted with EtOAc (150 mL), extracted with water (100 mL), brine (100 ml), dried over $Na_2SO_4$ and evaporated. The residue was purified by DCVC chromatography (eluent EtOAc in hexanes form 10% to 30%). TBDPS triethyleneglycol isolated as viscous oil, 10.7 g, yield 79%.

Step 7

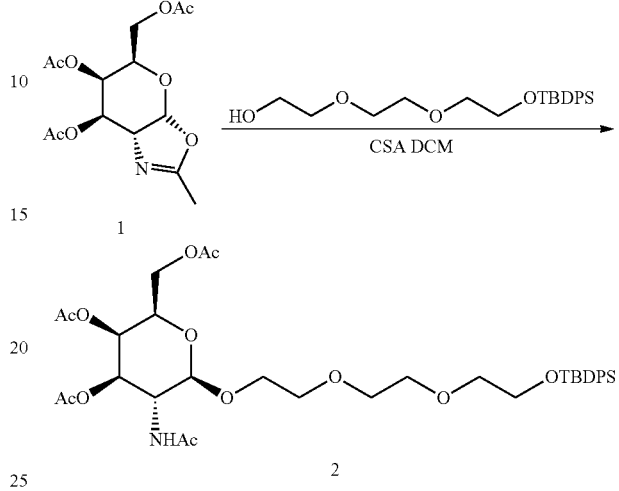

To a mixture of 1 (app 7.4 g, 20.6 mmol) and TBDPS triethyleneglycol (6.68 g, 17.2 mmol) in DCE (130 mL), camphor-sulfonic acid (CSA, 0.40, 1.72 mmol) was added and the reaction mixture was stirred at 70-75° C. for 18 h. $NEt_3$ (0.48 mL) was added to the reaction mixture at room temperature, then diluted with DCM (80 mL), extracted with sat. $NaHCO_3$ (2×100 mL), water (100 ml), brine (100 mL), dried over $Na_2SO_4$ and evaporated. Residues were purified by chromatography (eluent EtOAc in hexanes from 66% to 80%). 2 was isolated as slightly yellow oil 8.90 g, $^1$H-NMR, MS [M+1]$^+$718, HPLC purity 95%, yield 69%,

Step 8

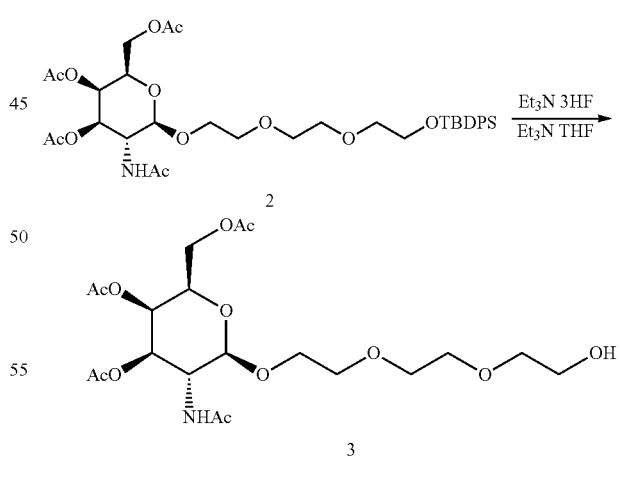

To solution of 2 (8.90 g, 12.4 mmol) in THF (125 mL), $NEt_3$ (4.3 mL, 31 mmol) and $NEt_3$ 3HF (12 mL, 74 mmol) was added. The reaction mixture was stirred at room temperature for 24 h, then evaporated. The residue was purified by column chromatography (eluent MeOH in DCM from 4% to 9%). 3 was isolated as a slightly yellow oil 4.40 g, H-NMR, yield 71%, Step 9

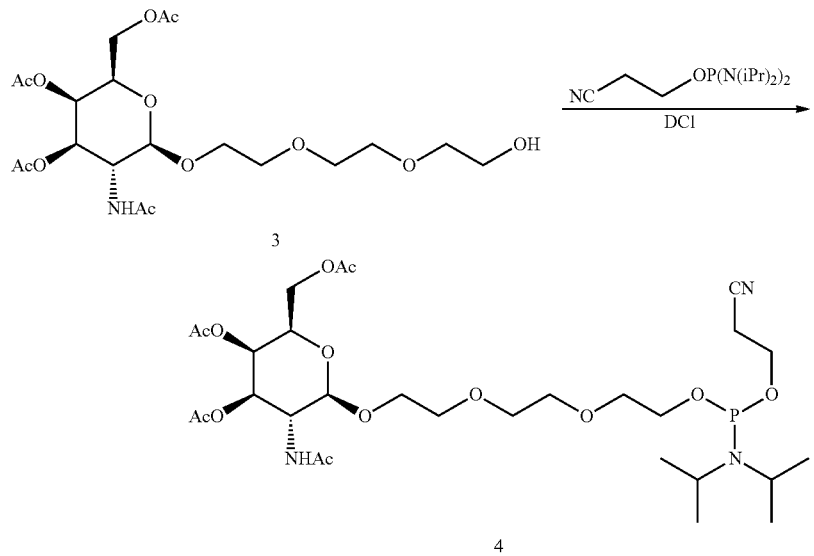

To solution of 3 (4.4 g, 9.18 mmol) in DCM (100 mL) and MeCN (3.5 mL) solution of DCI in MeCN (6 mL) was added followed with solution of PN2 (3.18, 10.6 mmol) in DCM (5 mL). The reaction mixture stirred at room temperature for 22 h (not full conversion). DCM (45 mL) was added and the reaction mixture was extracted with NaHCO$_3$ (2×100 mL), water/brine 1/1 (50 mL), dried over Na$_2$SO$_4$ and evaporated. The residue was purified by column chromatography (eluent EtOAc/hexanes 1/4+9% NEt$_3$). 1.52 g of 3 was regenerated, converted to 4 by the same method (PN$_2$ 1.09 g 3.64.6 mmol, 0.26 g 2.22 mmol, DCM 35 mL, MeCN 3.5 mL, reaction time 24 h) and purified together with impure fraction from the first chromatography. 4 was isolated as slightly yellow oil 2.45 g yield 38%, $^{31}$P-NMR (160 MHz): (DMSO-d$_6$) δ: 147.3; $^1$H-NMR (400 MHz): (DMSO-d$_6$) δ: 7.79 (1H, d, J=9.0 Mz), 5.21 (1H, d, J=3.5 Hz), 4.97 (1H, dd, J=11.3, 3.5 Hz), 4.55 (1H, d, J=8.6 Hz), 4.11-3.97 (3H, m), 3.88 (1H, m), 3.81-3.47 (16H, m), 2.78-2.74 (2H, m), 2.11 (3H, s), 2.00 (3H, s), 1.89 (3H, s), 1.77 (3H, s), 1.16-1.10 (12H, m). MS [M+1]$^+$680.5.

See also FIG. 3d-e

Alternative Synthesis of an Anomeric Mixture of GalNAc Phosphoramidites

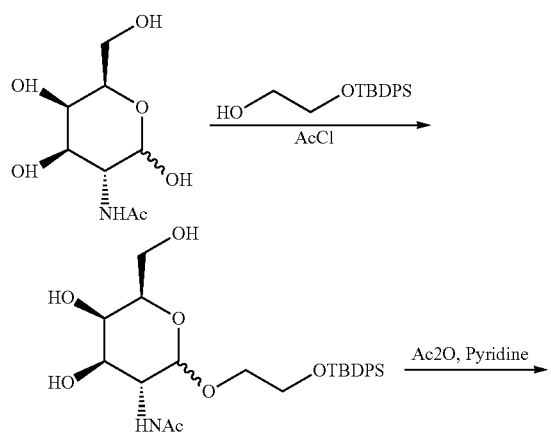

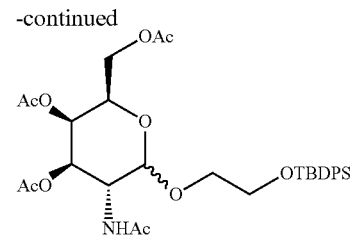

-continued

Acetyl chloride is added dropwise to a solution of NAc-Gal and TBDPS glycol in DMF at 0° C. The reaction mixture is stirred at 70° C. until completion. The reaction mixture is cooled 0° C. and quenched with excess anh, pyridine. The reaction mixture is allow to reach room temperature and excess acetic anhydride is added. The mixture is stirred until completion. Based on Medina et al, Biomaterials 32 (2011), 4118-4129 (hereby incorporated by reference).

This composition can be subjected to reactions steps 4 and 5 above to obtain a anomeric mixture of GalNAc phosphoramidites, i.e. containing both alpha- and beta-GalNAc. If an alpha-GalNAc phosphormamidite is desired this can be purified from the anomeric mixture.

Example 2: Synthesis of Oligonucleotides Using GalNAc Phosphoramidite Incorporation Oligonucleotides were synthesized on NittoPhase Unylinker 200 supports using the phosphoramidite approach at 20 µmol scale. At the end of the synthesis, the oligonucleotides were cleaved from the solid support using concentrated ammonium hydroxide for 16 hours at 60° C. The oligonucleotides were purified by reverse phase HPLC and characterized by UPLC, and the molecular mass was further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T, GalNAc phosphoramidite X and Y and spacer phosphoramidite C3 and spacer 18 (Glen Research, Sterling, Va.) was performed by using a solution of 0.1 M of phosphoramidite in acetonitrile and DCI (4,5-dicyanoimidazole) in acetonitrile (0.25 M) as activator. Thiolation for introduction of phosphorthioate linkages was carried out using xanthane hydride (0.01 M in acetonitrile/pyridine 9:1). Phosphordiester linkages were introduced using 0.02 M iodine in THF/Pyridine/water 7:2:1. The rest of the reagents were the ones typically used for oligonucleotide synthesis.

Purification by RP-HPLC:

The crude compounds were purified by preparative reversed phase HPLC on a Phenomenex Jupiter C18 10μ 150×10 mm column. 0.1 M ammonium acetate pH 8 and acetonitrile was used as buffers at a flow rate of 5 mL/min. The collected fractions were lyophilized to give the purified compound typically as a white solid.

The GalNac-nucleic acid compounds in table 1 have been synthesized using the following oligonucleotide sequences 5'G$^m$CattggtatT$^m$CA-3' (SEQ ID NO: 1) or 5' caG$^m$CattggtatT$^m$CA-3' (SEQ ID NO: 2). All linkages in SEQ ID NO: 1 were phosphothioate linkages. In SEQ ID NO: 2 the first two nucleosides (ca) are linked by phospohodiester linkages the remaining linkages are phosphothioate linkages. Capital letters denote LNA monomers ($^m$C is 5-methylcytosine LNA monomer) and lower case letters is DNA monomers.

TABLE 1

| Compound as shown in FIG. 6 | GalNAc construct | Chain length | Oligonucleotide sequence | Calc. mass | Found mass |
|---|---|---|---|---|---|
| B | monovalent | 8 | SEQ ID NO: 1 | 4668.8 | 4668.4 (FIG. 4) |
| E | trivalent | 10 | SEQ ID NO: 2 | 6339.2 | 6338.8 |
| I | trivalent | 16 | SEQ ID NO: 2 | 6604.2 | 6602.6 |
| M | trivalent | 16 | SEQ ID NO: 2 | 6754.0 | 6755.0 |
| N | trivalent | 30 | SEQ ID NO: 2 | 7371.5 | 7371.3 |
| Control | No | 0 | SEQ ID NO: 1 | | |
| GalNAc2 | trivalent | 16 | SEQ ID NO: 1 | | |

The control compound is the unconjugated oligonucleotide of SEQ ID NO: 1 (i.e. without any GalNAc moieties attached). The GalNAc2 compound is SEQ ID NO: 1 attached to the GalNAc2 cluster shown below, the oligonucleotide is indicated as the wavy line and is connected to the GalNAc2 construct with a phosphoethioate group. Oligonucleotides conjugated to the GalNAc2 cluster are described in WO 2014/118267 and the compound corresponds to SEQ ID NO: 20 in WO 2014/076196 (hereby incorporated by reference).

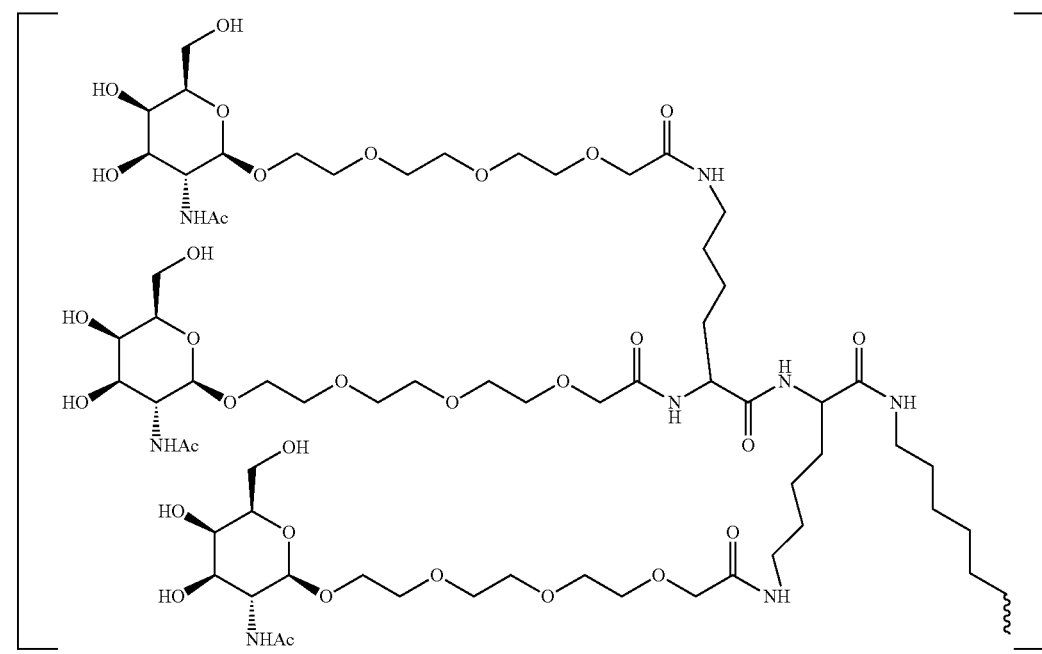

Example 3: Knock Down of ApoB mRNA and Total Cholesterol with GalNAc-Conjugates In Vivo To compare the effect of different GalNAc constructs C57BL6/J mice were injected sc with a single dose saline or 0.25 mg/kg GalNAc cluster conjugated LNA-antisense oligonucleotide (GalNAc2) or equimolar amounts of LNA antisense oligonucleotides conjugated to the GalNAc constructs of the invention (FIGS. 6 E, I, M and N) or unconjugated LNA antisense oligonucleotide (see Example 2, table 1 for details) and sacrificed at days 10 where liver and kidney were isolated.

Each compound was tested in an animal group containing five mice with weight of approximately 20 g. Serum samples were collected at day 3 and 7 (50 microL/mouse) and at sacrifice total serum was collected for determination of total serum cholesterol as described in protocol below. The results are shown in FIG. 8.

At sacrifice RNA was isolated from liver and kidney and subjected to qPCR with ApoB specific primers and probe to analyze for ApoB mRNA knockdown as described in the protocol below. The results are shown in FIG. 7.

CONCLUSIONS

All GalNAc conjugated LNA oligonucleotides showed improved knock down in the liver of ApoB mRNA compared to the unconjugated ApoB targeting LNA oligonucleotide (FIG. 7). The new compounds constructed with the GalNAc phosphoramidite (FIGS. 6 E, I, M and N) all showed a comparable effect on the target mRNA (ApoB mRNA) to the GalNAc2 cluster (GalNAc2) showing that different linker length and designs of the GalNAc conjugate moieties are tolerated by the ASGP receptor. The down regulation of ApoB mRNA in kidney (FIG. 7B) is higher for the unconjugated LNA oligonucleotide (control) than for the GalNAc conjugated compounds (FIGS. 6 E, I, M and N and GalNAc2) suggesting that the GalNAc moieties as expected are improving the liver uptake and lowering the kidney uptake of the LNA oligonucleotides. The lowering effect on total cholesterol levels (FIG. 8) is improved for all the GalNAc conjugated LNA oligonucleotides compared to the unconjugated LNA oligonucleotide.

Materials and Methods:

Analysis for ApoB mRNA Knockdown.

The animals were anaesthetised with 70% $CO_2$-30% $O_2$ and sacrificed by cervical dislocation. One half of the large liver lobe and one kidney were minced and submerged in RNAlater.

Total RNA was extracted from a maximum of 30 mg of tissue/sample, homogenized by bead-milling in the presence of lysis buffer (MagnaPure LC RNA Isolation Tissue buffer (#03604721001; Roche)) according to the manufacturer's instructions. The RNA was purified on a MagnaPure 96 System; Roche using Cellular RNA Large Volume Kit (#05467535001; Roche) using the manufacturer's standard protocol. First strand synthesis was performed using Reverse Transcriptase reagents from Ambion according to the manufacturer's instructions.

For each sample 0.5 µg total RNA was adjusted to (10.8 µl) with RNase free $H_2O$ and mixed with 2 µl random decamers (50 µM) and 4 µl dNTP mix (2.5 mM each dNTP) and heated to 70° C. for 3 min after which the samples were rapidly cooled on ice. 2 µl 10× Buffer RT, 1 µl MMLV Reverse Transcriptase (100 U/µl) and 0.25 µl RNase inhibitor (10 U/µl) were added to each sample, followed by incubation at 42° C. for 60 min, heat inactivation of the enzyme at 95° C. for 10 min and then the sample was cooled to 4° C. cDNA samples were diluted 1:5 and subjected to RT-QPCR using Taqman Fast Universal PCR Master Mix 2× (Applied Biosystems Cat #4364103) and Taqman gene expression assay (mApoB, Mn01545150_ml and mGAPDH #4352339E) following the manufacturers protocol and processed in an Applied Biosystems RT-qPCR instrument (7500/7900 or ViiA7) in fast mode.

Serum cholesterol analysis: Immediately before sacrifice retro-orbital sinus blood was collected using S-monovette Serum-Gel vials (Sarstedt, Numbrecht, Germany) for serum preparation. Serum was analyzed for total cholesterol using ABX Pentra Cholesterol CP (Triolab, Brondby, Denmark) according to the manufacturer's instructions.

Items

The invention is further characterized by the following items.

Item 1: A compound having the general formula (I)

wherein

NR'R" is a secondary amino group, wherein R' and R" are independently selected from $C_1$-$C_6$-alkyl or R' and R" together form a five- or six-membered ring, which may be substituted and which may contain one further heteroatom selected from N and O;

A is a $C_1$-$C_6$-alkyl group or a protected hydroxy- or thio-group; and

G is represented by general formula (II)

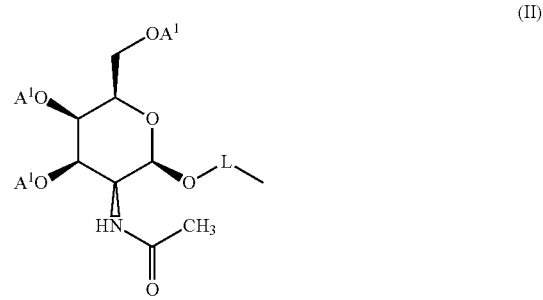

wherein $A^1$ is a suitable hydroxyl protecting group, which may be the same or different at each occurrence; and L is a linker group selected from the group consisting of $C_3$-$C_{19}$-alkylene but not C alkylene, $C_2$-$C_{30}$-alkenylene, —$CH_2CH_2$—$(OCH_2CH_2)_{0-4}$—$OCH_2CH_2$— and $CH_2CH_2$—$(OCH_2CH_2)_{6-8}$—$OCH_2CH_2$.

Item 2: The compound according to item 1, wherein the linker group L is selected from the group consisting of $C_7$-$C_{19}$-alkylene, $C_2$-$C_2$-alkenylene, and —$CH_2CH_2$—$(OCH_2CH_2)_{0-3}$—$OCH_2CH_2$—.

Item 3: The compound according to items 1 or 2, wherein the linker group L is selected from the group consisting of —$(CH_2)_2$—, —$(CH_2)_3$—, —$(CH_2)_4$—, —$(CH_2)_5$—, —$(CH_2)_7$—, —$(CH_2)_8$—, —$(CH_2)_9$—, —$(CH_2)_{10}$—, —$(CH_2)$—, —$(CH_2)_{12}$—, —$CH_2CH_2OCH_2CH_2$—, —$CH_2CH_2OCH_2CH_2OCH_2CH_2$—, and —$CH_2CH_2(OCH_2CH_2)_2OCH_2CH_2$—, Item 4: The compound according to any one of items 1 to 3, wherein the linker group L is selected from the group consisting of —(CH$_2$)$_2$—, —(CH$_2$)$_3$—, and —(CH$_2$)$_8$—.

Item 5: The compound according to any one of items 1 to 3, wherein the linker group L is selected from the group consisting of CH$_2$CH$_2$OCH$_2$CH$_2$—, —CH$_2$CH$_2$OCH$_2$CH$_2$OCH$_2$CH$_2$—, and —CH$_2$CH$_2$(OCH$_2$CH$_2$)$_2$OCH$_2$CH$_2$—.

Item 6: The compound according to any one of items 1 to 5, wherein the GalNAc moiety is in the beta configuration.

Item 7: The compound according to any one of items 1 to 6, wherein the secondary amino group —NR'R" is selected from the group consisting of dimethylamino, diethylamino, diisopropylamino, dibutylamino, pyrrolidino, piperidino, 2,6-dimethylpiperidino, morpholino, imidazolyl and 4-methylimidazolyl.

Item 8: The compound according to any one of items 1 to 7, wherein A is selected from the group consisting of 2-cyanoethoxy, 2-cyanoethylthio, methoxy, ethoxy, S-isobutanoyl-2-(2-mercaptoethoxy)ethoxy, S-pivaloyl-2-(2-mercaptoethoxy)ethoxy, S-pivaloyl-2-mercaptoethoxy, methyl and ethyl.

Item 9: The compound according to any one of items 1 to 8, wherein the hydroxyl protecting group A$^1$ is selected from an acyl group and a silyl group, preferably from the group consisting of acetyl, benzoyl, phenoxy-acetyl, pivaloyl, dimethoxytrityl (DMT), isobutyryl, t-butyldimethylsilyl, t-butyldiphenylsilyl, triisopropylsilyland isopropyldimethylsilyl.

Item 9a: The compound according to any one of items 1 to 9, wherein the hydroxyl protecting group A$^1$ in position 6 on the sugar is dimethoxytrityl (DMT).

Item 10: The compound according to any one of items 1 to 9a, wherein
A is —O—CH$_2$CH$_2$CN, A$^1$ is acetyl, R' and R" each are isopropyl, and L is selected from the group consisting of —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$CH$_2$OCH$_2$CH$_2$—, —CH$_2$CH$_2$OCH$_2$CH$_2$OCH$_2$CH$_2$—, and —CH$_2$CH$_2$(OCH$_2$CH$_2$)$_2$OCH$_2$CH$_2$—, preferably from —(CH$_2$)$_2$— and —(CH$_2$)$_3$—.

Item 11: A compound having the general formula (III)

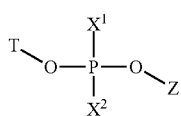
(III)

wherein
Z is a nucleic acid molecule;
T is represented by general formula (IV) or alternatively by general formula (VI)

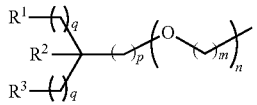
(IV)

wherein
R$^2$ represents H or —(CH$_2$)$_q$—R$^1$,
R$^1$ and R$^3$ at each occurrence are represented by general formula (V),

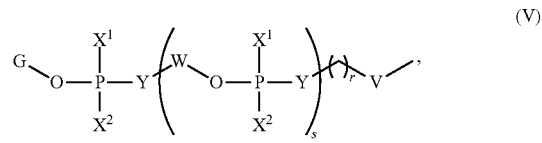
(V)

wherein independently at each occurrence
V is selected from —O—, —NH—CO— and —CO—NH—;
W is selected from the group consisting of —(CH$_2$)$_{2-15}$— and —CH$_2$CH$_2$(OCH$_2$CH$_2$)$_{0-4}$OCH$_2$CH$_2$—;
Y is O or S;
m is an integer from 1 to 3;
n is an integer from 0 to 5;
p is an integer from 0 to 3; and
q is an integer from 1 to 2;
r is an integer from 1 to 5;

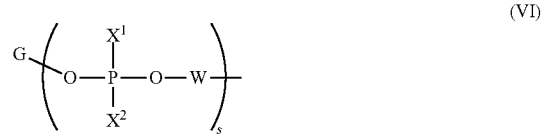
(VI)

wherein independently at each occurrence in formula (V) and (VI)
s is 0 or 1
G is represented by general formula (II)'

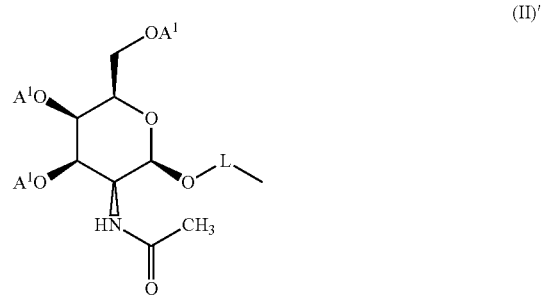
(II)' wherein A is H or a suitable hydroxyl protecting group, which may be the same or different at each occurrence; and L is selected from the group consisting of C$_2$-C$_{20}$-alkenylene, —CH$_2$CH$_2$—(OCH$_2$CH$_2$)$_{0-6}$—OCH$_2$CH$_2$, —(CH$_2$)$_2$—, —(CH$_2$)$_3$—, —(CH$_2$)$_4$—, —(CH$_2$)$_5$—, —(CH$_2$)$_7$—, —(CH$_2$)$_8$—, —(CH$_2$)$_9$—, —(CH$_2$)$_{10}$—, —(CH$_2$)$_{11}$—, —(CH$_2$)$_{12}$—, —CH$_2$CH$_2$OCH$_2$CH$_2$—, —CH$_2$CH$_2$OCH$_2$CH$_2$OCH$_2$CH$_2$—, and —CH$_2$CH$_2$(OCH$_2$CH$_2$)$_2$OCH$_2$CH$_2$—; and
independently at each occurrence in formula (III), (V) and (VI)
X$^1$ is —OH and X$^2$ is selected from =O and =S, or
X$^1$ is —O$^-$ and X$^2$ is selected from =O and =S, or
X$^1$ is =O and X$^2$ is selected from —CH$_3$, —OR, —NHR, and —BH$_3$, wherein R is independently at each occurrence a C$_1$-C$_6$ alkyl group, or $X^1$ is $=S$ and $X^2$ is selected from $—CH_3$ and $—SH$, wherein the contiguous chain starting with the first atom of linker L in R1, R3 or, if R2 is not H, R2 or in formula (VI), and ending with the attachment point in formula (IV) or in the nucleic acid molecule if T is represented by formula (VI) has a minimum length of 8 atoms and a maximum length of 30 atoms.

Item 12: The compound according to item 11, wherein s is 1.

Item 13: The compound according to item 11, wherein s is 0.

Item 14: The compound according to items 11, wherein T is represented by formula (VI) and s is 0.

Item 15: The compound according to any one of items 11 to 14, wherein the GalNac moiety in formula (II') is in the beta conformation.

Item 16: The compound according to any one of items 11 to 15, wherein W is selected from the group consisting of $—CH_2CH_2OCH_2CH_2OCH_2CH_2—$, $—CH_2CH_2(OCH_2CH_2)_4OCH_2CH_2—$, $—CH_2CH_2CH_2—$, and $—(CH_2)_{12}—$.

Item 17: The compound according to any one of items 11 to 16, wherein independently at each occurrence
$X^1$ is $—OH$ and $X^2$ is $=O$, or
$X^1$ is $O^-$ and $X^2$ is $=O$, or
$X^1$ is $—OH$ and $X^2$ is $=S$, or
$X^1$ is $O^-$ and $X^2$ is $=S$, or
$X^1$ is $=S$ and $X^2$ is $—SH$.

Item 18: The compound according to any one of items 11 to 17, wherein the contiguous chain starting with the first atom of linker L in $R^1$, $R^3$ or, if $R^2$ is not H, $R^2$, and ending with the branching point carbon atom in formula (IV)

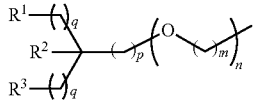

(IV)

has a length of from 9 to 23 atoms.

Item 19: The compound according to item 11 to 18, wherein the nucleic acid molecule is selected from DNA, RNA and nucleic acid analogue molecules, particularly from antisense oligonucleotides, small interfering RNAs, and microRNAs.

Item 20: The compound according to item 11 to 19, wherein the nucleic acid molecule contains locked nucleic acid nucleotides.

Item 21: The compound according to item 11 to 20, wherein the nucleic acid molecule contain one or more phosphorothioate or boranophosphate internucleoside linkages.

Item 22: The compound according to item 11 to 21, wherein all DNA and RNA nucleosides are linked with phosphorothioate or boranophosphate.

Item 23: The compound according to item 11 to 22, wherein all the nucleosides and/or nucleoside analogues in the nucleic acid molecule are linked with phosphorothioate or boranophosphate.

Item 24: The compound according to any one of items 11 to 23, wherein the 5' end of the nucleic acid molecule is attached to the GalNAc conjugate moiety.

Item 25: The compound according to item 11 to 24, wherein a PO linker is placed between the nucleic acid and the GalNAc conjugate moiety.

Item 26: The compound according to item 11 to 25, wherein the compound is capable of binding to the asialoglycoprotein receptor (ASGPR).

Item 27: A Process for the preparation of a compound according to any one of items 1 to 9, comprising the steps:
(i) stereoselectively forming an internal oxazoline ring between carbon atoms 1 and 2 of N-Acetylgalactosamine (GalNAc);
(ii) reacting the product of step (i) with a compound having the general formula $HO-L-O-A^3$, wherein
$A^3$ is a suitable protecting group and
L is a linker group selected from the group consisting of $—(CH_2)_2—$, $—(CH_2)_3—$, $—(CH_2)_4—$, $—(CH_2)_5—$, $—(CH_2)_7—$, $—(CH_2)_8—$, $—(CH_2)_9—$, $—(CH_2)_{10}—$, $—(CH_2)_{11}—$, $—(CH_2)_{12}—$, $—CH_2CH_2OCH_2CH_2—$, $—CH_2CH_2OCH_2CH_2OCH_2CH_2—$, and $—CH_2CH_2(OCH_2CH_2)_2OCH_2CH_2—$,
thereby forming an ether bond at carbon atom 1 of the GalNAc ring;
(iii) deprotecting the $—O-A^3$ group in the product of step (ii), thereby providing a deprotected $—OH$ group,
(iv) reacting the product of step (iii) with a phosphordiamidite, thereby providing a compound according to any one of items 1 to 9.

Item 28: A Process for the preparation of a nucleic acid conjugate, comprising the steps:
(i) providing a nucleic acid molecule on a solid support;
(ii) optionally adding a brancher molecule to the nucleic acid molecule using phosphoramidite chemistry, wherein said brancher molecule after addition results in structures preferably represented by general formula (IV a)

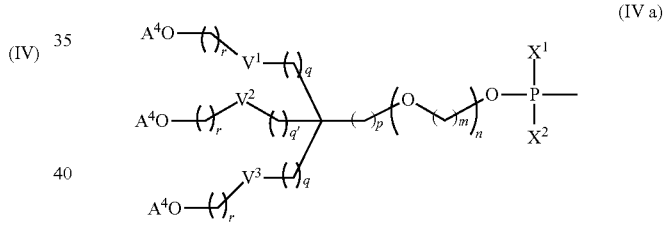

(IV a)

wherein
$A^4$ is a suitable protecting group;
$V^1$ is selected from $—O—$, $—NH—CO—$ and $—CO—NH—$;
$V^2$ is absent or is selected from $—O—$, $—NH—CO—$ and $—CO—NH—$;
$V^3$ is selected from $—O—$, $—NH—CO—$ and $—CO—NH—$;
$X^1$ is $—OH$ and $X^2$ is selected from $=O$ and $=S$, or
$X^1$ is $O^-$ and $X^2$ is selected from $=O$ and $=S$, or
$X^1$ is $=O$ and $X^2$ is selected from $—CH_3$, $—SH$, $—OR$, $—NHR$, and $—BH_3$, wherein R is independently at each occurrence a $C_1$-$C_6$ alkyl group, or
$X^1$ is $=S$ and $X^2$ is selected from $—CH_3$ and $—SH$;
m is an integer from 1 to 3;
n is an integer from 0 to 5;
p is an integer from 0 to 3; and independently at each occurrence
q is an integer from 1 to 2;
q' is an integer from 0 to 2; and
r is an integer from 1 to 5;
with the proviso that when $V^2$ is absent, q' is 0 and $—(CH_2)_r—OA^4$ attached to $V^2$ in formula (IV a) is also absent;

(iii) optionally adding a spacer phosphoramidite molecule to each of the branches of the brancher molecule using phosphoramidite chemistry, wherein said spacer molecule after addition results in structures preferably represented by general formula (V a)

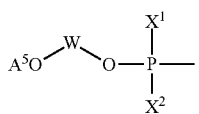

(V a)

wherein independently at each occurrence
$A^5$ is a suitable protecting group;
W is selected from the group consisting of $-(CH_2)_{2-15}-$ and $-CH_2CH_2(OCH_2CH_2)O_4OCH_2CH_2-$;
$X^1$ is $-OH$ and $X^2$ is selected from $=O$ and $=S$, or
$X^1$ is $O^-$ and $X^2$ is selected from $=O$ and $=S$, or
$X^1$ is $=O$ and $X^2$ is selected from $-CH_3$, $-SH$, $-OR$, $-NHR$, and $-BH_3$, wherein R is independently at each occurrence a $C_1$-$C_6$ alkyl group, or
$X^1$ is $=S$ and $X^2$ is selected from $-CH_3$ and $-SH$;
(iv) reacting a compound according to any one of items 1-9 with the reactive end of the nucleic acid molecule, if no brancher molecule is present, or reacting a compound according to any one of items 1-9 with the reactive end of each of the branches, if a brancher molecule is present and no spacer is present, or reacting a compound according to any one of items 1-9 with the reactive end of each of the spacers, if spacers are present; and
(v) cleaving the product of step (iv) from the solid support;
wherein the contiguous chain starting with the first atom of linker L in the compound according to any one of items 1-9, and ending with the attachment point in formula (IVa) or the attachment point in the nucleic acid molecule has a minimum length of 8 atoms and a maximum length of 30 atoms.

Item 29: The process according to item 28, wherein the nucleic acid molecule is selected from DNA, RNA and molecules comprising one or more nucleoside analogues, particularly the nucleic acid molecule is selected from antisense oligonucleotides, gapmers, small interfering RNAs, and microRNAs.

Item 30: The process according to item 28 or 29, wherein the nucleic acid molecule contains locked nucleic acid nucleotides.

Item 31: The process according to any one of items 28 to 230, wherein the nucleic acid molecule contain one or more phosphorothioate or boranophosphate internucleoside linkages.

Item 32: The process according to any one of items 28 to 31, wherein all DNA and RNA nucleosides are linked with phosphorothioate or boranophosphate.

Item 33: The process according to any one of items 28 to 32, wherein all the nucleosides and/or nucleoside analogues in the nucleic acid molecule are linked with phosphorothioate or boranophosphate.

Item 34: The process according to any one of items 28 to 33, wherein the brancher molecule, spacer molecule or a compound according to any one of items 1 to 9 is reacted with the 5' end of the nucleic acid molecule.

Item 35: The process according to any one of items 28 to 34, wherein a PO linker is placed between the nucleic acid molecule and the brancher molecule, spacer molecule or a compound according to any one of items 1 to 9.

Item 36: The process according to any one of items 28 to 35, wherein the brancher molecule is selected from the group consisting of:

1,3-bis-[5-(4,4'-dimethoxytrityloxy)pentylamido]propyl-2-[(2-cyanoethyl)-(N,N-diisopropyl)]phosphoramidite;

tris-2,2,2-[3-(4,4'-dimethoxytrityloxy)propyloxymethyl]ethyl-[(2-cyanoethyl)-(N,N-diisopropyl)]-phosphoramidite; and tris-2,2,2-[3-(4,4'-dimethoxytrityloxy)propyloxymethyl]methyleneoxypropyl-[(2-cyanoethyl)-(N,N-diisopropyl)]-phosphoramidite.

Item 37: The process according to any one of items 28 to 36, wherein the spacer phosphoramidite molecule is represented by general formula (VII)

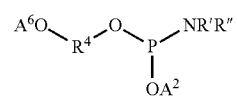

(VII)

wherein $A^2$ is a suitable protecting group, preferably $-CH_2CH_2CN$, $A^6$ is a suitable protecting group such as 4',4'-Dimethoxytrityl and $R^4$ is selected from the group consisting of: $-CH_2CH_2OCH_2CH_2OCH_2CH_2-$, $-CH_2CH_2(OCH_2CH_2)_4OCH_2CH_2-$, $-CH_2CH_2CH_2-$, and $-(CH_2)_{12}-$; and NR'R" is a secondary amino group, wherein R' and R" are independently selected from $C_1$-$C_6$-alkyl or R' and R" together form a five- or six-membered ring, which may be substituted and which may contain one further heteroatom selected from N and 0.

Item 38: Use of a compound according to any one of items 1 to 9 for the preparation of compounds according to any one of items 10 to 26.

Item 39: Use of a compound according to any one of items 10 to 26 as a medicament.

Item 40: A compound according to any one of items 10 to 26 for use in reduction of a liver mRNA target.

Item 41: A compound according to any one of items 10 to 26 for use in the treatment of a liver disease.

Item 42: A compound according to any one of items 10 to 26 for use in treatment of a metabolic disease or disorder, or a hepatic disease or disorder. In particular for the treatment of diseases such as hepatitis (including viral hepatitis, such as HBV or HCV), hepatic steatosis (including metabolic malfunctions), atherosclerosis, hyperlipidemia, hypercholesterolemia, familiar hypercholesterolemia e.g. gain of function mutations in Apolipoprotein B, HDL/LDL cholesterol imbalance, dyslipidemias, e.g., familial hyperlipidemia (FCHL), acquired hyperlipidemia, statin-resistant hypercholesterolemia, coronary artery disease (CAD), and coronary heart disease (CHD), acute coronary syndrome (ACS), liver-fibrosis (or disease associated with liver-fibrosis), cirrhosis and cancer Item 43: A method of treatment comprising administering to a human or animal a compound according to any one of items 10 to 26 in an effective amount.

The invention claimed is:
1. A compound selected from the group consisting of:

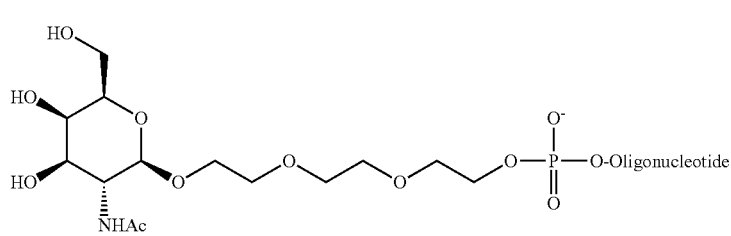

(A)

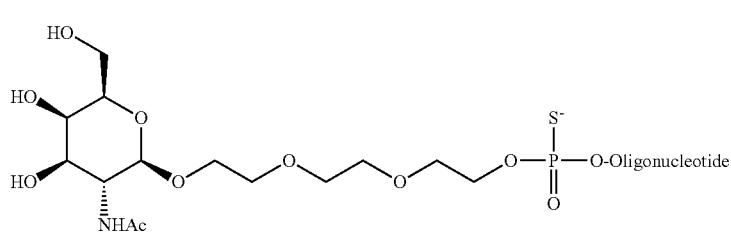

(B)

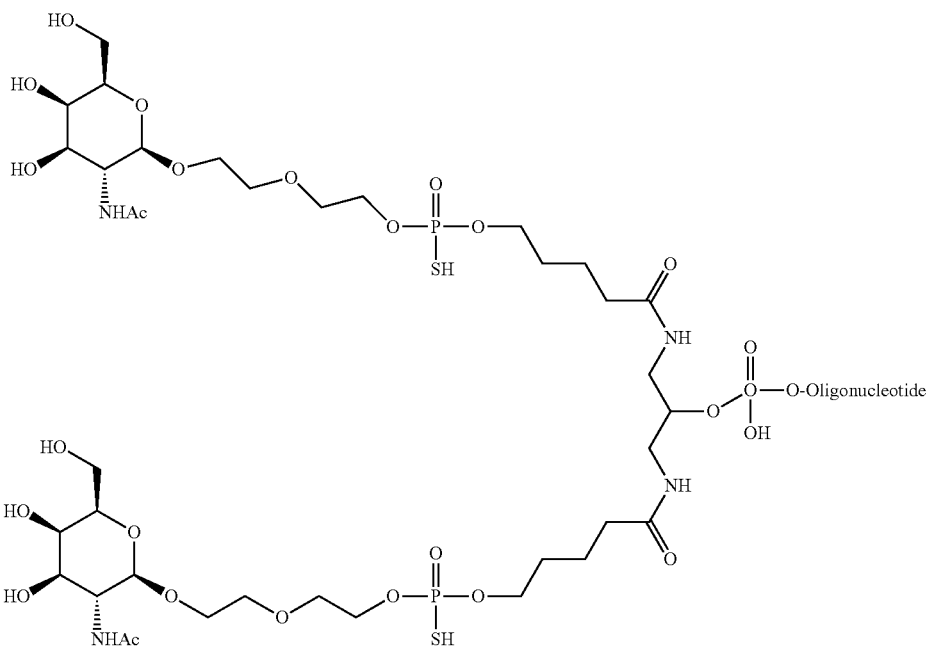
(C)
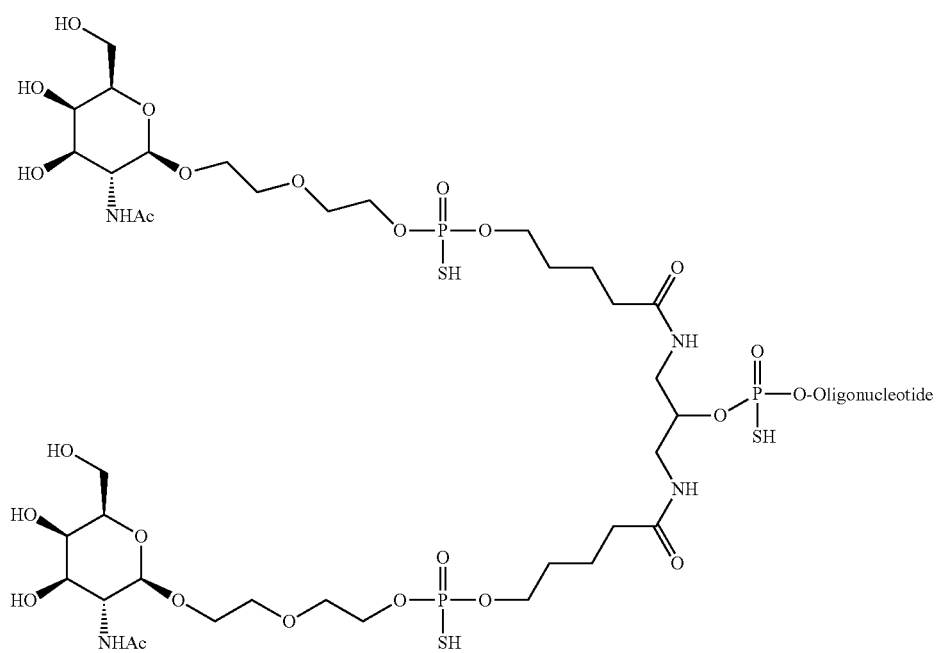
(D)

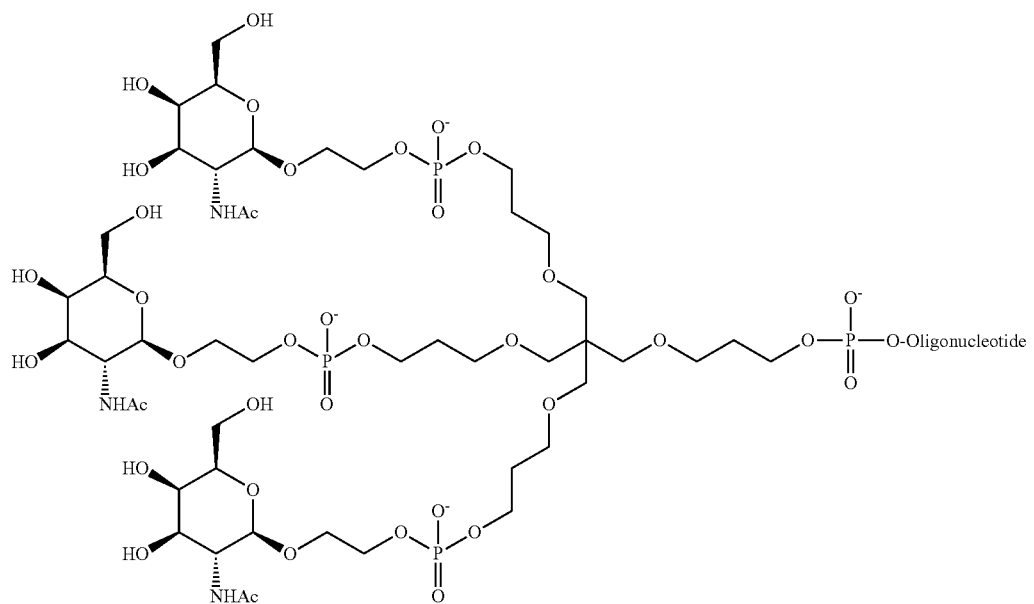
(E)
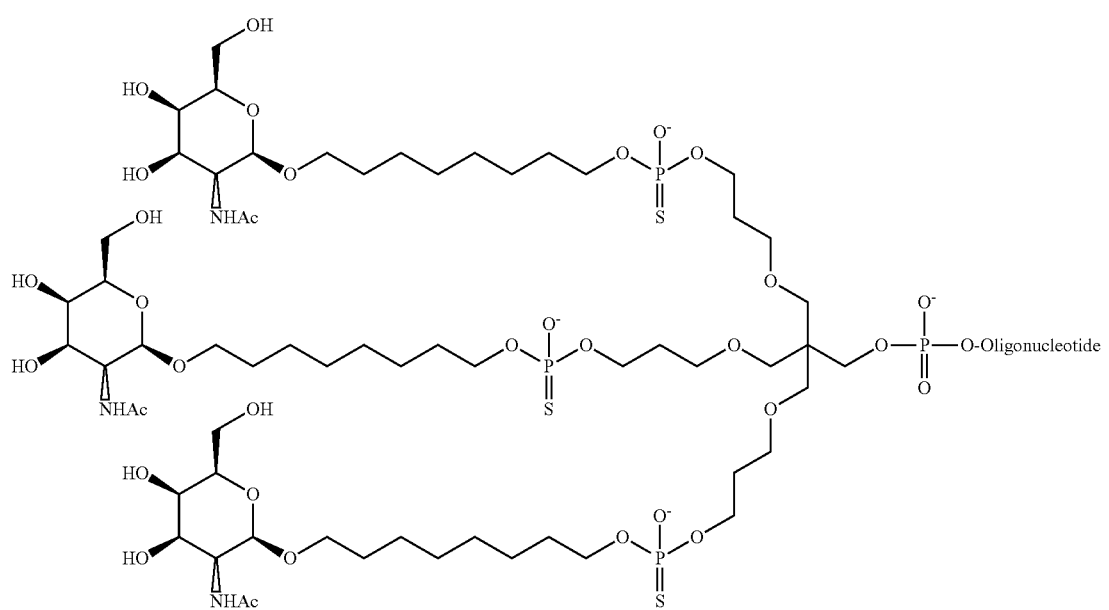
(F)

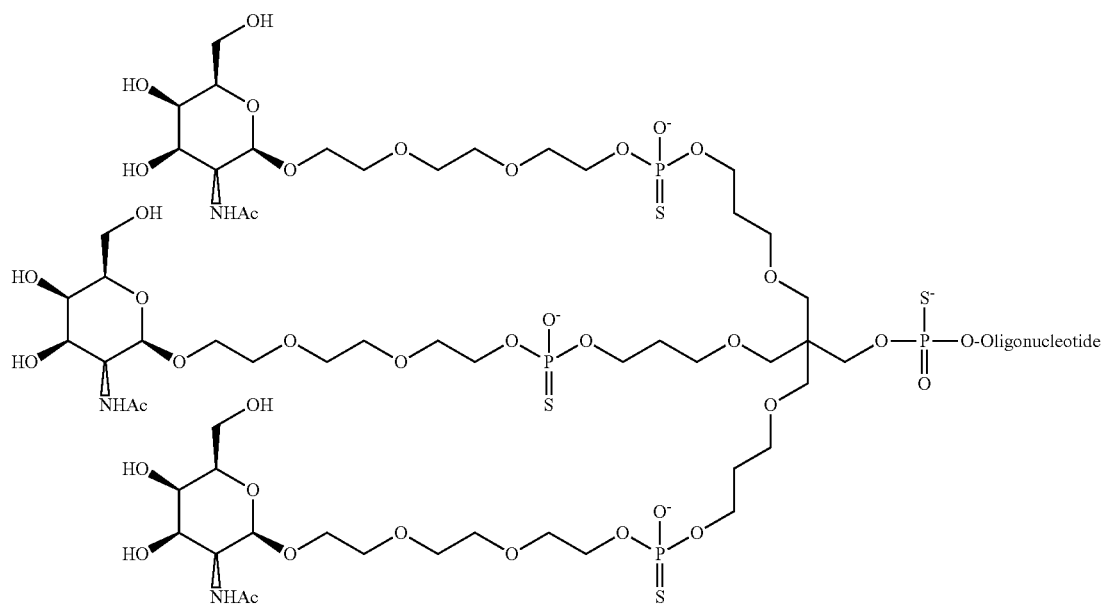
(G)
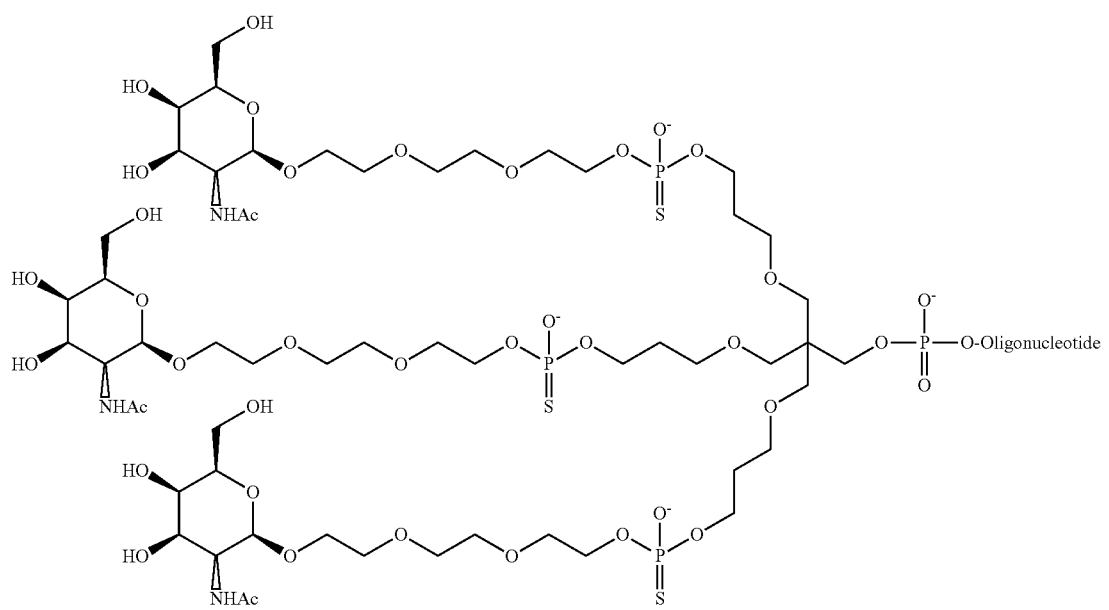
(H)

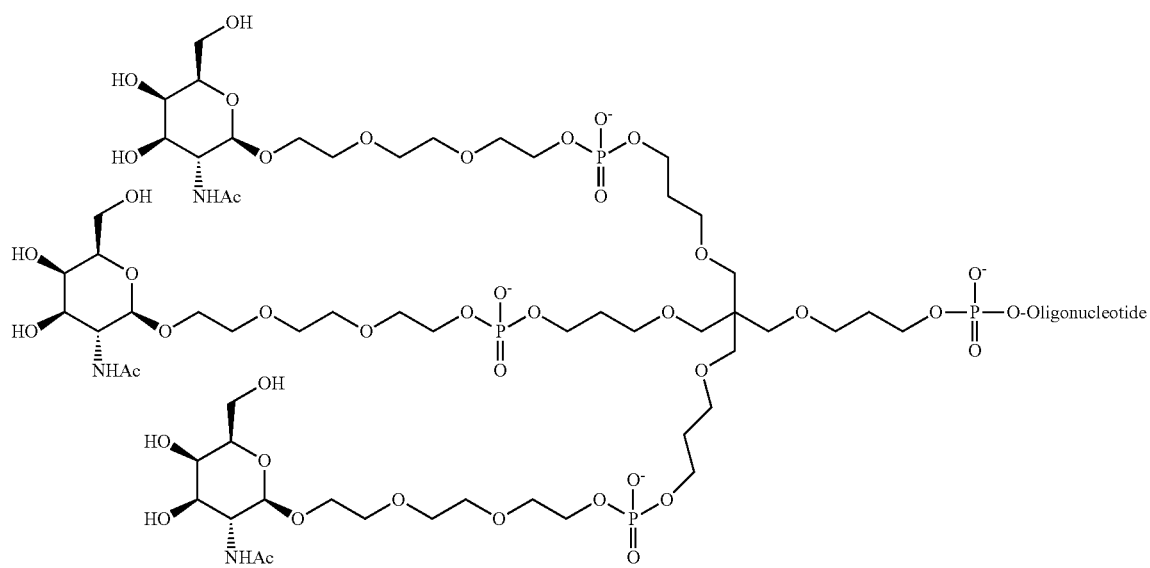
(I)
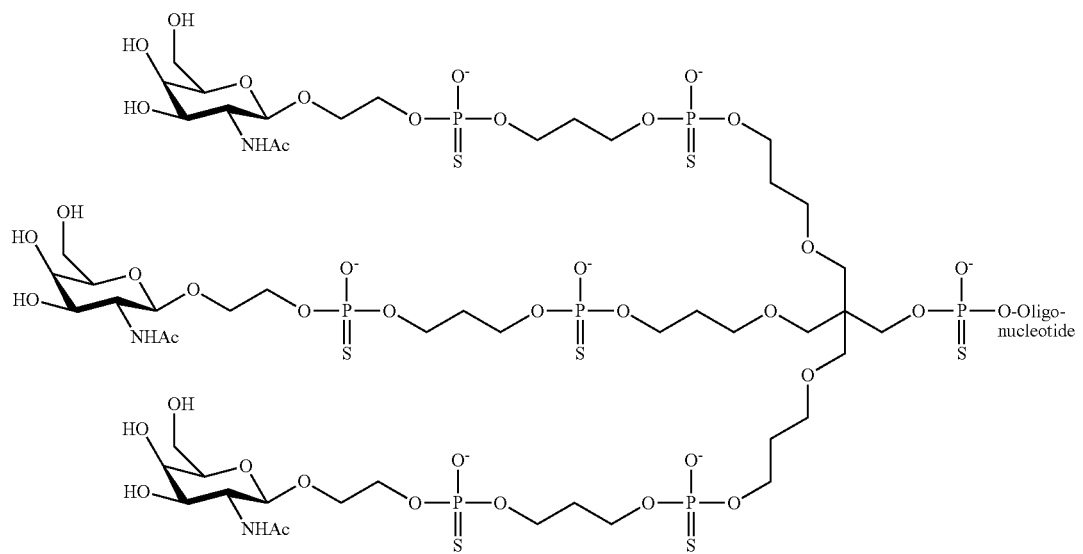
(J)

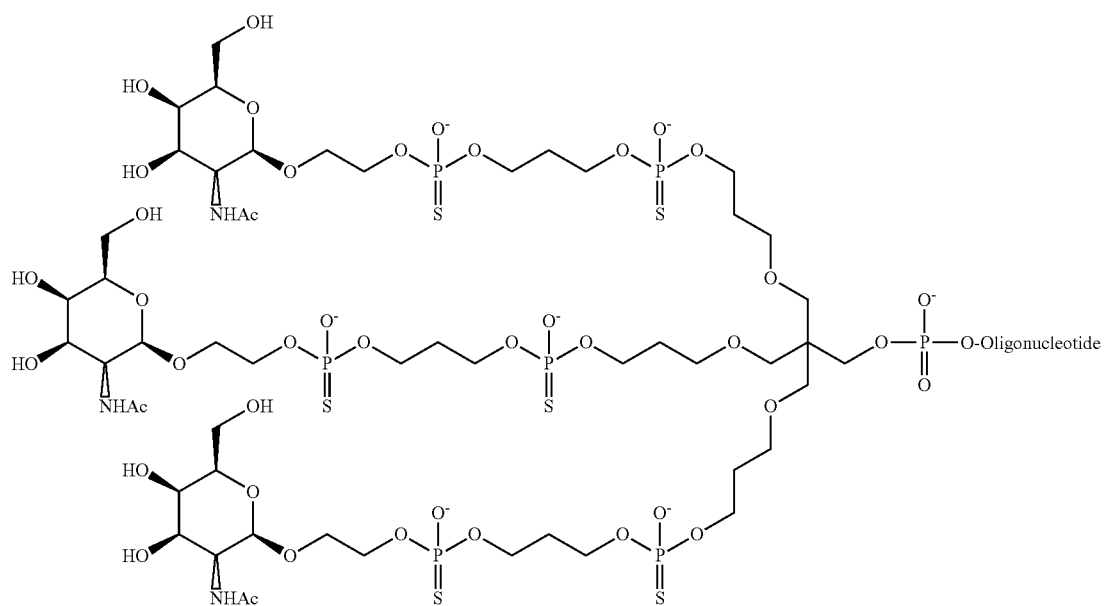
(K)
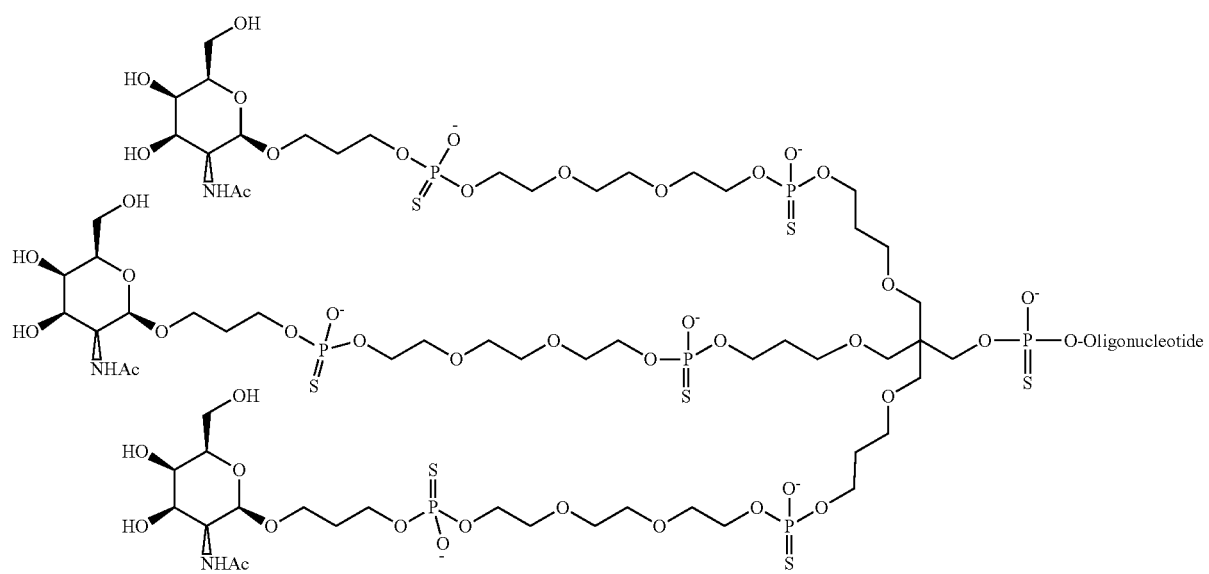
(L)

(M)
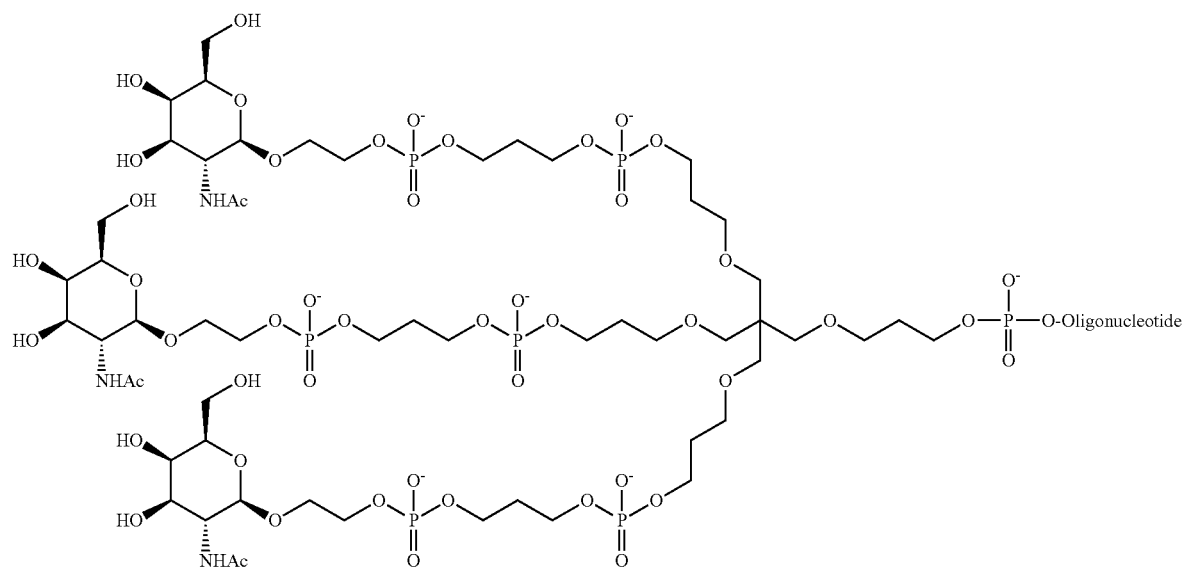
(N)
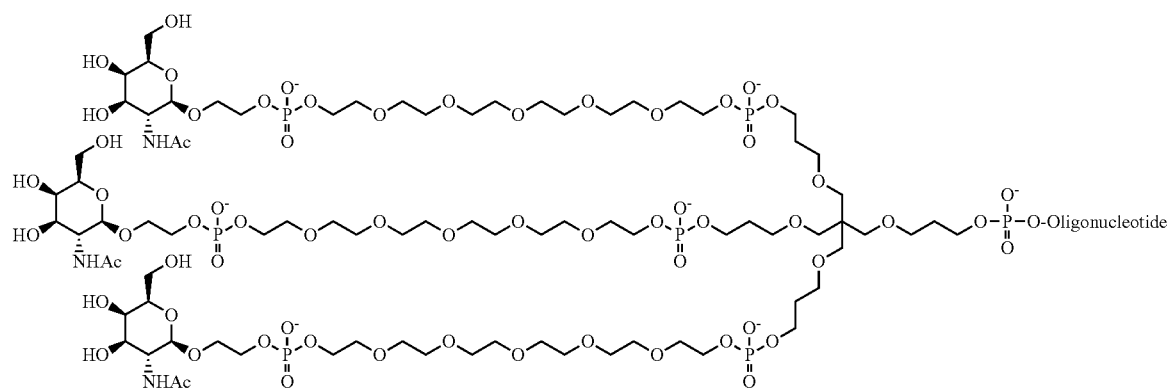
2. A medicament comprising a compound of claim 1.
* * * * *

UNITED STATES PATENT AND TRADEMARK OFFICE
CERTIFICATE OF CORRECTION

| | | |
|---|---|---|
| PATENT NO. | : 11,505,569 B2 | Page 1 of 1 |
| APPLICATION NO. | : 16/987225 | |
| DATED | : November 22, 2022 | |
| INVENTOR(S) | : Nanna Albaek, Jacob Ravn and Christoph Rosenbohm | |

It is certified that error appears in the above-identified patent and that said Letters Patent is hereby corrected as shown below:

On the Title Page

Please amend the Related U.S. Application Data (item (62)) to read as follows:
Division of application No. 15/517,685, filed as application No. PCT/EP2015/073331 on Oct. 9, 2015, now abandoned."

Signed and Sealed this
Third Day of December, 2024

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 13
<212> TYPE: DNA
<213> ORGANISM: Artificial Sequence
<220> FEATURE:
<223> OTHER INFORMATION: oligonucleotide
<220> FEATURE:
<221> NAME/KEY: phosphorothiate Internucleoside linkages
<222> LOCATION: (1)..(13)
<220> FEATURE:
<221> NAME/KEY: LNA nucleosides, LNA C is 5-methyl C
<222> LOCATION: (1)..(2)
<220> FEATURE:
<221> NAME/KEY: LNA nucleosides, LNA C is 5-methyl C
<222> LOCATION: (11)..(13)

<400> SEQUENCE: 1
gcattggtat tca                                                      13

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: phosphodiester lnternucleoside linkages
<222> LOCATION: (1)..(3)
<220> FEATURE:
<221> NAME/KEY: LNA nucleosides, LNA C is 5-methyl C
<222> LOCATION: (3)..(5)
<220> FEATURE:
<221> NAME/KEY: phosphorothiate Internucleoside linkages
<222> LOCATION: (4)..(15)
<220> FEATURE:
<221> NAME/KEY: LNA nucleosides, LNA C is 5-methyl C
<222> LOCATION: (13)..(15)

<400> SEQUENCE: 2
cagcattggt attca                                                    15